US010975035B2

(12) United States Patent
Bunker et al.

(10) Patent No.: US 10,975,035 B2
(45) Date of Patent: *Apr. 13, 2021

(54) BICYCLIC COMPOUNDS

(71) Applicant: Recurium IP Holdings, LLC, San Diego, CA (US)

(72) Inventors: Kevin Duane Bunker, Escondido, CA (US); Chuangxing Guo, San Diego, CA (US); Mark Charles Grier, San Diego, CA (US); Chad Daniel Hopkins, San Diego, CA (US); Joseph Robert Pinchman, San Diego, CA (US); Deborah Helen Slee, Encinitas, CA (US); Peter Qinhua Huang, San Diego, CA (US); Mehmet Kahraman, San Diego, CA (US)

(73) Assignee: Recurium IP Holdings, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/379,487

(22) Filed: Apr. 9, 2019

(65) Prior Publication Data

US 2019/0233377 A1   Aug. 1, 2019

Related U.S. Application Data

(63) Continuation of application No. 14/855,102, filed on Sep. 15, 2015, now Pat. No. 10,308,609.

(60) Provisional application No. 62/051,760, filed on Sep. 17, 2014.

(51) Int. Cl.

| C07D 213/89 | (2006.01) |
|---|---|
| A61K 31/164 | (2006.01) |
| C07C 233/05 | (2006.01) |
| C07C 233/14 | (2006.01) |
| A61K 31/27 | (2006.01) |
| A61K 31/13 | (2006.01) |
| C07C 211/38 | (2006.01) |
| A61K 31/444 | (2006.01) |
| A61K 45/06 | (2006.01) |
| C07C 317/30 | (2006.01) |
| C07C 215/42 | (2006.01) |
| C07C 233/06 | (2006.01) |
| C07C 233/09 | (2006.01) |
| C07C 233/13 | (2006.01) |
| C07C 233/23 | (2006.01) |
| A61K 31/145 | (2006.01) |
| A61K 31/16 | (2006.01) |

(52) U.S. Cl.
CPC ........... *C07D 213/89* (2013.01); *A61K 31/13* (2013.01); *A61K 31/145* (2013.01); *A61K 31/16* (2013.01); *A61K 31/164* (2013.01); *A61K 31/27* (2013.01); *A61K 31/444* (2013.01); *A61K 45/06* (2013.01); *C07C 211/38* (2013.01); *C07C 215/42* (2013.01); *C07C 233/05* (2013.01); *C07C 233/06* (2013.01); *C07C 233/09* (2013.01); *C07C 233/13* (2013.01); *C07C 233/14* (2013.01); *C07C 233/23* (2013.01); *C07C 317/30* (2013.01); *C07C 2601/02* (2017.05); *C07C 2602/38* (2017.05); *C07C 2603/62* (2017.05)

(58) Field of Classification Search
CPC .. A61K 2300/00; A61K 31/13; A61K 31/145; A61K 31/16; A61K 31/164; A61K 31/27; A61K 31/444; A61K 45/06; A61P 19/02; A61P 21/00; A61P 25/04; A61P 29/00; A61P 35/00; A61P 43/00; C07C 211/38; C07C 215/42; C07C 233/05; C07C 233/06; C07C 233/09; C07C 233/13; C07C 233/14; C07C 233/23; C07C 2601/02; C07C 2602/38; C07C 2603/62; C07C 317/30; C07D 213/89
USPC .................. 546/261; 560/115; 564/210, 460
See application file for complete search history.

(56) References Cited

U.S. PATENT DOCUMENTS

| 5,262,417 A | 11/1993 | Gammill et al. |
|---|---|---|
| 5,385,906 A | 1/1995 | Gammill et al. |
| 5,405,550 A | 4/1995 | Horst |
| 6,136,861 A | 10/2000 | Chenard |
| 8,846,698 B2 | 9/2014 | Andrews et al. |
| 9,326,973 B2 | 5/2016 | Hewawasam et al. |
| 9,447,025 B2 | 9/2016 | Bunker |
| 9,447,026 B2 | 9/2016 | Bunker |
| 9,693,975 B2 | 7/2017 | Bunker |
| 9,724,316 B2 | 8/2017 | Bunker |
| 10,189,780 B2 | 1/2019 | Bunker |
| 10,251,851 B2 * | 4/2019 | Bunker ................. A61K 31/14 |

(Continued)

FOREIGN PATENT DOCUMENTS

| CN | 1898244 A | 1/2007 |
|---|---|---|
| CN | 103588668 A | 2/2014 |

(Continued)

OTHER PUBLICATIONS

Office Action dated Apr. 12, 2019 for CN Application No. 201580061363.9, filed Sep. 15, 2015.

(Continued)

*Primary Examiner* — Sabiha N Qazi
(74) *Attorney, Agent, or Firm* — Knobbe Martens Olson & Bear LLP

(57) ABSTRACT

Disclosed herein are compounds of Formulae (I) and (II), methods of synthesizing compounds of Formulae (I) and (II), and methods of using compounds of Formulae (I) and (II) as an analgesic.

25 Claims, No Drawings

(56) References Cited

U.S. PATENT DOCUMENTS

| | | | |
|---|---|---|---|
| 10,308,609 | B2 | 6/2019 | Bunker et al. |
| 10,525,036 | B2* | 1/2020 | Huang .................. C07D 487/10 |
| 2004/0092531 | A1 | 5/2004 | Chizh et al. |
| 2006/0052370 | A1 | 3/2006 | Meyerson et al. |
| 2007/0082956 | A1 | 4/2007 | Magerl et al. |
| 2007/0254862 | A1 | 11/2007 | Antel et al. |
| 2009/0088418 | A1 | 4/2009 | Pfister et al. |
| 2010/0056553 | A1 | 3/2010 | Plettenburg et al. |
| 2012/0108583 | A1 | 5/2012 | Gharat et al. |
| 2012/0122846 | A1 | 5/2012 | Calderwood et al. |
| 2012/0245137 | A1 | 9/2012 | Pajouhesh et al. |
| 2012/0270893 | A1 | 10/2012 | Dow et al. |
| 2013/0029987 | A1 | 1/2013 | Bennett et al. |
| 2013/0237559 | A1 | 9/2013 | Ortiz et al. |
| 2014/0275245 | A1 | 9/2014 | Bunker |
| 2015/0018328 | A1 | 1/2015 | Konteatis et al. |
| 2015/0246890 | A1 | 9/2015 | Bahmanyar et al. |
| 2015/0297562 | A1 | 10/2015 | Iinuma et al. |
| 2016/0016892 | A1 | 1/2016 | Bunker |
| 2016/0075654 | A1 | 3/2016 | Bunker et al. |
| 2016/0311766 | A1 | 10/2016 | Bunker |
| 2016/0355462 | A1 | 12/2016 | Bunker |
| 2016/0374968 | A1 | 12/2016 | Bunker |
| 2017/0081295 | A1 | 3/2017 | Bunker |
| 2018/0042871 | A1* | 2/2018 | Bunker .................. A61K 31/235 |
| 2019/0060257 | A1 | 2/2019 | Bunker et al. |
| 2019/0298668 | A1* | 10/2019 | Bunker .................. A61K 31/14 |

FOREIGN PATENT DOCUMENTS

| | | |
|---|---|---|
| CN | 103588672 A | 2/2014 |
| CN | 105814013 | 7/2016 |
| CN | 106232567 A | 12/2016 |
| EP | 0372466 A2 | 6/1990 |
| IL | 54795 | 10/1980 |
| JP | H04 502317 | 4/1992 |
| JP | 2008-120797 | 5/2008 |
| JP | 2016-518317 | 6/2016 |
| JP | 2017-501218 | 1/2017 |
| TW | 201443001 | 11/2014 |
| WO | WO 90/06307 | 6/1990 |
| WO | WO 2000/056318 | 9/2000 |
| WO | WO 2001/091736 | 12/2001 |
| WO | WO 2005/063754 | 7/2005 |
| WO | WO 2008/096218 | 8/2008 |
| WO | WO 2009/153720 | 12/2009 |
| WO | WO 2012/137089 | 10/2012 |
| WO | WO 2012/145569 | 10/2012 |
| WO | WO 2013/024895 | 2/2013 |
| WO | WO 2013/126856 | 8/2013 |
| WO | WO 2013/131018 | 9/2013 |
| WO | WO 2014/070939 | 5/2014 |
| WO | WO 2014/149819 | 9/2014 |
| WO | WO 2014/169226 | 10/2014 |
| WO | WO 2014/206922 | 12/2014 |
| WO | WO 2015/061247 | 4/2015 |
| WO | WO 2015/089170 | 6/2015 |
| WO | WO 2015/134710 | 9/2015 |
| WO | WO 2015/157127 | 10/2015 |
| WO | WO 2015/159175 | 10/2015 |
| WO | WO 2015/162459 | 10/2015 |
| WO | WO 2016/016370 | 2/2016 |
| WO | WO 2017/160926 | 9/2017 |

OTHER PUBLICATIONS

Office Action dated Aug. 20, 2019 for JP Application No. 2017-514844, filed Sep. 15, 2015.
Office Action and Search Report dated Jun. 27, 2019 for TW Application No. 104130651, filed Sep. 16, 2015.
Adcock, W., et al., "Transmission of polar substituent effects across the bicyclo[1.1.1]pentane ring system as monitored by $^{19}$F NMR shifts" *Magn. Reson. Chem.* (2000) 38:115-122.

Adcock, W., et al., "Computation and analysis of 19F substituent chemical shifts of some bridgehead-substituted polycyclic alkyl fluorides" *Magn. Reson. Chem.* (2003) 41(7):503-508.
Adcock et al., "Polar Substituent Effects in the Bicyclo[1.1.1]pentane Ring System: Acidities of 3-Substituted Bicyclo[1.1.1]pentane-l-carboxylic Acids" *J.Org. Chem.* (2005) 70(3):1029-1034.
Adcock, W., "A DFT-GIAO and DFT-NBO study of polar substituent effects on NMR $^{17}$O chemical shifts in some rigid polycyclic alkanes" *J. Phys. Org. Chem.* (2011) 24:492-498.
Adcock et al., "Transmission of Polar Substituent Effects through Bicyclo[1.1.1]pentane Ring System as Monitored by 19F NMR Shifts" *Tetrahedron Letters* (1992) 33(48):7397-7398.
Annese, C., et al., "Oxyfunctionalization of Non-Natural Targets by Dioxiranes. 6. On the Selective Hydroxylation of Cubane" *Org. Lett.* (2009) 11(16):3574-3577.
Applequist, D.E., et al., "Polar Substituent Effects in 1,3-Disubstituted Bicyclo[1.1.1]pentanes" *J. Org. Chem.* (1982) 47:4985-4995.
Arnone A., et al., "Highly Enantiospecific Oxyfunctionalization of Nonactivated Hydrocarbon Sites by Perfluoro-cis-2-n-butyl-3-n-propyloxaziridin" *Org. Lett.* (1999) 1(2):281-284.
Asensio, G., et al., "Regioselective Oxyfunctionalization of Unactivated Tertiary and Secondary C-H Bonds of Alkylamines by Methyl(trifluoromethyl)dioxirane in Acid Medium" *J. Am. Chem. Soc.* (1993) 115:7250-7253.
Bioreversible Carriers in Drug Design: Theory and Application 13-21 and Table of Contents (E. B. Roche ed., Pergamon Press New York 1987).
Bunker et al., "Scalable Synthesis of 1-Bicyclo[1.1.1]pentylamine via a Hydrohydrazination Reaction" *Org. Lett.* (2011) 13:4746-4748.
Bunz et al., "Bridgehead-Coupled Bicyclo[1.1.1]pentanes: Synthesis and Structure" *Chemische Berichte* (1988) 121:1785-1790.
Cao K. et al., "Carbon-14 labeling of Saxagliptin (BMS-477118)" *J Label Compd Radiopharm* (2007) 50:1224-1229.
CAS Reg. No. 1046861-73-7, entered Sep. 5, 2008.
CAS Reg. No. 1219538-79-0, entered Apr. 19, 2010.
CAS Reg. No. 1219538-81-4, entered Apr. 19, 2010.
CAS Reg. No. 1219538-83-6, entered Apr. 19, 2010.
Contreras, R.H. et al., "Experimental and DFT studies on the transmission mechanisms of analogous NMR $J_{CH}$ and $J_{cc}$ couplings in 1-X- and 1-X-3-methylbicyclo[1.1.1]-pentanes" *Magn. Reson. Chem.* (2007) 45:572-577.
Contreras et al., "Experimental and Theoretical Study of Hyperconjugative Interaction Effects on NMR $^1J_{CH}$ Scalar Couplings" J. Phys. Chem. A (2006) 110:4266-4275.
Dasgupta A., et al., "Interaction of White and Pink Grapefruit Juice with Acetaminophen (Paracetamol) In Vivo in Mice" *J. Med. Food* (2008) 11(4):795-798.
Design of Prodrugs (Hans Bundgaard ed., Elsevier 1985) Table of Contents only.
Fluck, E., "New Notations in the Periodic Table" Pure & Applied Chemistry (1988) 60(3):432-436.
Gasper et al., "Cobalt Catalyzed Functionalization of Unactivated Alkenes: Regioselective Reductive C-C Bond Forming Reactions" *J. Am. Chem. Soc.* (2009) 131:13214-13215.
Gleiter et al., "The Biocyclo[1.1.1]pentane Framework—an Excellent Relay for η/σConjugation" Angew. Chem. Int. Ed. Engl. (1990) 29(4):413-415.
Hassner, A. "e-EROS Encyclopedia of Reagents for Organic Chemistry" (2005) 1-6 (John Wiley & Sons, Ltd., Chichester) (RN 351882-60-5 and RN351882-61-6).
Henry, J., "Future Basic Science Directions Into Mechanisms of Neuropathic Pain" Orofac. Pain (2004) 18:306-310.
IUPAC Periodic Table of the Elements (2011).
Janecki, T., et al., "[n]Staffanes with Terminal Nitrile and Isonitrile Functionalities and their Metal Complexes" *Collect. Czech. Chem. Commun.* (1993) 83:89-104.
Jasys, V. J., et al., "Preparation of Fluoroadamantane Acids and Amines: Impact of Bridgehead Fluorine Substitution on the Solution- and Solid-State Properties of Functionalized Adamantanes" *J. Am. Chem. Soc.* (2000) 122:466-473.

(56) References Cited

OTHER PUBLICATIONS

Khusnutdinov, R. I., et al., "Selective Hydroxylation of Adamantane and Its Derivatives" *Russian Journal of Organic Chemistry* (2009) 45(8):1137-1142.

Komiya, N., et al., "Ruthenium-catalysed oxidation of alkanes with peracetic acid in trifluoroacetic acid: ruthenium as an efficient catalyst for the oxidation of unactivated C-H bonds" *Chem. Commun.* (2001):65-66.

Lee, I., et al., "Effects of Different Concentrations and Volumes of Formalin on Pain Response in Rats" (2000) Anaesthesiologica Sinica, 38:59-64.

Lee, S. et al., "Chemospecific Chromium[VI] Catalyzed Oxidation of C-H Bonds at 40° C" *J. Am. Chem. Soc.* (2002) 124:13978-13979.

Levin et al., "Bicyclo[1.1.1]pentanes, [n]Staffanes, [1.1.1]Propellanes, and Tricyclo[2.1.0.0$^{2,5}$]pentanes" (2000) *Chem. Rev.* 100:169-234.

Linz, T., et al., "Oxidation of Non-Activated C-H Bonds in Hydrocarbons and Steroids" *Tetrahedron Letters* (1987) 28(52):6581-6582.

McNeill, E. et al., "Ruthenium-Catalyzed Hydroxylation of Unactivated Tertiary C-H Bonds" *J. Am. Chem. Soc.* (2010) 132:10202-10204.

McNeill, E. et al., "Catalytic C-H oxidation by a triazamacrocyclic ruthenium complex" *Chem. Sci.* (2012) 3:1810-1813.

Onomura, O., et al., "Efficient Oxidation of Adamantanes by Sodium Nitrite with Molecular Oxygen in Trifluoroacetic Acid" *Synlett*, (2006) 15:2415-2418.

Pätzel et al., "3-Aminobicyclo[1.1.1]pentane-1-carboxylic Acid Derivatives: Synthesis and Incorporation into Peptides" *Eur. J. Org. Chem.* (2004) 2004(3):493-498.

Pritz, S., et al., "Synthesis of a chiral amino acid with bicycle[1.1.1]pentane moiety and its incorporation into linear and cyclic antimicrobial peptides" *Org. Biomed. Chem.* (2007) 5:1789-1794.

Pro-drugs as Novel Delivery Systems (T. Higuchi and V. Stella eds., vol. 14 A.C.S. Symposium Series, American Chemical Society 1975) Table of Contents and Forward only.

Shmailov, A., et al., "Synthesis of functionalized 5-(3-R-1-admantyl)uracils and related compounds" *Tetrahedron* (2010) 66:3058-3064.

Shmailov, A., et al., "First synthesis of α-(3-R-1-adamantyl)sulfoacetic acids and their derivatives" *Tetrahedron* (2012) 68:4765-4772.

Siegers, C.P., "Relations between Hepatotoxicity and Pharmacokinetics of Paracetamol in Rats and Mice" *Pharmacology* (1978) 16:273-278.

Sorochinsky A. E., et al., "Regioselective Oxyfunctionalization of Bridgehead Adamantane Derivatives" *Tetrahedron* (1997) 53(7):5995-6000.

Stepan, A., et al., "Application of the Bicyclo[1.1.1]pentane Motif a Nonclassical Phenyl Ring Bioisostere in the Design of a Potent and Orally Active γ-Secretase Inhibitor" *J. Med. Chem.* (2012) 55:3414-3424.

Sufka, K., et al., "Scoring the mouse formalin test: validation study" *Eur. J. Pain* (1998) 2:351-358.

Tanemura, K., et al., "Formation of adamantan-1-ols by the reactions of adamantanes with 2,3-dichloro-5,6-dicyano-p-benzoquinone (DDQ) in trifluoromethanesulfonic acid" *J. Chem. Soc., Perkin Trans.* 1 ( 2001) 1: 3230-3231.

Tjølsen, A., et al, "The formalin test: an evaluation of the method" (1992) Pain, 51:5-17.

Toops et al., "Efficient Synthesis of 1-(Trialkylstannyl)- and 1-(Triarylstannyl)bicyclo[1.1.1]pentanes" *J. Org. Chem.* (1993) 58:6505-6508.

Vahidy, W., et al, "Effects of intracerebroventricular injections of free fatty acids, lysophospholipids, or platelet activating factor in a mouse model of orofacial pain" (2006) Exp. Brain Res. 174:781-785.

Vissers, K., et al, "Pharmacological correlation between the formalin test and the neuropathic pain behavior in different species with chronic construction injury" Pharmacology, Biochemistry and Behavior (2006) 84:479-486.

Wang et al., "The Oral Analgesic Efficacy of Bicifadine Hydrochloride in Postoperative Pain" J. Clin. Pharm. (1982) 22(4):160-164.

Wanka, L., et al., "γ-Aminoadamantanecarboxylic Acids Through Direct C-H Bond Amidations" *Eur. J. Org. Chem.* (2007) 2007(9):1474-1490.

Waser et al., "Hyrdazines and Azides via the Metal-Catalyzed Hydrohydrazination and Hydroazidation of Olefins" *J. Am. Chem. Soc.* (2006) 128:11693-11712.

Wheeler-Aceto, H., et al., "Standardization of the rat paw formalin test for the evaluation of analogesics" Psychopharmacology (Berl) (1991) 104:35-44.

Wiberg et al., "Reactions of [1.1.1]Propellane" J. Am. Soc. (1990) 112:2194-2216.

Zarubaev V. V. et al., "Synthesis of anti-viral activity of azolo-admantanes against influenza A virus" *Bioorganic & Medicinal Chemistry* (2010) 18:839-848.

Zehnder et al., "Optimization of Potent, Selective, and Orally Bioavailable Pyrrolodinopyrimidine- Containing Inhibitors of Heat Shock Protein 90. Identification of Development Candidate 2-Amino-4{4-chloro-2-[2-(4-fluoro-1H-pyrazol-1-ypethoxy]-6-methylphenyl}-N-(2,2-difluoropropyl)-5,7-dihydro-6H-pyrrolo[3,4-d]pyrimidine-6-carboxamide" J. Med. Chem. (2011) 54:3368-3385.

International Search Report and Written Opinion dated Jan. 28, 2016 for PCT Application No. PCT/US2015/050275, filed Sep. 15, 2015.

International Report on Patentability dated Mar. 30, 2017 for PCT Application No. PCT/US2015/050275, filed Sep. 15, 2015.

Extended European Search Report dated Apr. 19, 2018 for EP Application No. 15842230.3, filed Sep. 15, 2015.

Office Action dated Sep. 30, 2020 for CN Application No. 201580061363.9, filed Sep. 15, 2015.

Alekseenko, A.N., et al., "An improved synthesis of 2-, 3-, and 4-(trifluoromethyl) cyclohexylamines" Synthesis (2012) 44:2739-2742.

Barone et al., "NMR $^3J(C_1,H_3)$ Couplings in 1-X-Bicyclo[1.1.1]Pentanes FPT-DFT and NBO Studies of Hyperconjugative Interactions and Heavy Atom Substituent Effects" J. Comp. Chem. (2001) 22(14):1615-1621.

CAS Reg. No. 1230133-71-7, Entered Jul. 11, 2010.
CAS Reg. No. 130682-55-2, Entered Nov. 30, 1990.
CAS Reg. No. 130974-28-6, Entered Dec. 14, 1990.
CAS Reg. No. 136399-14-9, Entered Sep. 28, 1991.

Della, E.W., "Fluorine-19 chemical shifts in saturated systems" Australian Journal of Chemistry, (1970) 23(12):2421-2426.

Gudipati, A. "Infrared spectra of [n] staffanes" J. Phys. Chem. 96.25 (1992): 10165-10176.

Radchenko, D.S., et al., "Cyclobutane-Derived Diamines: Synthesis and Molecular Structure" Journal of Organic Chemistry (2010) 75:5941-5952.

Whitney, J.G., et al, "Antiviral agents. I. Bicyclo[2.2.2]octan- and -oct-2-enamines". Journal of Medicinal Chemistry (1970) 13(2):254-260.

Office Action dated Sep. 30, 2016 for U.S. Appl. No. 14/855,102, filed Sep. 15, 2015.

Office Action dated May 5, 2017 for U.S. Appl. No. 14/855,102, filed Sep. 15, 2015.

Office Action dated Jul. 3, 2018 for U.S. Appl. No. 14/855,102, filed Sep. 15, 2015.

Office Action dated Jun. 15, 2020 for JP Application No. 2017-514844, filed Sep. 15, 2015.

Office Action dated Feb. 4, 2020 for Argentine Application No. 20150102980, filed Sep. 17, 2015.

Office Action dated Feb. 7, 2020 for CN Application No. 201580061363.9, filed Sep. 15, 2015.

Communication dated Oct. 8, 2019 for EP Application No. 15842230.3, filed Sep. 15, 2015.

\* cited by examiner

BICYCLIC COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. application Ser. No. 14/855,102, filed Sep. 15, 2015 and 62/051,760, filed Sep. 17, 2014.

BACKGROUND

Field

The present application relates to the fields of chemistry, biochemistry and medicine. More particularly, disclosed herein are bicyclopentane compounds. Also disclosed herein are methods of using bicyclopentane compounds as an analgesic.

Description

Nonsteroidal anti-inflammatory compounds, or NSAIDs, are an extremely useful group of small molecule drugs, typified by acetylsalicylic acid, ibuprofen and naproxen. These are often sold without prescription, and are variously used to treat pain, inflammation, and fever. However, NSAIDs can have undesirable side effects, including gastric upset and/or gastric bleeding.

Acetaminophen, also known as paracetamol or APAP, is also an effective pain reliever often sold over the counter (without prescription). Although it shares analgesic and antipyretic properties with NSAIDs, it has only weak anti-inflammatory properties, and is thus not an NSAID. Unlike many NSAIDs, acetaminophen does not cause gastric upset or bleeding in prescribed doses. Thus, it is an extremely useful drug for those wishing analgesia without adverse gastric side effects.

Acetaminophen has the structure:

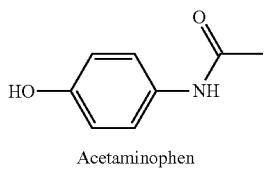

Acetaminophen

Acetaminophen is often combined with other drugs for relief of symptoms of influenza and the common cold, among other indications. It is particularly useful in combination with opioid analgesics, where it exhibits synergistic analgesic properties and allows patients to achieve adequate pain relief with lower doses of opioids. The most widely prescribed drug in the United States is a combination of acetaminophen and hydrocodone, with over 130 million prescriptions in the year 2010. Other acetaminophen-opioid combinations, including combinations with oxycodone, are also widely prescribed.

Acetaminophen poisoning is the most common cause of acute liver failure in the Western world, and acetaminophen accounts for the most drug overdoses in the English-speaking world. Acetaminophen is metabolized to form N-acetyl-p-benzoquinoneimine (NAPQI), which depletes glutathione in the liver, and if the glutathione is sufficiently depleted, as is the case with an acetaminophen overdose, the NAPQI metabolite injures hepatocytes leading to acute liver failure and often death. The acetaminophen-opioid combination drugs are commonly implicated in such toxicity, for various reasons. First, patients might not recognize that the prescribed pain relievers contain acetaminophen, and may supplement with acetaminophen if pain relief is inadequate. Second, continued administration of opioids can lead to tolerance and the need for increased dosages to obtain a comparable opioid effect, and users or abusers of the combination drugs may exceed safe dosages of acetaminophen as a consequence.

This has led the U.S. FDA to seek reduced amounts of acetaminophen in the opioid combination drugs and has also led an FDA advisory panel to recommend banning such drugs all together. Although the acetaminophen-opioid drugs remain on the market, there is a strong need for a less toxic replacement without the same hepatotoxicity risks.

SUMMARY

Some embodiments described herein relate to a compound of Formula (I), or a pharmaceutically acceptable salt thereof. Other embodiments described herein relate to a compound of Formula (II), or a pharmaceutically acceptable salt thereof.

Some embodiments described herein related to a pharmaceutical composition that can include an effective amount of a compound of Formula (I), or a pharmaceutically acceptable salt thereof. Other embodiments described herein related to a pharmaceutical composition that can include an effective amount of a compound of Formula (II), or a pharmaceutically acceptable salt thereof.

Some embodiments described herein related to using a compound of Formula (I), or a pharmaceutically acceptable salt thereof, in the preparation of a medicament for reducing or at least partially preventing pain and/or fever. Other embodiments described herein related to a method for reducing or at least partially preventing pain and/or fever that can include administering an effective amount of a compound of Formula (I), or a pharmaceutically acceptable salt thereof, to a subject in need thereof. Still other embodiments described herein related to a method for reducing or at least partially preventing pain and/or fever that can include contacting a cell in the central and/or peripheral nervous system of a subject with an effective amount of a compound of Formula (I), or a pharmaceutically acceptable salt thereof, to a subject in need thereof. Yet still other embodiments described herein related to the use of a compound of Formula (I), or a pharmaceutically acceptable salt thereof, for reducing or at least partially preventing pain and/or fever.

Some embodiments described herein related to using a compound of Formula (II), or a pharmaceutically acceptable salt thereof, in the preparation of a medicament for reducing or at least partially preventing pain and/or fever. Other embodiments described herein related to a method for reducing or at least partially preventing pain and/or fever that can include administering an effective amount of a compound of Formula (II), or a pharmaceutically acceptable salt thereof, to a subject in need thereof. Still other embodiments described herein related to a method for reducing or at least partially preventing pain and/or fever that can include contacting a cell in the central and/or peripheral nervous system of a subject with an effective amount of a compound of Formula (I), or a pharmaceutically acceptable salt thereof, to a subject in need thereof. Yet still other embodiments described herein related to the use of a compound of Formula (II), or a pharmaceutically acceptable salt thereof, for reducing or at least partially preventing pain and/or fever.

DETAILED DESCRIPTION

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heterocyclyl, aryl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, sulfenyl, sulfinyl, sulfonyl, haloalkyl, haloalkoxy, an amino, a mono-substituted amino group and a di-substituted amino group.

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

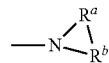

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted.

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Typical mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; and examples of bridged cycloalkyl groups are bicyclo[1.1.1]pentyl, adamantanyl and norbornanyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. Cycloalkynyl groups can contain 8 to 30 atoms in the ring(s), 8 to 20 atoms in the ring(s) or 8 to 10 atoms in the ring(s). When composed of two or more rings, the rings may be joined together in a fused, bridged or spiro fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused or spiro fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group and/or by substituting both hydrogens on the same carbon with a cycloalkyl group (e.g.,

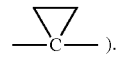

).

As used herein, the term "hydroxy" refers to a —OH group.

As used herein, "alkoxy" refers to the formula —OR wherein R is an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

A "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "—OC(=O)N (R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N (R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N(R_AR_B)" group in which R_A and R_B can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N(R_A)—" group in which R and R_A can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N(R_AR_B)" group in which R_A and R_B can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N(R_A)—" group in which R and R_A can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

An "S-sulfonamido" group refers to a "—SO_2N(R_AR_B)" group in which R_A and R_B can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "RSO_2N(R_A)—" group in which R and R_A can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

An "isocyanato" group refers to a "—NCO" group.

A "thiocyanato" group refers to a "—CNS" group.

An "isothiocyanato" group refers to an "—NCS" group.

A "nitro" group refers to an "—NO_2" group.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO_2R" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The term "amino" as used herein refers to a —NH_2 group.

A "mono-substituted amino" group refers to a "—NHR" group in which R can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A mono-substituted amino may be substituted or unsubstituted. Examples of mono-substituted amino groups include, but are not limited to, —NH(methyl), —NH(phenyl) and the like.

A "di-substituted amino" group refers to a "—NR_AR_B" group in which R_A and R_B can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A di-substituted amino may be substituted or unsubstituted. Examples of di-substituted amino groups include, but are not limited to, —N(methyl)_2, —N(phenyl)(methyl), —N(ethyl)(methyl) and the like.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), a sulfuric acid, a nitric acid and a phosphoric acid (such as 2,3-dihydroxypropyl dihydrogen phosphate). Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, trifluoroacetic, benzoic, salicylic, 2-oxopentanedioic, or naphthalenesulfonic acid. Pharmaceutical salts can also be obtained by reacting a compound with a base to form a salt such as an ammonium salt, an alkali metal salt, such as a sodium, a potassium or a lithium salt, an alkaline earth metal salt, such as a calcium or a magnesium salt, a salt of a carbonate, a salt of a bicarbonate, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine. For compounds of Formulae (I) and/or (II), those skilled in the art understand that when a salt is formed by protonation of a nitrogen-based group (for example, NH$_2$), the nitrogen-based group can be associated with a positive charge (for example, NH$_2$ can become NH$_3^+$) and the positive charge can be balanced by a negatively charged counterion (such as Cl$^-$).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

Compounds

Some embodiments disclosed herein relate to a compound of Formula (I), or a pharmaceutically acceptable salt thereof:

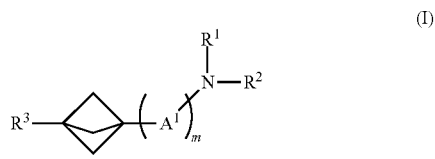

wherein: R$^1$ can be selected from H (hydrogen), D (deuterium), a substituted or unsubstituted C$_{1-6}$ alkyl and a substituted or unsubstituted C$_{1-6}$ haloalkyl; R$^2$ can be H (hydrogen) or C(=O)R$^{2A}$; R$^{2A}$ can be selected from H (hydrogen), D (deuterium), a substituted or unsubstituted C$_{1-30}$ alkyl, a substituted or unsubstituted C$_{2-30}$ alkenyl, a substituted or unsubstituted C$_{2-30}$ alkynyl, a substituted or unsubstituted C$_{3-30}$ cycloalkyl, a substituted or unsubstituted C$_{3-30}$ cycloalkenyl, a substituted or unsubstituted C$_{8-30}$ cycloalkynyl, a substituted or unsubstituted C$_{6-30}$ aryl, a substituted or unsubstituted heteroaryl, a substituted or unsubstituted heterocyclyl, a substituted or unsubstituted aryl($C_{1-6}$ alkyl), a substituted or unsubstituted heteroaryl($C_{1-6}$ alkyl), a substituted or unsubstituted heterocyclyl($C_{1-6}$ alkyl) and a substituted or unsubstituted $C_{1-8}$ haloalkyl; $R^3$ can be selected from H (hydrogen), D (deuterium), halo, hydroxy, a substituted or unsubstituted $C_{1-8}$ alkyl, a substituted or unsubstituted $C_{2-8}$ alkenyl, a substituted or unsubstituted $C_{2-8}$ alkynyl, a substituted or unsubstituted $C_{3-20}$ cycloalkyl, a substituted or unsubstituted $C_{3-20}$ cycloalkenyl, a substituted or unsubstituted $C_{8-20}$ cycloalkynyl, a substituted or unsubstituted $C_{6-20}$ aryl, a substituted or unsubstituted heteroaryl, a substituted or unsubstituted heterocyclyl, a substituted or unsubstituted aryl($C_{1-6}$ alkyl), a substituted or unsubstituted heteroaryl($C_{1-6}$ alkyl), a substituted or unsubstituted heterocyclyl($C_{1-6}$ alkyl), a substituted or unsubstituted $C_{1-8}$ haloalkyl and a substituted or unsubstituted sulfonyl; $A^1$ can be $CR^4R^5$; $R^4$ and $R^5$ can be independently selected from H (hydrogen), D (deuterium), unsubstituted $C_{1-8}$ alkyl and an unsubstituted $C_{1-6}$ haloalkyl, or $R^4$ and $R^5$ can be taken together to form an optionally substituted $C_{3-6}$ cycloalkyl; and m can be 0, 1, 2 or 3.

In some embodiments, $R^1$ can be H (hydrogen). In other embodiments, $R^1$ can be D (deuterium). In still other embodiments, $R^1$ can be a substituted $C_{1-6}$ alkyl. In yet still other embodiments, $R^1$ can be an unsubstituted $C_{1-6}$ alkyl. For example, $R^1$ can be methyl. Other examples of $C_{1-6}$ alkyl groups include ethyl, n-propyl, iso-propyl, n-butyl, iso-butyl, tert-butyl, pentyl (straight and branched) and hexyl (straight and branched). In some embodiments, $R^1$ can be a substituted $C_{1-6}$ haloalkyl. In other embodiments, $R^1$ can be an unsubstituted $C_{1-6}$ haloalkyl. Examples of suitable $C_{1-6}$ haloalkyls include, but are not limited to, $CF_3$, $CH_2CF_3$, $CH_2CHF_2$ and $CH_2CH_2F$.

In some embodiments, $R^2$ can be H. When $R^2$ is H, $NR^1R^2$ of Formula (I) can be an amino or a mono-substituted amine group that can be attached to the bicyclopentane ring directly or through an optionally substituted alkylene group. In some embodiments, $R^2$ can be an amino group directly attached to the bicyclopentane ring. In some embodiments, $R^2$ can be an amino group attached to the bicyclopentane ring through an optionally substituted methylene. In other embodiments, $R^2$ can be an amino group attached to the bicyclopentane ring through an optionally substituted ethylene. In still other embodiments, $R^2$ can be an amino group attached to the bicyclopentane ring through an optionally substituted propylene. In some embodiments, $R^2$ can be a mono-substituted group directly attached to the bicyclopentane ring. In other embodiments, $R^2$ can be a mono-substituted group attached to the bicyclopentane ring through an optionally substituted methylene. In still other embodiments, $R^2$ can be a mono-substituted group attached to the bicyclopentane ring through an optionally substituted ethylene. In yet still other embodiments, $R^2$ can be a mono-substituted group attached to the bicyclopentane ring through an optionally substituted propylene.

In some embodiments, $R^2$ can be $C(=O)R^{2A}$. When $R^2$ is $C(=O)R^{2A}$, $NR^1R^2$ of Formula (I) can be an optionally substituted N-amido group that can be attached to the bicyclopentane ring directly or through an optionally substituted alkylene group. In some embodiments, $R^2$ can be an N-amido group directly attached to the bicyclopentane ring. In other embodiments, $R^2$ can be an N-amido group attached to the bicyclopentane ring through an optionally substituted methylene. In still other embodiments, $R^2$ can be an N-amido group attached to the bicyclopentane ring through an optionally substituted ethylene. In yet still other embodiments, $R^2$ can be an N-amido group attached to the bicyclopentane ring through an optionally substituted propylene. The alkylene group can be substituted or unsubstituted and can include one or more deuteriums.

When $R^2$ is $C(=O)R^{2A}$, $R^{2A}$ can be a variety of groups. In some embodiments, $R^{2A}$ can be H (hydrogen). In other embodiments, $R^{2A}$ can be D (deuterium). In still other embodiments, $R^{2A}$ can be a substituted $C_{1-30}$ alkyl. In yet still other embodiments, $R^{2A}$ can be an unsubstituted $C_{1-30}$ alkyl. The alkyl group can be a long alkyl having 1 to 30 carbons, a medium alkyl having 1 to 12 carbon atoms or a lower alkyl having 1 to 6 carbon atoms. Examples of lower alkyl groups include, methyl, ethyl, n-propyl, iso-propyl, n-butyl, iso-butyl, a tert-butyl, pentyl (straight and branched) and hexyl (straight and branched). In some embodiments, $R^{2A}$ can be an unsubstituted alkyl having 8 to 26 carbon atoms. Examples of unsubstituted $C_{1-30}$ alkyls include, but are not limited to, —$(CH_2)_6CH_3$, —$(CH_2)_8CH_3$, —$(CH_2)_{10}CH_3$, —$(CH_2)_{12}CH_3$, —$(CH_2)_{14}CH_3$, —$(CH_2)_{16}CH_3$, —$(CH_2)_{18}CH_3$, —$(CH_2)_{20}CH_3$, —$(CH_2)_{22}CH_3$ and —$(CH_2)_{24}CH_3$.

In some embodiments, $R^{2A}$ can be a substituted $C_{2-30}$ alkenyl. In other embodiments, $R^{2A}$ can be an unsubstituted $C_{2-30}$ alkenyl. In still other embodiments, $R^{2A}$ can be a substituted $C_{2-30}$ alkynyl. In yet still other embodiments, $R^{2A}$ can be an unsubstituted $C_{2-30}$ alkynyl. Similar to alkyls, alkenyls and alkynyls can be a long alkenyl and/or alkynyl having 2 to 30 carbons, a medium alkenyl and/or alkynyl having 2 to 12 carbon atoms or a lower alkenyl and/or alkynyl having 2 to 6 carbon atoms. In some embodiments, $R^{2A}$ can be an unsubstituted alkenyl having 14 to 22 carbon atoms. Examples of unsubstituted $C_{2-30}$ alkenyls include, but are not limited to, —$(CH_2)_7CH=CH(CH_2)_3CH_3$, —$(CH_2)_7CH=CHCH_2CH=CH(CH_2)_4CH_3$, —$(CH_2)_7CH=CH(CH_2)_7CH_3$, —$(CH_2)_7CH=CHCH_2CH=CH(CH_2)_4CH_3$, —$(CH_2)_7CH=CH(CH_2)_7CH_3$, —$(CH_2)_7CH=CHCH_2CH=CHCH_2CH=CHCH_2CH_3$, —$(CH_2)_9CH=CH(CH_2)_5CH_3$, —$(CH_2)_3CH=CHCH_2CH=CHCH_2CH=CH(CH_2)_4CH_3$, —$(CH_2)_{11}CH=CH(CH_2)_7CH_3$, —$(CH_2)_3CH=CHCH_2CH=CHCH_2CH=CHCH_2CH=CHCH_2CH_3$, —$(CH_2)_4CH=CHCH(CH_3)_2$ and —$(CH_2)_2CH=CHCH_2CH=CHCH_2CH=CHCH_2CH=CHCH_2CH_3$.

In some embodiments, $R^{2A}$ can be the aliphatic tail of a saturated or an unsaturated fatty acid. As an example, $R^{2A}$ can be the aliphatic tail of caprylic acid (HOO$\underline{C}$($\boldsymbol{CH_2})_6\boldsymbol{CH_3}$). In this example of caprylic acid, the aliphatic tail is bolded and italicized. When the saturated or an unsaturated fatty acid becomes part of a compound of Formula (I), the carbon of the carboxylic acid of the saturated or an unsaturated fatty acid becomes the carbon that is bold and underlined carbon of $\underline{C}(=O)R^{2A}$. For example, when $R^{2A}$ is the aliphatic tail of caprylic acid, the compound of Formula (I) can have the following structure:

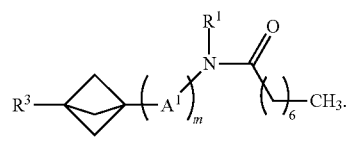

A non-limiting list of suitable saturated or an unsaturated fatty acids are myristoleic acid, palmitoleic, sapienic acid, linoleic acid, oleic acid, linoleiaidic acid, elaidic acid, alpha-linolenic acid, vaccenic acid, arachidonic acid, erucic acid, eicosapentaenoic acid, (E)-8-methylnon-6-enoic acid, docosahexaenoic acid, caprylic acid, capric acid, lauric acid, myristic acid, palmitic acid, stearic acid, arachidic acid, behenic acid, lignoceric acid and cerotic acid.

Cyclic groups can also be present at $R^{2A}$. In some embodiments, $R^{2A}$ can be a substituted $C_{3-30}$ cycloalkyl. In other embodiments, $R^{2A}$ can be an unsubstituted $C_{3-30}$ cycloalkyl. In still other embodiments, $R^{2A}$ can be a substituted $C_{3-30}$ cycloalkenyl. In yet still other embodiments, $R^{2A}$ can be an unsubstituted $C_{3-30}$ cycloalkenyl. In some embodiments, $R^{2A}$ can be a substituted $C_{8-30}$ cycloalkynyl. In some embodiments, $R^{2A}$ can be an unsubstituted $C_{8-30}$ cycloalkynyl. The number of carbon ring atoms of a cycloalkyl and a cycloalkenyl can vary. In some embodiments, the number of carbon ring atoms of a cycloalkyl and a cycloalkenyl can be 3 to 30, 3 to 20, 3 to 10, 3 to 8 or 3 to 6. Likewise, the number of carbon ring atoms of a cycloalkynyl can vary, for example, 8 to 30, 8 to 20 or 8 to 10. The number rings of a cycloalkyl, a cycloalkenyl and a cycloalkynyl can also vary. In some embodiments, a cycloalkyl, a cycloalkenyl and/or a cycloalkynyl can be mono-cyclic. In other embodiments, a cycloalkyl, a cycloalkenyl and a cycloalkynyl can be bi-cyclic or tri-cyclic. As described herein, the rings of a multi-cyclic cycloalkyl, cycloalkenyl and cycloalkynyl can be joined together to form fused ring system, a bridged ring system and/or spiro-connected ring system.

In some embodiments, $R^{2A}$ can be a substituted $C_{6-30}$ aryl. In other embodiments, $R^{2A}$ can be an unsubstituted $C_{6-30}$ aryl. Examples of suitable $C_{6-30}$ aryl groups include, but are not limited to phenyl, naphthyl, anthracenyl and phenanthrene. When $R^{2A}$ is a substituted phenyl, the phenyl ring can be substituted at the ortho, meta and/or para position(s). As described herein, the number of substituent groups present on a substituted aryl group can vary from 1, 2, 3, to 3 or more substituent groups.

Cyclic groups of $R^{2A}$ can also contain one or more heteroatoms. For example, in some embodiments, $R^{2A}$ can be a substituted heteroaryl. In other embodiments, $R^{2A}$ can be an unsubstituted heteroaryl. In some embodiments, $R^{2A}$ can be a substituted or unsubstituted mono-cyclic heteroaryl. In some embodiments, $R^{2A}$ can be a substituted or unsubstituted multi-cyclic heteroaryl, for example, a substituted or unsubstituted bi-cyclic heteroaryl.

In some embodiments, $R^{2A}$ can be a substituted heterocyclyl. In other embodiments, $R^{2A}$ can be an unsubstituted heterocyclyl. In some embodiments, $R^{2A}$ can be a substituted or unsubstituted mono-cyclic heterocyclyl. In some embodiments, $R^{2A}$ can be a substituted or unsubstituted multi-cyclic heterocyclyl (such as a bi-cyclic heterocyclyl). A mono-cyclic heteroaryl and/or a mono-cyclic heterocyclyl can include 5 to 6 ring atoms, and a bi-cyclic heteroaryl and/or a bi-cyclic heterocyclyl can include 9 to 10 ring atoms.

A cyclic group connected via a carbon-based linker can be present as a $R^{2A}$ group. In some embodiments, $R^{2A}$ can be a substituted aryl($C_{1-6}$ alkyl). In other embodiments, $R^{2A}$ can be an unsubstituted aryl($C_{1-6}$ alkyl). As an example, $R^{2A}$ can be a substituted or unsubstituted benzyl. In some embodiments, $R^{2A}$ can be a substituted heteroaryl($C_{1-6}$ alkyl). In other embodiments, $R^{2A}$ can be an unsubstituted heteroaryl ($C_{1-6}$ alkyl). In some embodiments, $R^{2A}$ can be a substituted or unsubstituted mono-cyclic heteroaryl($C_{1-6}$ alkyl). In some embodiments, $R^{2A}$ can be a substituted or unsubstituted multi-cyclic heteroaryl($C_{1-6}$ alkyl), such as a substituted or unsubstituted bi-cyclic heteroaryl($C_{1-6}$ alkyl). In some embodiments, $R^{2A}$ can be a substituted heterocyclyl($C_{1-6}$ alkyl). In other embodiments, $R^{2A}$ can be an unsubstituted heterocyclyl($C_{1-6}$ alkyl). In some embodiments, $R^{2A}$ can be a substituted or unsubstituted mono-cyclic heterocyclyl($C_{1-6}$ alkyl). In some embodiments, $R^{2A}$ can be a substituted or unsubstituted multi-cyclic heterocyclyl($C_{1-6}$ alkyl), for example, a substituted or unsubstituted bi-cyclic heterocyclyl($C_{1-6}$ alkyl).

In some embodiments, $R^{2A}$ can be a substituted $C_{1-8}$ haloalkyl. In other embodiments, $R^{2A}$ can be an unsubstituted $C_{1-8}$ haloalkyl. Examples of suitable $C_{1-8}$ haloalkyls include, but are not limited to, $CF_3$, $CHF_2$, $CH_2F$, $CH_2CF_3$, $CH_2CHF_2$ and $CH_2CH_2F$.

Various groups can also be present for $R^3$. In some embodiments, $R^3$ can be H (hydrogen). In other embodiments, $R^3$ can be D (deuterium). In still other embodiments, $R^3$ can be a halo. For example, $R^3$ can be F (fluoro) or Cl (chloro). In yet still other embodiments, $R^3$ can be hydroxy.

In some embodiments, $R^3$ can be a substituted $C_{1-8}$ alkyl. Various groups can be present on a substituted $C_{1-8}$ alkyl of $R^3$, such as a hydroxy group. In other embodiments, $R^3$ can be an unsubstituted $C_{1-8}$ alkyl. Suitable substituted and unsubstituted $C_{1-8}$ alkyl groups include, methyl, ethyl, n-propyl, iso-propyl, n-butyl, iso-butyl, tert-butyl, pentyl (straight and branched), hexyl (straight and branched), heptyl (straight and branched) and octyl (straight and branched). In some embodiments, $R^3$ can be —$C(CH_3)_2OH$.

In some embodiments, $R^3$ can be a substituted $C_{2-8}$ alkenyl. In other embodiments, $R^3$ can be an unsubstituted $C_{2-8}$ alkenyl. In some embodiments, $R^3$ can be a substituted $C_{2-4}$ alkenyl. In other embodiments, $R^3$ can be an unsubstituted $C_{2-4}$ alkenyl. In some embodiments, $R^3$ can be a substituted $C_{2-8}$ alkynyl. In other embodiments, $R^3$ can be an unsubstituted $C_{2-8}$ alkynyl. In some embodiments, $R^3$ can be a substituted $C_{2-4}$ alkynyl. In other embodiments, $R^3$ can be an unsubstituted $C_{2-4}$ alkynyl.

As with $R^{2A}$, $R^3$ can be a substituted or an unsubstituted cyclic group. In some embodiments, $R^3$ can be a substituted $C_{3-20}$ cycloalkyl. In some embodiments, $R^3$ can be an unsubstituted $C_{3-4}$ cycloalkyl. In other embodiments, $R^3$ can be an unsubstituted $C_{3-20}$ cycloalkyl. The cycloalkyl group can be a mono-cyclic cycloalkyl or a multi-cyclic cycloalkyl group (such as a bi-cyclic cycloalkyl). In some embodiments, $R^3$ can be a substituted $C_{3-20}$ cycloalkenyl. In other embodiments, $R^3$ can be an unsubstituted $C_{3-20}$ cycloalkenyl. Similar to a cycloalkyl group, a cycloalkenyl group can be a mono-cyclic cycloalkenyl or a multi-cyclic cycloalkenyl group (such as a bi-cyclic cycloalkenyl). In some embodiments, $R^3$ can be a substituted $C_{3-20}$ cycloalkynyl. In other embodiments, $R^3$ can be an unsubstituted $C_{3-20}$ cycloalkynyl. A cycloalkynyl can be mono-cyclic, bi-cyclic and/or tri-cyclic. As described herein, when the cycloalkyl, cycloalkenyl and/or cycloalkynyl group includes more than 1 ring, the rings can be joined together in a fused, spiro or bridged fashion. In some embodiments, a cycloalkyl and/or a cycloalkenyl can include 3 to 10 ring carbon atom(s). In other embodiments, a cycloalkyl and/or a cycloalkenyl can include 3 to 6 ring carbon atom(s).

Other examples of suitable cyclic groups include aryl, heteroaryl and heterocyclyl groups. In some embodiments, $R^3$ can be a substituted $C_{6-20}$ aryl. In other embodiments, $R^3$ can be an unsubstituted $C_{6-20}$ aryl. Examples of $C_{6-30}$ aryl groups are described herein. In some embodiments, $R^3$ can be an unsubstituted phenyl. In other embodiments, $R^3$ can be a substituted phenyl. The phenyl ring can be substituted with 1 substituent group, 2 substituents groups or 3 or more substituents. The substituent group(s) can be present at the ortho, meta and/or para position(s). In some embodiments, $R^3$ can be a substituted naphthyl. In other embodiments, $R^3$ can be an unsubstituted naphthyl.

In some embodiments, $R^3$ can be a substituted heteroaryl. In other embodiments, $R^3$ can be an unsubstituted heteroaryl. The number of rings of a heteroary group can vary. For example, in some embodiments, $R^3$ can be a substituted mono-cyclic heteroaryl. In other embodiments, $R^3$ can be an unsubstituted mono-cyclic heteroaryl. The mono-cyclic heteroaryl can include 5 or 6 ring atoms. In still other embodiments, $R^3$ can be a substituted multi-cyclic heteroaryl (for example, a substituted bi-cyclic heteroaryl). In yet still other embodiments, $R^3$ can be an unsubstituted multi-cyclic heteroaryl (for example, an unsubstituted bi-cyclic heteroaryl). The number of ring atoms of a multi-cyclic heteroaryl can vary. For example, a multi-cyclic heteroaryl can include 9 or 10 ring atoms.

In some embodiments, $R^3$ can be a substituted heterocyclyl. In other embodiments, $R^3$ can be an unsubstituted heterocyclyl. As with a heteroaryl group, the number of rings of a heterocyclyl group can vary. In some embodiments, $R^3$ can be a substituted mono-cyclic heterocyclyl. In other embodiments, $R^3$ can be an unsubstituted mono-cyclic heterocyclyl. In still other embodiments, $R^3$ can be a substituted bi-cyclic heterocyclyl. In yet still other embodiments, $R^3$ can be an unsubstituted bi-cyclic heterocyclyl. A mono-cyclic heterocyclyl and a bi-cyclic heterocyclyl can include a various number of ring atoms. A mono-cyclic heterocyclyl can include 5 to 6 ring atoms, and a bi-cyclic heterocyclyl can include 9 to 10 ring atoms.

As described herein, a linker can be used to connect a cyclic group to the bicyclopentane. In some embodiments, $R^3$ can be a substituted aryl($C_{1-6}$ alkyl). In other embodiments, $R^3$ can be an unsubstituted aryl($C_{1-6}$ alkyl). For example, in some embodiments, $R^3$ can be a substituted or unsubstituted benzyl. The phenyl ring of a benzyl group can be substituted with 1 substituent, 2 substituents, 3 substituents or 3 or more substituents.

In some embodiments, $R^3$ can be a substituted heteroaryl ($C_{1-6}$ alkyl). In other embodiments, $R^3$ can be an unsubstituted heteroaryl($C_{1-6}$ alkyl). The heteroaryl ring can be a substituted or unsubstituted mono-cyclic heteroaryl or a substituted or unsubstituted multi-cyclic heteroaryl (such as a bi-cyclic heteroaryl). In still other embodiments, $R^3$ can be a substituted heterocyclyl($C_{1-6}$ alkyl). In other embodiments, $R^3$ can be an unsubstituted heterocyclyl($C_{1-6}$ alkyl). The number of rings of the heterocyclyl or a heterocyclyl ($C_{1-6}$ alkyl) can vary. For example, in some embodiments, $R^3$ can be a substituted mono-cyclic heterocyclyl($C_{1-6}$ alkyl). In other embodiments, $R^3$ can be an unsubstituted mono-cyclic heterocyclyl($C_{1-6}$ alkyl). In still other embodiments, $R^3$ can be a substituted multi-cyclic heterocyclyl($C_{1-6}$ alkyl), for example, a substituted bi-cyclic heterocyclyl($C_{1-6}$ alkyl). In yet still other embodiments, $R^3$ can be an unsubstituted multi-cyclic heterocyclyl($C_{1-6}$ alkyl), for example, an unsubstituted bi-cyclic heterocyclyl($C_{1-6}$ alkyl). As described herein, the number of ring atoms of a heteroaryl ($C_{1-6}$ alkyl) and/or a heterocyclyl($C_{1-6}$ alkyl) can also vary. In some embodiments, a heteroaryl($C_{1-6}$ alkyl) and/or a heterocyclyl($C_{1-6}$ alkyl) can include 5 or 6 ring atoms. In other embodiments, a heteroaryl($C_{1-6}$ alkyl) and/or a heterocyclyl($C_{1-6}$ alkyl) can include 9 or 10 ring atoms.

In some embodiments, $R^3$ can be a substituted $C_{1-8}$ haloalkyl. In other embodiments, $R^3$ can be an unsubstituted $C_{1-8}$ haloalkyl. For example, $R^3$ can be a substituted or an unsubstituted $C_{1-4}$ haloalkyl. In some embodiments, $R^3$ can be $CF_3$. In other embodiments, $R^3$ can be $CHF_2$. In still other embodiments, $R^3$ can be $CH_2F$. In yet still other embodiments, $R^3$ can be $CF_2CH_3$.

In some embodiments, $R^3$ can be a substituted sulfonyl. In other embodiments, $R^3$ can be an unsubstituted sulfonyl. In some embodiments, $R^3$ can be $SO_2R^{++}$, wherein $R^{++}$ can be hydrogen, an optionally substituted $C_{1-6}$ alkyl, an optionally substituted $C_{2-6}$ alkenyl, an optionally substituted $C_{3-6}$ cycloalkyl, an optionally substituted mono-cyclic aryl, an optionally substituted mono-cyclic heteroaryl or an optionally substituted mono-cyclic heterocyclyl. In other embodiments, $R^3$ can be $SO_2R^{++}$, wherein $R^{++}$ can be an unsubstituted $C_{1-6}$ alkyl, an unsubstituted $C_{2-6}$ alkenyl or an unsubstituted $C_{3-6}$ cycloalkyl. In some embodiments, $R^3$ can be $SO_2CH_3$.

A compound of Formula (I) can include a linker group between the bicyclopentane ring and $NR^1R^2$ or the $NR^1R^2$ group can be connected directly to the bicyclopentane ring. In some embodiments, m can be 0. In other embodiments, m can be 1. In still other embodiments, m can be 2. In yet still other embodiments, m can be 3.

In some embodiments, the linker group can be represented by $A^1$, wherein $A^1$ can be $CR^4R^5$. In some embodiments, $R^4$ can be H. In other embodiments, $R^4$ can be D. In still other embodiments, $R^4$ can be an unsubstituted $C_{1-8}$ alkyl. In some embodiments, $R^4$ can be an unsubstituted $C_{1-6}$ haloalkyl, such as $CF_3$, $CHF_2$ or $CH_2F$. In some embodiments, $R^5$ can be H. In other embodiments, $R^5$ can be D. In other embodiments, $R^5$ can be an unsubstituted $C_{1-8}$ alkyl. In some embodiments, $R^5$ can be an unsubstituted $C_{1-6}$ haloalkyl, such as $CF_3$, $CHF_2$ or $CH_2F$. In some embodiments, $R^4$ and $R^5$ can be taken together to form an optionally substituted $C_{3-6}$ cycloalkyl. In some embodiments, one of $R^4$ and $R^5$ can be H, and the other of $R^4$ and $R^5$ can be an unsubstituted $C_{1-8}$ alkyl or an unsubstituted $C_{1-6}$ haloalkyl. In other embodiments, $R^4$ and $R^5$ can be independently an unsubstituted $C_{1-8}$ alkyl or an unsubstituted $C_{1-6}$ haloalkyl. In some embodiments, at least one of $R^4$ and $R^5$ can be D. In some embodiments, $R^4$ and $R^5$ both can be H.

In some embodiments, $R^3$ can be H, F, Cl, an unsubstituted $C_{1-4}$ alkyl, a hydroxy substituted $C_{1-4}$ alkyl, an unsubstituted $C_{1-4}$ haloalkyl, an unsubstituted $C_{3-6}$ cycloalkyl or $SO_2CH_3$, $R^1$ can be H or $CH_3$, and $R^2$ can be H. In some embodiments, $R^3$ can be H, F, Cl, an unsubstituted $C_{1-4}$ alkyl, a hydroxy substituted $C_{1-4}$ alkyl, an unsubstituted $C_{1-4}$ haloalkyl, an unsubstituted $C_{3-6}$ cycloalkyl or $SO_2CH_3$, $R^1$ can be H or $CH_3$, and $R^2$ can be $C(=O)R^{2A}$. In some embodiments, $R^3$ can be H, F, Cl, an unsubstituted $C_{1-4}$ alkyl, a hydroxy substituted $C_{1-4}$ alkyl, an unsubstituted $C_{1-4}$ haloalkyl, an unsubstituted $C_{3-6}$ cycloalkyl or $SO_2CH_3$, $R^1$ can be H or $CH_3$, and $R^2$ can be $C(=O)R^{2A}$, wherein $R^{2A}$ can be an unsubstituted $C_{1-4}$ alkyl or an unsubstituted $C_{2-4}$ alkenyl. In some embodiments, $R^3$ can be H, F, Cl, an unsubstituted $C_{1-4}$ alkyl, a hydroxy substituted $C_{1-4}$ alkyl, an unsubstituted $C_{1-4}$ haloalkyl, an unsubstituted $C_{3-6}$ cycloalkyl or $SO_2CH_3$, $R^1$ can be H or $CH_3$, and $R^2$ can be $C(=O)R^{2A}$, wherein $R^{2A}$ can be an unsubstituted $C_{8-30}$ alkyl or an unsubstituted $C_{8-30}$ alkenyl.

As described herein, the number of substituent groups present on a substituted $R^1$, $R^{2A}$, $R^3$, $R^4$ and/or $R^5$ group can vary from 1, 2, 3, to 3 or more substituents groups. When more than 1 substituent group is present, a group can be the same as at least one other group. Additionally and/or in the alternative, when more than 1 substituent group is present, a group can be different from at least one other group.

A non-limiting list of examples of compounds of Formula (I), or a pharmaceutically acceptable salt, include:

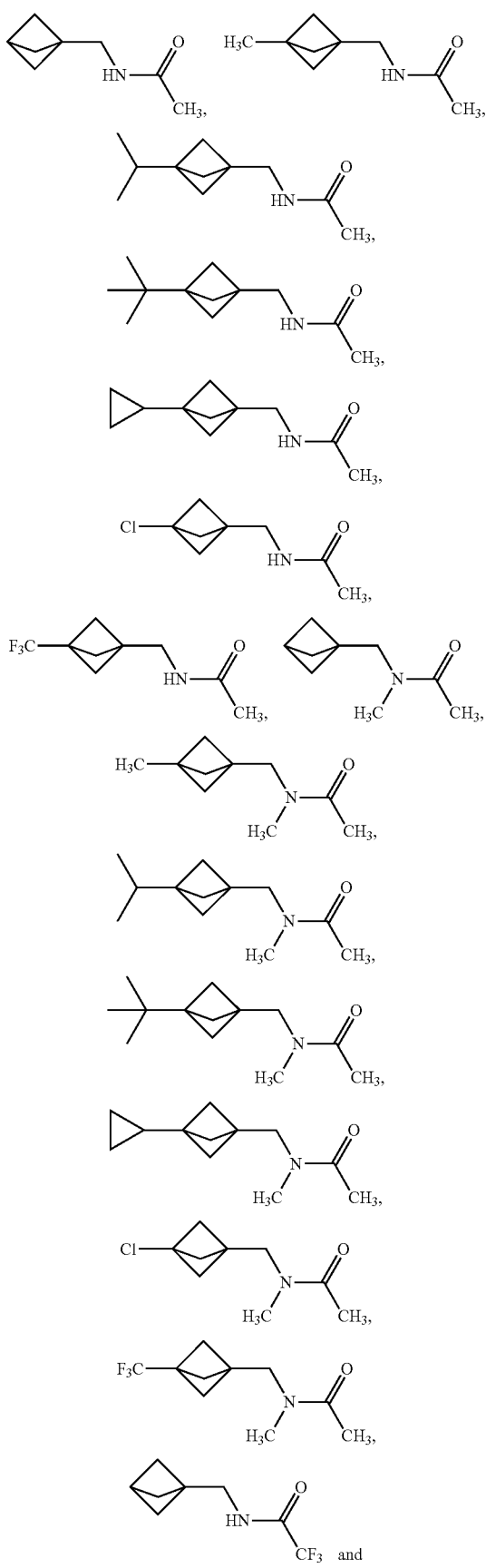

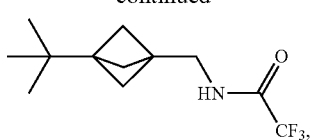

or a pharmaceutically acceptable salt of any of the foregoing.

Additional examples of compounds of Formula (I), or a pharmaceutically acceptable salt, include the following:

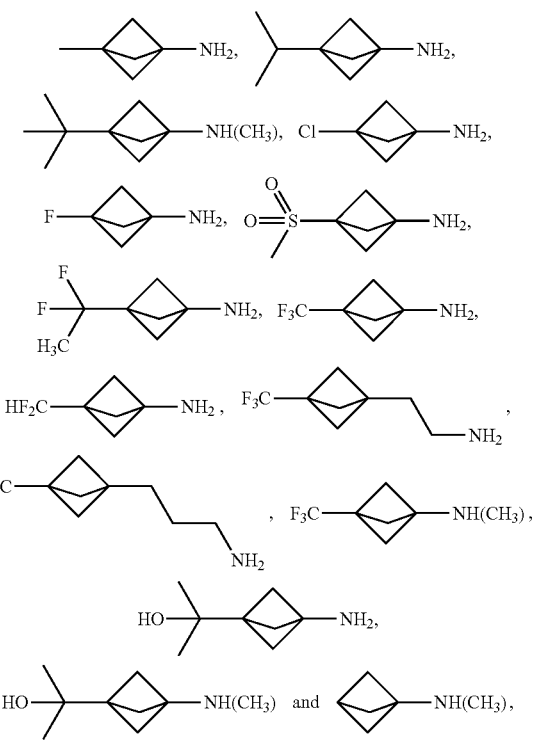

or a pharmaceutically acceptable salt of any of the foregoing.

Further examples of compounds of Formula (I), or a pharmaceutically acceptable salt, include the following:

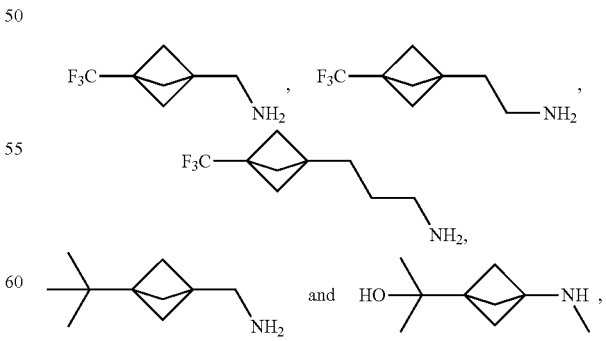

or a pharmaceutically acceptable salt of the foregoing.

Further examples of compounds of Formula (I), or a pharmaceutically acceptable salt, are provided in Table 1.

TABLE 1

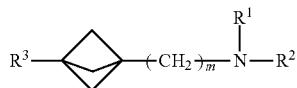

| R¹ | R² | R²⁴ | R³ | m |
|---|---|---|---|---|
| H | C(=O)R²⁴ | —(CH$_2$)$_6$CH$_3$ | H | 0 |
| H | C(=O)R²⁴ | —(CH$_2$)$_8$CH$_3$ | H | 0 |
| H | C(=O)R²⁴ | —(CH$_2$)$_{10}$CH$_3$ | H | 0 |
| H | C(=O)R²⁴ | —(CH$_2$)$_{12}$CH$_3$ | H | 0 |
| H | C(=O)R²⁴ | —(CH$_2$)$_{14}$CH$_3$ | H | 0 |
| H | C(=O)R²⁴ | —(CH$_2$)$_{16}$CH$_3$ | H | 0 |
| H | C(=O)R²⁴ | —(CH$_2$)$_{18}$CH$_3$ | H | 0 |
| H | C(=O)R²⁴ | —(CH$_2$)$_{20}$CH$_3$ | H | 0 |
| H | C(=O)R²⁴ | —(CH$_2$)$_{22}$CH$_3$ | H | 0 |
| H | C(=O)R²⁴ | —(CH$_2$)$_{24}$CH$_3$ | H | 0 |
| H | C(=O)R²⁴ | —(CH$_2$)$_7$CH=CH(CH$_2$)$_3$CH$_3$ | H | 0 |
| H | C(=O)R²⁴ | —(CH$_2$)$_7$CH=CHCH$_2$CH=CH(CH$_2$)$_4$CH$_3$ | H | 0 |
| H | C(=O)R²⁴ | —(CH$_2$)$_7$CH=CH(CH$_2$)$_7$CH$_3$ | H | 0 |
| H | C(=O)R²⁴ | —(CH$_2$)$_7$CH=CHCH$_2$CH=CH(CH$_2$)$_4$CH$_3$ | H | 0 |
| H | C(=O)R²⁴ | —(CH$_2$)$_7$CH=CH(CH$_2$)$_7$CH$_3$ | H | 0 |
| H | C(=O)R²⁴ | —(CH$_2$)$_7$CH=CHCH$_2$CH=CHCH$_2$CH=CHCH$_2$CH$_3$ | H | 0 |
| H | C(=O)R²⁴ | —(CH$_2$)$_9$CH=CH(CH$_2$)$_5$CH$_3$ | H | 0 |
| H | C(=O)R²⁴ | —(CH$_2$)$_3$CH=CHCH$_2$CH=CHCH$_2$CH=CHCH$_2$CH=CH(CH$_2$)$_4$CH$_3$ | H | 0 |
| H | C(=O)R²⁴ | —(CH$_2$)$_{11}$CH=CH(CH$_2$)$_7$CH$_3$ | H | 0 |
| H | C(=O)R²⁴ | —(CH$_2$)$_3$CH=CHCH$_2$CH=CHCH$_2$CH=CHCH$_2$CH=CHCH$_2$CH=CHCH$_2$CH$_3$ | H | 0 |
| H | C(=O)R²⁴ | —(CH$_2$)$_4$CH=CHCH(CH$_3$)$_2$ | H | 0 |
| H | C(=O)R²⁴ | —(CH$_2$)$_2$CH=CHCH$_2$CH=CHCH$_2$CH=CHCH$_2$CH=CHCH$_2$CH=CHCH$_2$CH$_3$ | H | 0 |
| H | C(=O)R²⁴ | —(CH$_2$)$_6$CH$_3$ | CH$_3$ | 0 |
| H | C(=O)R²⁴ | —(CH$_2$)$_8$CH$_3$ | CH$_3$ | 0 |
| H | C(=O)R²⁴ | —(CH$_2$)$_{10}$CH$_3$ | CH$_3$ | 0 |
| H | C(=O)R²⁴ | —(CH$_2$)$_{12}$CH$_3$ | CH$_3$ | 0 |
| H | C(=O)R²⁴ | —(CH$_2$)$_{14}$CH$_3$ | CH$_3$ | 0 |
| H | C(=O)R²⁴ | —(CH$_2$)$_{16}$CH$_3$ | CH$_3$ | 0 |
| H | C(=O)R²⁴ | —(CH$_2$)$_{18}$CH$_3$ | CH$_3$ | 0 |
| H | C(=O)R²⁴ | —(CH$_2$)$_{20}$CH$_3$ | CH$_3$ | 0 |
| H | C(=O)R²⁴ | —(CH$_2$)$_{22}$CH$_3$ | CH$_3$ | 0 |
| H | C(=O)R²⁴ | —(CH$_2$)$_{24}$CH$_3$ | CH$_3$ | 0 |
| H | C(=O)R²⁴ | —(CH$_2$)$_7$CH=CH(CH$_2$)$_3$CH$_3$ | CH$_3$ | 0 |
| H | C(=O)R²⁴ | —(CH$_2$)$_7$CH=CHCH$_2$CH=CH(CH$_2$)$_4$CH$_3$ | CH$_3$ | 0 |
| H | C(=O)R²⁴ | —(CH$_2$)$_7$CH=CH(CH$_2$)$_7$CH$_3$ | CH$_3$ | 0 |
| H | C(=O)R²⁴ | —(CH$_2$)$_7$CH=CHCH$_2$CH=CH(CH$_2$)$_4$CH$_3$ | CH$_3$ | 0 |
| H | C(=O)R²⁴ | —(CH$_2$)$_7$CH=CH(CH$_2$)$_7$CH$_3$ | CH$_3$ | 0 |
| H | C(=O)R²⁴ | —(CH$_2$)$_7$CH=CHCH$_2$CH=CHCH$_2$CH=CHCH$_2$CH$_3$ | CH$_3$ | 0 |
| H | C(=O)R²⁴ | —(CH$_2$)$_9$CH=CH(CH$_2$)$_5$CH$_3$ | CH$_3$ | 0 |
| H | C(=O)R²⁴ | —(CH$_2$)$_3$CH=CHCH$_2$CH=CHCH$_2$CH=CHCH$_2$CH=CH(CH$_2$)$_4$CH$_3$ | CH$_3$ | 0 |
| H | C(=O)R²⁴ | —(CH$_2$)$_{11}$CH=CH(CH$_2$)$_7$CH$_3$ | CH$_3$ | 0 |
| H | C(=O)R²⁴ | —(CH$_2$)$_3$CH=CHCH$_2$CH=CHCH$_2$CH=CHCH$_2$CH=CHCH$_2$CH=CHCH$_2$CH$_3$ | CH$_3$ | 0 |
| H | C(=O)R²⁴ | —(CH$_2$)$_4$CH=CHCH(CH$_3$)$_2$ | CH$_3$ | 0 |
| H | C(=O)R²⁴ | —(CH$_2$)$_2$CH=CHCH$_2$CH=CHCH$_2$CH=CHCH$_2$CH=CHCH$_2$CH=CHCH$_2$CH$_3$ | CH$_3$ | 0 |
| H | C(=O)R²⁴ | —(CH$_2$)$_6$CH$_3$ | CH(CH$_3$)$_2$ | 0 |
| H | C(=O)R²⁴ | —(CH$_2$)$_8$CH$_3$ | CH(CH$_3$)$_2$ | 0 |
| H | C(=O)R²⁴ | —(CH$_2$)$_{10}$CH$_3$ | CH(CH$_3$)$_2$ | 0 |
| H | C(=O)R²⁴ | —(CH$_2$)$_{12}$CH$_3$ | CH(CH$_3$)$_2$ | 0 |
| H | C(=O)R²⁴ | —(CH$_2$)$_{14}$CH$_3$ | CH(CH$_3$)$_2$ | 0 |
| H | C(=O)R²⁴ | —(CH$_2$)$_{16}$CH$_3$ | CH(CH$_3$)$_2$ | 0 |
| H | C(=O)R²⁴ | —(CH$_2$)$_{18}$CH$_3$ | CH(CH$_3$)$_2$ | 0 |
| H | C(=O)R²⁴ | —(CH$_2$)$_{20}$CH$_3$ | CH(CH$_3$)$_2$ | 0 |
| H | C(=O)R²⁴ | —(CH$_2$)$_{22}$CH$_3$ | CH(CH$_3$)$_2$ | 0 |
| H | C(=O)R²⁴ | —(CH$_2$)$_{24}$CH$_3$ | CH(CH$_3$)$_2$ | 0 |
| H | C(=O)R²⁴ | —(CH$_2$)$_7$CH=CH(CH$_2$)$_3$CH$_3$ | CH(CH$_3$)$_2$ | 0 |
| H | C(=O)R²⁴ | —(CH$_2$)$_7$CH=CHCH$_2$CH=CH(CH$_2$)$_4$CH$_3$ | CH(CH$_3$)$_2$ | 0 |
| H | C(=O)R²⁴ | —(CH$_2$)$_7$CH=CH(CH$_2$)$_7$CH$_3$ | CH(CH$_3$)$_2$ | 0 |
| H | C(=O)R²⁴ | —(CH$_2$)$_7$CH=CHCH$_2$CH=CH(CH$_2$)$_4$CH$_3$ | CH(CH$_3$)$_2$ | 0 |
| H | C(=O)R²⁴ | —(CH$_2$)$_7$CH=CH(CH$_2$)$_7$CH$_3$ | CH(CH$_3$)$_2$ | 0 |
| H | C(=O)R²⁴ | —(CH$_2$)$_7$CH=CHCH$_2$CH=CHCH$_2$CH=CHCH$_2$CH$_3$ | CH(CH$_3$)$_2$ | 0 |
| H | C(=O)R²⁴ | —(CH$_2$)$_9$CH=CH(CH$_2$)$_5$CH$_3$ | CH(CH$_3$)$_2$ | 0 |
| H | C(=O)R²⁴ | —(CH$_2$)$_3$CH=CHCH$_2$CH=CHCH$_2$CH=CHCH$_2$CH=CH(CH$_2$)$_4$CH$_3$ | CH(CH$_3$)$_2$ | 0 |
| H | C(=O)R²⁴ | —(CH$_2$)$_{11}$CH=CH(CH$_2$)$_7$CH$_3$ | CH(CH$_3$)$_2$ | 0 |
| H | C(=O)R²⁴ | —(CH$_2$)$_3$CH=CHCH$_2$CH=CHCH$_2$CH=CHCH$_2$CH=CHCH$_2$CH=CHCH$_2$CH$_3$ | CH(CH$_3$)$_2$ | 0 |

TABLE 1-continued

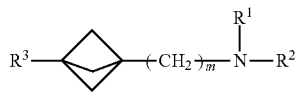

| R¹ | R² | R²⁴ | R³ | m |
|---|---|---|---|---|
| H | C(=O)R²⁴ | —(CH₂)₄CH=CHCH(CH₃)₂ | CH(CH₃)₂ | 0 |
| H | C(=O)R²⁴ | —(CH₂)₂CH=CHCH₂CH=CHCH₂CH=CHCH₂ CH=CHCH₂CH=CHCH₂CH₃ | CH(CH₃)₂ | 0 |
| H | C(=O)R²⁴ | —(CH₂)₆CH₃ | C(CH₃)₃ | 0 |
| H | C(=O)R²⁴ | —(CH₂)₈CH₃ | C(CH₃)₃ | 0 |
| H | C(=O)R²⁴ | —(CH₂)₁₀CH₃ | C(CH₃)₃ | 0 |
| H | C(=O)R²⁴ | —(CH₂)₁₂CH₃ | C(CH₃)₃ | 0 |
| H | C(=O)R²⁴ | —(CH₂)₁₄CH₃ | C(CH₃)₃ | 0 |
| H | C(=O)R²⁴ | —(CH₂)₁₆CH₃ | C(CH₃)₃ | 0 |
| H | C(=O)R²⁴ | —(CH₂)₁₈CH₃ | C(CH₃)₃ | 0 |
| H | C(=O)R²⁴ | —(CH₂)₂₀CH₃ | C(CH₃)₃ | 0 |
| H | C(=O)R²⁴ | —(CH₂)₂₂CH₃ | C(CH₃)₃ | 0 |
| H | C(=O)R²⁴ | —(CH₂)₂₄CH₃ | C(CH₃)₃ | 0 |
| H | C(=O)R²⁴ | —(CH₂)₇CH=CH(CH₂)₃CH₃ | C(CH₃)₃ | 0 |
| H | C(=O)R²⁴ | —(CH₂)₇CH=CHCH₂CH=CH(CH₂)₄CH₃ | C(CH₃)₃ | 0 |
| H | C(=O)R²⁴ | —(CH₂)₇CH=CH(CH₂)₇CH₃ | C(CH₃)₃ | 0 |
| H | C(=O)R²⁴ | —(CH₂)₇CH=CHCH₂CH=CH(CH₂)₄CH₃ | C(CH₃)₃ | 0 |
| H | C(=O)R²⁴ | —(CH₂)₇CH=CH(CH₂)₇CH₃ | C(CH₃)₃ | 0 |
| H | C(=O)R²⁴ | —(CH₂)₇CH=CHCH₂CH=CHCH₂CH=CHCH₂CH₃ | C(CH₃)₃ | 0 |
| H | C(=O)R²⁴ | —(CH₂)₉CH=CH(CH₂)₅CH₃ | C(CH₃)₃ | 0 |
| H | C(=O)R²⁴ | —(CH₂)₃CH=CHCH₂CH=CHCH₂CH=CHCH₂ CH=CH(CH₂)₄CH₃ | C(CH₃)₃ | 0 |
| H | C(=O)R²⁴ | —(CH₂)₁₁CH=CH(CH₂)₇CH₃ | C(CH₃)₃ | 0 |
| H | C(=O)R²⁴ | —(CH₂)₃CH=CHCH₂CH=CHCH₂CH=CHCH₂ CH=CHCH₂CH=CHCH₂CH₃ | C(CH₃)₃ | 0 |
| H | C(=O)R²⁴ | —(CH₂)₄CH=CHCH(CH₃)₂ | C(CH₃)₃ | 0 |
| H | C(=O)R²⁴ | —(CH₂)₂CH=CHCH₂CH=CHCH₂CH=CHCH₂ CH=CHCH₂CH=CHCH₂CH₃ | C(CH₃)₃ | 0 |
| H | C(=O)R²⁴ | —(CH₂)₆CH₃ | cyclopropyl | 0 |
| H | C(=O)R²⁴ | —(CH₂)₈CH₃ | cyclopropyl | 0 |
| H | C(=O)R²⁴ | —(CH₂)₁₀CH₃ | cyclopropyl | 0 |
| H | C(=O)R²⁴ | —(CH₂)₁₂CH₃ | cyclopropyl | 0 |
| H | C(=O)R²⁴ | —(CH₂)₁₄CH₃ | cyclopropyl | 0 |
| H | C(=O)R²⁴ | —(CH₂)₁₆CH₃ | cyclopropyl | 0 |
| H | C(=O)R²⁴ | —(CH₂)₁₈CH₃ | cyclopropyl | 0 |
| H | C(=O)R²⁴ | —(CH₂)₂₀CH₃ | cyclopropyl | 0 |
| H | C(=O)R²⁴ | —(CH₂)₂₂CH₃ | cyclopropyl | 0 |
| H | C(=O)R²⁴ | —(CH₂)₂₄CH₃ | cyclopropyl | 0 |
| H | C(=O)R²⁴ | —(CH₂)₇CH=CH(CH₂)₃CH₃ | cyclopropyl | 0 |
| H | C(=O)R²⁴ | —(CH₂)₇CH=CHCH₂CH=CH(CH₂)₄CH₃ | cyclopropyl | 0 |
| H | C(=O)R²⁴ | —(CH₂)₇CH=CH(CH₂)₇CH₃ | cyclopropyl | 0 |
| H | C(=O)R²⁴ | —(CH₂)₇CH=CHCH₂CH=CH(CH₂)₄CH₃ | cyclopropyl | 0 |
| H | C(=O)R²⁴ | —(CH₂)₇CH=CH(CH₂)₇CH₃ | cyclopropyl | 0 |
| H | C(=O)R²⁴ | —(CH₂)₇CH=CHCH₂CH=CHCH₂CH=CHCH₂CH₃ | cyclopropyl | 0 |
| H | C(=O)R²⁴ | —(CH₂)₉CH=CH(CH₂)₅CH₃ | cyclopropyl | 0 |
| H | C(=O)R²⁴ | —(CH₂)₃CH=CHCH₂CH=CHCH₂CH=CHCH₂ CH=CH(CH₂)₄CH₃ | cyclopropyl | 0 |
| H | C(=O)R²⁴ | —(CH₂)₁₁CH=CH(CH₂)₇CH₃ | cyclopropyl | 0 |
| H | C(=O)R²⁴ | —(CH₂)₃CH=CHCH₂CH=CHCH₂CH=CHCH₂ CH=CHCH₂CH=CHCH₂CH₃ | cyclopropyl | 0 |
| H | C(=O)R²⁴ | —(CH₂)₄CH=CHCH(CH₃)₂ | cyclopropyl | 0 |
| H | C(=O)R²⁴ | —(CH₂)₂CH=CHCH₂CH=CHCH₂CH=CHCH₂ CH=CHCH₂CH=CHCH₂CH₃ | cyclopropyl | 0 |
| H | C(=O)R²⁴ | —(CH₂)₆CH₃ | Cl | 0 |
| H | C(=O)R²⁴ | —(CH₂)₈CH₃ | Cl | 0 |
| H | C(=O)R²⁴ | —(CH₂)₁₀CH₃ | Cl | 0 |
| H | C(=O)R²⁴ | —(CH₂)₁₂CH₃ | Cl | 0 |
| H | C(=O)R²⁴ | —(CH₂)₁₄CH₃ | Cl | 0 |
| H | C(=O)R²⁴ | —(CH₂)₁₆CH₃ | Cl | 0 |
| H | C(=O)R²⁴ | —(CH₂)₁₈CH₃ | Cl | 0 |
| H | C(=O)R²⁴ | —(CH₂)₂₀CH₃ | Cl | 0 |
| H | C(=O)R²⁴ | —(CH₂)₂₂CH₃ | Cl | 0 |
| H | C(=O)R²⁴ | —(CH₂)₂₄CH₃ | Cl | 0 |
| H | C(=O)R²⁴ | —(CH₂)₇CH=CH(CH₂)₃CH₃ | Cl | 0 |
| H | C(=O)R²⁴ | —(CH₂)₇CH=CHCH₂CH=CH(CH₂)₄CH₃ | Cl | 0 |
| H | C(=O)R²⁴ | —(CH₂)₇CH=CH(CH₂)₇CH₃ | Cl | 0 |
| H | C(=O)R²⁴ | —(CH₂)₇CH=CHCH₂CH=CH(CH₂)₄CH₃ | Cl | 0 |
| H | C(=O)R²⁴ | —(CH₂)₇CH=CH(CH₂)₇CH₃ | Cl | 0 |
| H | C(=O)R²⁴ | —(CH₂)₇CH=CHCH₂CH=CHCH₂CH=CHCH₂CH₃ | Cl | 0 |
| H | C(=O)R²⁴ | —(CH₂)₉CH=CH(CH₂)₅CH₃ | Cl | 0 |
| H | C(=O)R²⁴ | —(CH₂)₃CH=CHCH₂CH=CHCH₂CH=CHCH₂ CH=CH(CH₂)₄CH₃ | Cl | 0 |

TABLE 1-continued

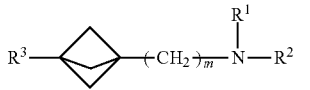

| R$^1$ | R$^2$ | R$^{2A}$ | R$^3$ | m |
|---|---|---|---|---|
| H | C(=O)R$^{24}$ | —(CH$_2$)$_{11}$CH=CH(CH$_2$)$_7$CH$_3$ | Cl | 0 |
| H | C(=O)R$^{24}$ | —(CH$_2$)$_3$CH=CHCH$_2$CH=CHCH$_2$CH=CHCH$_2$CH=CHCH$_2$CH=CHCH$_2$CH$_3$ | Cl | 0 |
| H | C(=O)R$^{24}$ | —(CH$_2$)$_4$CH=CHCH(CH$_3$)$_2$ | Cl | 0 |
| H | C(=O)R$^{24}$ | —(CH$_2$)$_2$CH=CHCH$_2$CH=CHCH$_2$CH=CHCH$_2$CH=CHCH$_2$CH=CHCH$_2$CH$_3$ | Cl | 0 |
| H | C(=O)R$^{24}$ | —(CH$_2$)$_6$CH$_3$ | F | 0 |
| H | C(=O)R$^{24}$ | —(CH$_2$)$_8$CH$_3$ | F | 0 |
| H | C(=O)R$^{24}$ | —(CH$_2$)$_{10}$CH$_3$ | F | 0 |
| H | C(=O)R$^{24}$ | —(CH$_2$)$_{12}$CH$_3$ | F | 0 |
| H | C(=O)R$^{24}$ | —(CH$_2$)$_{14}$CH$_3$ | F | 0 |
| H | C(=O)R$^{24}$ | —(CH$_2$)$_{16}$CH$_3$ | F | 0 |
| H | C(=O)R$^{24}$ | —(CH$_2$)$_{18}$CH$_3$ | F | 0 |
| H | C(=O)R$^{24}$ | —(CH$_2$)$_{20}$CH$_3$ | F | 0 |
| H | C(=O)R$^{24}$ | —(CH$_2$)$_{22}$CH$_3$ | F | 0 |
| H | C(=O)R$^{24}$ | —(CH$_2$)$_{24}$CH$_3$ | F | 0 |
| H | C(=O)R$^{24}$ | —(CH$_2$)$_7$CH=CH(CH$_2$)$_3$CH$_3$ | F | 0 |
| H | C(=O)R$^{24}$ | —(CH$_2$)$_7$CH=CHCH$_2$CH=CH(CH$_2$)$_4$CH$_3$ | F | 0 |
| H | C(=O)R$^{24}$ | —(CH$_2$)$_7$CH=CH(CH$_2$)$_7$CH$_3$ | F | 0 |
| H | C(=O)R$^{24}$ | —(CH$_2$)$_7$CH=CHCH$_2$CH=CH(CH$_2$)$_4$CH$_3$ | F | 0 |
| H | C(=O)R$^{24}$ | —(CH$_2$)$_7$CH=CH(CH$_2$)$_7$CH$_3$ | F | 0 |
| H | C(=O)R$^{24}$ | —(CH$_2$)$_7$CH=CHCH$_2$CH=CHCH$_2$CH=CHCH$_2$CH$_3$ | F | 0 |
| H | C(=O)R$^{24}$ | —(CH$_2$)$_9$CH=CH(CH$_2$)$_5$CH$_3$ | F | 0 |
| H | C(=O)R$^{24}$ | —(CH$_2$)$_3$CH=CHCH$_2$CH=CHCH$_2$CH=CHCH$_2$CH=CH(CH$_2$)$_4$CH$_3$ | F | 0 |
| H | C(=O)R$^{24}$ | —(CH$_2$)$_{11}$CH=CH(CH$_2$)$_7$CH$_3$ | F | 0 |
| H | C(=O)R$^{24}$ | —(CH$_2$)$_3$CH=CHCH$_2$CH=CHCH$_2$CH=CHCH$_2$CH=CHCH$_2$CH=CHCH$_2$CH$_3$ | F | 0 |
| H | C(=O)R$^{24}$ | —(CH$_2$)$_4$CH=CHCH(CH$_3$)$_2$ | F | 0 |
| H | C(=O)R$^{24}$ | —(CH$_2$)$_2$CH=CHCH$_2$CH=CHCH$_2$CH=CHCH$_2$CH=CHCH$_2$CH=CHCH$_2$CH$_3$ | F | 0 |
| H | C(=O)R$^{24}$ | —(CH$_2$)$_6$CH$_3$ | S(O)$_2$CH$_3$ | 0 |
| H | C(=O)R$^{24}$ | —(CH$_2$)$_8$CH$_3$ | S(O)$_2$CH$_3$ | 0 |
| H | C(=O)R$^{24}$ | —(CH$_2$)$_{10}$CH$_3$ | S(O)$_2$CH$_3$ | 0 |
| H | C(=O)R$^{24}$ | —(CH$_2$)$_{12}$CH$_3$ | S(O)$_2$CH$_3$ | 0 |
| H | C(=O)R$^{24}$ | —(CH$_2$)$_{14}$CH$_3$ | S(O)$_2$CH$_3$ | 0 |
| H | C(=O)R$^{24}$ | —(CH$_2$)$_{16}$CH$_3$ | S(O)$_2$CH$_3$ | 0 |
| H | C(=O)R$^{24}$ | —(CH$_2$)$_{18}$CH$_3$ | S(O)$_2$CH$_3$ | 0 |
| H | C(=O)R$^{24}$ | —(CH$_2$)$_{20}$CH$_3$ | S(O)$_2$CH$_3$ | 0 |
| H | C(=O)R$^{24}$ | —(CH$_2$)$_{22}$CH$_3$ | S(O)$_2$CH$_3$ | 0 |
| H | C(=O)R$^{24}$ | —(CH$_2$)$_{24}$CH$_3$ | S(O)$_2$CH$_3$ | 0 |
| H | C(=O)R$^{24}$ | —(CH$_2$)$_7$CH=CH(CH$_2$)$_3$CH$_3$ | S(O)$_2$CH$_3$ | 0 |
| H | C(=O)R$^{24}$ | —(CH$_2$)$_7$CH=CHCH$_2$CH=CH(CH$_2$)$_4$CH$_3$ | S(O)$_2$CH$_3$ | 0 |
| H | C(=O)R$^{24}$ | —(CH$_2$)$_7$CH=CH(CH$_2$)$_7$CH$_3$ | S(O)$_2$CH$_3$ | 0 |
| H | C(=O)R$^{24}$ | —(CH$_2$)$_7$CH=CHCH$_2$CH=CH(CH$_2$)$_4$CH$_3$ | S(O)$_2$CH$_3$ | 0 |
| H | C(=O)R$^{24}$ | —(CH$_2$)$_7$CH=CH(CH$_2$)$_7$CH$_3$ | S(O)$_2$CH$_3$ | 0 |
| H | C(=O)R$^{24}$ | —(CH$_2$)$_7$CH=CHCH$_2$CH=CHCH$_2$CH=CHCH$_2$CH$_3$ | S(O)$_2$CH$_3$ | 0 |
| H | C(=O)R$^{24}$ | —(CH$_2$)$_9$CH=CH(CH$_2$)$_5$CH$_3$ | S(O)$_2$CH$_3$ | 0 |
| H | C(=O)R$^{24}$ | —(CH$_2$)$_3$CH=CHCH$_2$CH=CHCH$_2$CH=CHCH$_2$CH=CH(CH$_2$)$_4$CH$_3$ | S(O)$_2$CH$_3$ | 0 |
| H | C(=O)R$^{24}$ | —(CH$_2$)$_{11}$CH=CH(CH$_2$)$_7$CH$_3$ | S(O)$_2$CH$_3$ | 0 |
| H | C(=O)R$^{24}$ | —(CH$_2$)$_3$CH=CHCH$_2$CH=CHCH$_2$CH=CHCH$_2$CH=CHCH$_2$CH=CHCH$_2$CH$_3$ | S(O)$_2$CH$_3$ | 0 |
| H | C(=O)R$^{24}$ | —(CH$_2$)$_4$CH=CHCH(CH$_3$)$_2$ | S(O)$_2$CH$_3$ | 0 |
| H | C(=O)R$^{24}$ | —(CH$_2$)$_2$CH=CHCH$_2$CH=CHCH$_2$CH=CHCH$_2$CH=CHCH$_2$CH=CHCH$_2$CH$_3$ | S(O)$_2$CH$_3$ | 0 |
| H | C(=O)R$^{24}$ | —(CH$_2$)$_6$CH$_3$ | CF$_3$ | 0 |
| H | C(=O)R$^{24}$ | —(CH$_2$)$_8$CH$_3$ | CF$_3$ | 0 |
| H | C(=O)R$^{24}$ | —(CH$_2$)$_{10}$CH$_3$ | CF$_3$ | 0 |
| H | C(=O)R$^{24}$ | —(CH$_2$)$_{12}$CH$_3$ | CF$_3$ | 0 |
| H | C(=O)R$^{24}$ | —(CH$_2$)$_{14}$CH$_3$ | CF$_3$ | 0 |
| H | C(=O)R$^{24}$ | —(CH$_2$)$_{16}$CH$_3$ | CF$_3$ | 0 |
| H | C(=O)R$^{24}$ | —(CH$_2$)$_{18}$CH$_3$ | CF$_3$ | 0 |
| H | C(=O)R$^{24}$ | —(CH$_2$)$_{20}$CH$_3$ | CF$_3$ | 0 |
| H | C(=O)R$^{24}$ | —(CH$_2$)$_{22}$CH$_3$ | CF$_3$ | 0 |
| H | C(=O)R$^{24}$ | —(CH$_2$)$_{24}$CH$_3$ | CF$_3$ | 0 |
| H | C(=O)R$^{24}$ | —(CH$_2$)$_7$CH=CH(CH$_2$)$_3$CH$_3$ | CF$_3$ | 0 |
| H | C(=O)R$^{24}$ | —(CH$_2$)$_7$CH=CHCH$_2$CH=CH(CH$_2$)$_4$CH$_3$ | CF$_3$ | 0 |
| H | C(=O)R$^{24}$ | —(CH$_2$)$_7$CH=CH(CH$_2$)$_7$CH$_3$ | CF$_3$ | 0 |
| H | C(=O)R$^{24}$ | —(CH$_2$)$_7$CH=CHCH$_2$CH=CH(CH$_2$)$_4$CH$_3$ | CF$_3$ | 0 |
| H | C(=O)R$^{24}$ | —(CH$_2$)$_7$CH=CH(CH$_2$)$_7$CH$_3$ | CF$_3$ | 0 |
| H | C(=O)R$^{24}$ | —(CH$_2$)$_7$CH=CHCH$_2$CH=CHCH$_2$CH=CHCH$_2$CH$_3$ | CF$_3$ | 0 |

TABLE 1-continued $$R^3-\langle\rangle-(CH_2)_m-\underset{R^2}{\overset{R^1}{N}}$$

| R$^1$ | R$^2$ | R$^{2A}$ | R$^3$ | m |
|---|---|---|---|---|
| H | C(=O)R$^{2A}$ | —(CH$_2$)$_9$CH=CH(CH$_2$)$_5$CH$_3$ | CF$_3$ | 0 |
| H | C(=O)R$^{2A}$ | —(CH$_2$)$_3$CH=CHCH$_2$CH=CHCH$_2$CH=CHCH$_2$CH=CH(CH$_2$)$_4$CH$_3$ | CF$_3$ | 0 |
| H | C(=O)R$^{2A}$ | —(CH$_2$)$_{11}$CH=CH(CH$_2$)$_7$CH$_3$ | CF$_3$ | 0 |
| H | C(=O)R$^{2A}$ | —(CH$_2$)$_3$CH=CHCH$_2$CH=CHCH$_2$CH=CHCH$_2$CH=CHCH$_2$CH$_3$ | CF$_3$ | 0 |
| H | C(=O)R$^{2A}$ | —(CH$_2$)$_4$CH=CHCH(CH$_3$)$_2$ | CF$_3$ | 0 |
| H | C(=O)R$^{2A}$ | —(CH$_2$)$_2$CH=CHCH$_2$CH=CHCH$_2$CH=CHCH$_2$CH=CHCH$_2$CH=CHCH$_2$CH$_3$ | CF$_3$ | 0 |
| H | C(=O)R$^{2A}$ | —(CH$_2$)$_6$CH$_3$ | CHF$_2$ | 0 |
| H | C(=O)R$^{2A}$ | —(CH$_2$)$_8$CH$_3$ | CHF$_2$ | 0 |
| H | C(=O)R$^{2A}$ | —(CH$_2$)$_{10}$CH$_3$ | CHF$_2$ | 0 |
| H | C(=O)R$^{2A}$ | —(CH$_2$)$_{12}$CH$_3$ | CHF$_2$ | 0 |
| H | C(=O)R$^{2A}$ | —(CH$_2$)$_{14}$CH$_3$ | CHF$_2$ | 0 |
| H | C(=O)R$^{2A}$ | —(CH$_2$)$_{16}$CH$_3$ | CHF$_2$ | 0 |
| H | C(=O)R$^{2A}$ | —(CH$_2$)$_{18}$CH$_3$ | CHF$_2$ | 0 |
| H | C(=O)R$^{2A}$ | —(CH$_2$)$_{20}$CH$_3$ | CHF$_2$ | 0 |
| H | C(=O)R$^{2A}$ | —(CH$_2$)$_{22}$CH$_3$ | CHF$_2$ | 0 |
| H | C(=O)R$^{2A}$ | —(CH$_2$)$_{24}$CH$_3$ | CHF$_2$ | 0 |
| H | C(=O)R$^{2A}$ | —(CH$_2$)$_7$CH=CH(CH$_2$)$_3$CH$_3$ | CHF$_2$ | 0 |
| H | C(=O)R$^{2A}$ | —(CH$_2$)$_7$CH=CHCH$_2$CH=CH(CH$_2$)$_4$CH$_3$ | CHF$_2$ | 0 |
| H | C(=O)R$^{2A}$ | —(CH$_2$)$_7$CH=CH(CH$_2$)$_7$CH$_3$ | CHF$_2$ | 0 |
| H | C(=O)R$^{2A}$ | —(CH$_2$)$_7$CH=CHCH$_2$CH=CH(CH$_2$)$_4$CH$_3$ | CHF$_2$ | 0 |
| H | C(=O)R$^{2A}$ | —(CH$_2$)$_7$CH=CH(CH$_2$)$_7$CH$_3$ | CHF$_2$ | 0 |
| H | C(=O)R$^{2A}$ | —(CH$_2$)$_7$CH=CHCH$_2$CH=CHCH$_2$CH=CHCH$_2$CH$_3$ | CHF$_2$ | 0 |
| H | C(=O)R$^{2A}$ | —(CH$_2$)$_9$CH=CH(CH$_2$)$_5$CH$_3$ | CHF$_2$ | 0 |
| H | C(=O)R$^{2A}$ | —(CH$_2$)$_3$CH=CHCH$_2$CH=CHCH$_2$CH=CHCH$_2$CH=CH(CH$_2$)$_4$CH$_3$ | CHF$_2$ | 0 |
| H | C(=O)R$^{2A}$ | —(CH$_2$)$_{11}$CH=CH(CH$_2$)$_7$CH$_3$ | CHF$_2$ | 0 |
| H | C(=O)R$^{2A}$ | —(CH$_2$)$_3$CH=CHCH$_2$CH=CHCH$_2$CH=CHCH$_2$CH=CHCH$_2$CH$_3$ | CHF$_2$ | 0 |
| H | C(=O)R$^{2A}$ | —(CH$_2$)$_4$CH=CHCH(CH$_3$)$_2$ | CHF$_2$ | 0 |
| H | C(=O)R$^{2A}$ | —(CH$_2$)$_2$CH=CHCH$_2$CH=CHCH$_2$CH=CHCH$_2$CH=CHCH$_2$CH=CHCH$_2$CH$_3$ | CHF$_2$ | 0 |
| H | C(=O)R$^{2A}$ | —(CH$_2$)$_6$CH$_3$ | CF$_2$CH$_3$ | 0 |
| H | C(=O)R$^{2A}$ | —(CH$_2$)$_8$CH$_3$ | CF$_2$CH$_3$ | 0 |
| H | C(=O)R$^{2A}$ | —(CH$_2$)$_{10}$CH$_3$ | CF$_2$CH$_3$ | 0 |
| H | C(=O)R$^{2A}$ | —(CH$_2$)$_{12}$CH$_3$ | CF$_2$CH$_3$ | 0 |
| H | C(=O)R$^{2A}$ | —(CH$_2$)$_{14}$CH$_3$ | CF$_2$CH$_3$ | 0 |
| H | C(=O)R$^{2A}$ | —(CH$_2$)$_{16}$CH$_3$ | CF$_2$CH$_3$ | 0 |
| H | C(=O)R$^{2A}$ | —(CH$_2$)$_{18}$CH$_3$ | CF$_2$CH$_3$ | 0 |
| H | C(=O)R$^{2A}$ | —(CH$_2$)$_{20}$CH$_3$ | CF$_2$CH$_3$ | 0 |
| H | C(=O)R$^{2A}$ | —(CH$_2$)$_{22}$CH$_3$ | CF$_2$CH$_3$ | 0 |
| H | C(=O)R$^{2A}$ | —(CH$_2$)$_{24}$CH$_3$ | CF$_2$CH$_3$ | 0 |
| H | C(=O)R$^{2A}$ | —(CH$_2$)$_7$CH=CH(CH$_2$)$_3$CH$_3$ | CF$_2$CH$_3$ | 0 |
| H | C(=O)R$^{2A}$ | —(CH$_2$)$_7$CH=CHCH$_2$CH=CH(CH$_2$)$_4$CH$_3$ | CF$_2$CH$_3$ | 0 |
| H | C(=O)R$^{2A}$ | —(CH$_2$)$_7$CH=CH(CH$_2$)$_7$CH$_3$ | CF$_2$CH$_3$ | 0 |
| H | C(=O)R$^{2A}$ | —(CH$_2$)$_7$CH=CHCH$_2$CH=CH(CH$_2$)$_4$CH$_3$ | CF$_2$CH$_3$ | 0 |
| H | C(=O)R$^{2A}$ | —(CH$_2$)$_7$CH=CH(CH$_2$)$_7$CH$_3$ | CF$_2$CH$_3$ | 0 |
| H | C(=O)R$^{2A}$ | —(CH$_2$)$_7$CH=CHCH$_2$CH=CHCH$_2$CH=CHCH$_2$CH$_3$ | CF$_2$CH$_3$ | 0 |
| H | C(=O)R$^{2A}$ | —(CH$_2$)$_9$CH=CH(CH$_2$)$_5$CH$_3$ | CF$_2$CH$_3$ | 0 |
| H | C(=O)R$^{2A}$ | —(CH$_2$)$_3$CH=CHCH$_2$CH=CHCH$_2$CH=CHCH$_2$CH=CH(CH$_2$)$_4$CH$_3$ | CF$_2$CH$_3$ | 0 |
| H | C(=O)R$^{2A}$ | —(CH$_2$)$_{11}$CH=CH(CH$_2$)$_7$CH$_3$ | CF$_2$CH$_3$ | 0 |
| H | C(=O)R$^{2A}$ | —(CH$_2$)$_3$CH=CHCH$_2$CH=CHCH$_2$CH=CHCH$_2$CH=CHCH$_2$CH$_3$ | CF$_2$CH$_3$ | 0 |
| H | C(=O)R$^{2A}$ | —(CH$_2$)$_4$CH=CHCH(CH$_3$)$_2$ | CF$_2$CH$_3$ | 0 |
| H | C(=O)R$^{2A}$ | —(CH$_2$)$_2$CH=CHCH$_2$CH=CHCH$_2$CH=CHCH$_2$CH=CHCH$_2$CH=CHCH$_2$CH$_3$ | CF$_2$CH$_3$ | 0 |
| H | C(=O)R$^{2A}$ | —(CH$_2$)$_6$CH$_3$ | C(CH$_3$)$_2$OH | 0 |
| H | C(=O)R$^{2A}$ | —(CH$_2$)$_8$CH$_3$ | C(CH$_3$)$_2$OH | 0 |
| H | C(=O)R$^{2A}$ | —(CH$_2$)$_{10}$CH$_3$ | C(CH$_3$)$_2$OH | 0 |
| H | C(=O)R$^{2A}$ | —(CH$_2$)$_{12}$CH$_3$ | C(CH$_3$)$_2$OH | 0 |
| H | C(=O)R$^{2A}$ | —(CH$_2$)$_{14}$CH$_3$ | C(CH$_3$)$_2$OH | 0 |
| H | C(=O)R$^{2A}$ | —(CH$_2$)$_{16}$CH$_3$ | C(CH$_3$)$_2$OH | 0 |
| H | C(=O)R$^{2A}$ | —(CH$_2$)$_{18}$CH$_3$ | C(CH$_3$)$_2$OH | 0 |
| H | C(=O)R$^{2A}$ | —(CH$_2$)$_{20}$CH$_3$ | C(CH$_3$)$_2$OH | 0 |
| H | C(=O)R$^{2A}$ | —(CH$_2$)$_{22}$CH$_3$ | C(CH$_3$)$_2$OH | 0 |
| H | C(=O)R$^{2A}$ | —(CH$_2$)$_{24}$CH$_3$ | C(CH$_3$)$_2$OH | 0 |
| H | C(=O)R$^{2A}$ | —(CH$_2$)$_7$CH=CH(CH$_2$)$_3$CH$_3$ | C(CH$_3$)$_2$OH | 0 |
| H | C(=O)R$^{2A}$ | —(CH$_2$)$_7$CH=CHCH$_2$CH=CH(CH$_2$)$_4$CH$_3$ | C(CH$_3$)$_2$OH | 0 |
| H | C(=O)R$^{2A}$ | —(CH$_2$)$_7$CH=CH(CH$_2$)$_7$CH$_3$ | C(CH$_3$)$_2$OH | 0 |

TABLE 1-continued

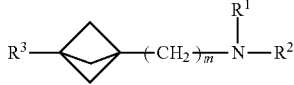

| R$^1$ | R$^2$ | R$^{2A}$ | R$^3$ | m |
|---|---|---|---|---|
| H | C(=O)R$^{24}$ | —(CH$_2$)$_7$CH=CHCH$_2$CH=CH(CH$_2$)$_4$CH$_3$ | C(CH$_3$)$_2$OH | 0 |
| H | C(=O)R$^{24}$ | —(CH$_2$)$_7$CH=CH(CH$_2$)$_7$CH$_3$ | C(CH$_3$)$_2$OH | 0 |
| H | C(=O)R$^{24}$ | —(CH$_2$)$_7$CH=CHCH$_2$CH=CHCH$_2$CH$_3$ | C(CH$_3$)$_2$OH | 0 |
| H | C(=O)R$^{24}$ | —(CH$_2$)$_9$CH=CH(CH$_2$)$_5$CH$_3$ | C(CH$_3$)$_2$OH | 0 |
| H | C(=O)R$^{24}$ | —(CH$_2$)$_3$CH=CHCH$_2$CH=CHCH$_2$CH=CHCH$_2$CH=CH(CH$_2$)$_4$CH$_3$ | C(CH$_3$)$_2$OH | 0 |
| H | C(=O)R$^{24}$ | —(CH$_2$)$_{11}$CH=CH(CH$_2$)$_7$CH$_3$ | C(CH$_3$)$_2$OH | 0 |
| H | C(=O)R$^{24}$ | —(CH$_2$)$_3$CH=CHCH$_2$CH=CHCH$_2$CH=CHCH$_2$CH=CHCH$_2$CH=CHCH$_2$CH$_3$ | C(CH$_3$)$_2$OH | 0 |
| H | C(=O)R$^{24}$ | —(CH$_2$)$_4$CH=CHCH(CH$_3$)$_2$ | C(CH$_3$)$_2$OH | 0 |
| H | C(=O)R$^{24}$ | —(CH$_2$)$_2$CH=CHCH$_2$CH=CHCH$_2$CH=CHCH$_2$CH=CHCH$_2$CH=CHCH$_2$CH$_3$ | C(CH$_3$)$_2$OH | 0 |
| H | C(=O)R$^{24}$ | —(CH$_2$)$_6$CH$_3$ | H | 1 |
| H | C(=O)R$^{24}$ | —(CH$_2$)$_8$CH$_3$ | H | 1 |
| H | C(=O)R$^{24}$ | —(CH$_2$)$_{10}$CH$_3$ | H | 1 |
| H | C(=O)R$^{24}$ | —(CH$_2$)$_{12}$CH$_3$ | H | 1 |
| H | C(=O)R$^{24}$ | —(CH$_2$)$_{14}$CH$_3$ | H | 1 |
| H | C(=O)R$^{24}$ | —(CH$_2$)$_{16}$CH$_3$ | H | 1 |
| H | C(=O)R$^{24}$ | —(CH$_2$)$_{18}$CH$_3$ | H | 1 |
| H | C(=O)R$^{24}$ | —(CH$_2$)$_{20}$CH$_3$ | H | 1 |
| H | C(=O)R$^{24}$ | —(CH$_2$)$_{22}$CH$_3$ | H | 1 |
| H | C(=O)R$^{24}$ | —(CH$_2$)$_{24}$CH$_3$ | H | 1 |
| H | C(=O)R$^{24}$ | —(CH$_2$)$_7$CH=CH(CH$_2$)$_3$CH$_3$ | H | 1 |
| H | C(=O)R$^{24}$ | —(CH$_2$)$_7$CH=CHCH$_2$CH=CH(CH$_2$)$_4$CH$_3$ | H | 1 |
| H | C(=O)R$^{24}$ | —(CH$_2$)$_7$CH=CH(CH$_2$)$_7$CH$_3$ | H | 1 |
| H | C(=O)R$^{24}$ | —(CH$_2$)$_7$CH=CHCH$_2$CH=CH(CH$_2$)$_4$CH$_3$ | H | 1 |
| H | C(=O)R$^{24}$ | —(CH$_2$)$_7$CH=CH(CH$_2$)$_7$CH$_3$ | H | 1 |
| H | C(=O)R$^{24}$ | —(CH$_2$)$_7$CH=CHCH$_2$CH=CHCH$_2$CH$_3$ | H | 1 |
| H | C(=O)R$^{24}$ | —(CH$_2$)$_9$CH=CH(CH$_2$)$_5$CH$_3$ | H | 1 |
| H | C(=O)R$^{24}$ | —(CH$_2$)$_3$CH=CHCH$_2$CH=CHCH$_2$CH=CHCH$_2$CH=CH(CH$_2$)$_4$CH$_3$ | H | 1 |
| H | C(=O)R$^{24}$ | —(CH$_2$)$_{11}$CH=CH(CH$_2$)$_7$CH$_3$ | H | 1 |
| H | C(=O)R$^{24}$ | —(CH$_2$)$_3$CH=CHCH$_2$CH=CHCH$_2$CH=CHCH$_2$CH=CHCH$_2$CH=CHCH$_2$CH$_3$ | H | 1 |
| H | C(=O)R$^{24}$ | —(CH$_2$)$_4$CH=CHCH(CH$_3$)$_2$ | H | 1 |
| H | C(=O)R$^{24}$ | —(CH$_2$)$_2$CH=CHCH$_2$CH=CHCH$_2$CH=CHCH$_2$CH=CHCH$_2$CH=CHCH$_2$CH$_3$ | H | 1 |
| H | C(=O)R$^{24}$ | —(CH$_2$)$_6$CH$_3$ | CH$_3$ | 1 |
| H | C(=O)R$^{24}$ | —(CH$_2$)$_8$CH$_3$ | CH$_3$ | 1 |
| H | C(=O)R$^{24}$ | —(CH$_2$)$_{10}$CH$_3$ | CH$_3$ | 1 |
| H | C(=O)R$^{24}$ | —(CH$_2$)$_{12}$CH$_3$ | CH$_3$ | 1 |
| H | C(=O)R$^{24}$ | —(CH$_2$)$_{14}$CH$_3$ | CH$_3$ | 1 |
| H | C(=O)R$^{24}$ | —(CH$_2$)$_{16}$CH$_3$ | CH$_3$ | 1 |
| H | C(=O)R$^{24}$ | —(CH$_2$)$_{18}$CH$_3$ | CH$_3$ | 1 |
| H | C(=O)R$^{24}$ | —(CH$_2$)$_{20}$CH$_3$ | CH$_3$ | 1 |
| H | C(=O)R$^{24}$ | —(CH$_2$)$_{22}$CH$_3$ | CH$_3$ | 1 |
| H | C(=O)R$^{24}$ | —(CH$_2$)$_{24}$CH$_3$ | CH$_3$ | 1 |
| H | C(=O)R$^{24}$ | —(CH$_2$)$_7$CH=CH(CH$_2$)$_3$CH$_3$ | CH$_3$ | 1 |
| H | C(=O)R$^{24}$ | —(CH$_2$)$_7$CH=CHCH$_2$CH=CH(CH$_2$)$_4$CH$_3$ | CH$_3$ | 1 |
| H | C(=O)R$^{24}$ | —(CH$_2$)$_7$CH=CH(CH$_2$)$_7$CH$_3$ | CH$_3$ | 1 |
| H | C(=O)R$^{24}$ | —(CH$_2$)$_7$CH=CHCH$_2$CH=CH(CH$_2$)$_4$CH$_3$ | CH$_3$ | 1 |
| H | C(=O)R$^{24}$ | —(CH$_2$)$_7$CH=CH(CH$_2$)$_7$CH$_3$ | CH$_3$ | 1 |
| H | C(=O)R$^{24}$ | —(CH$_2$)$_7$CH=CHCH$_2$CH=CHCH$_2$CH$_3$ | CH$_3$ | 1 |
| H | C(=O)R$^{24}$ | —(CH$_2$)$_9$CH=CH(CH$_2$)$_5$CH$_3$ | CH$_3$ | 1 |
| H | C(=O)R$^{24}$ | —(CH$_2$)$_3$CH=CHCH$_2$CH=CHCH$_2$CH=CHCH$_2$CH=CH(CH$_2$)$_4$CH$_3$ | CH$_3$ | 1 |
| H | C(=O)R$^{24}$ | —(CH$_2$)$_{11}$CH=CH(CH$_2$)$_7$CH$_3$ | CH$_3$ | 1 |
| H | C(=O)R$^{24}$ | —(CH$_2$)$_3$CH=CHCH$_2$CH=CHCH$_2$CH=CHCH$_2$CH=CHCH$_2$CH=CHCH$_2$CH$_3$ | CH$_3$ | 1 |
| H | C(=O)R$^{24}$ | —(CH$_2$)$_4$CH=CHCH(CH$_3$)$_2$ | CH$_3$ | 1 |
| H | C(=O)R$^{24}$ | —(CH$_2$)$_2$CH=CHCH$_2$CH=CHCH$_2$CH=CHCH$_2$CH=CHCH$_2$CH=CHCH$_2$CH$_3$ | CH$_3$ | 1 |
| H | C(=O)R$^{24}$ | —(CH$_2$)$_6$CH$_3$ | CH(CH$_3$)$_2$ | 1 |
| H | C(=O)R$^{24}$ | —(CH$_2$)$_8$CH$_3$ | CH(CH$_3$)$_2$ | 1 |
| H | C(=O)R$^{24}$ | —(CH$_2$)$_{10}$CH$_3$ | CH(CH$_3$)$_2$ | 1 |
| H | C(=O)R$^{24}$ | —(CH$_2$)$_{12}$CH$_3$ | CH(CH$_3$)$_2$ | 1 |
| H | C(=O)R$^{24}$ | —(CH$_2$)$_{14}$CH$_3$ | CH(CH$_3$)$_2$ | 1 |
| H | C(=O)R$^{24}$ | —(CH$_2$)$_{16}$CH$_3$ | CH(CH$_3$)$_2$ | 1 |
| H | C(=O)R$^{24}$ | —(CH$_2$)$_{18}$CH$_3$ | CH(CH$_3$)$_2$ | 1 |
| H | C(=O)R$^{24}$ | —(CH$_2$)$_{20}$CH$_3$ | CH(CH$_3$)$_2$ | 1 |
| H | C(=O)R$^{24}$ | —(CH$_2$)$_{22}$CH$_3$ | CH(CH$_3$)$_2$ | 1 |
| H | C(=O)R$^{24}$ | —(CH$_2$)$_{24}$CH$_3$ | CH(CH$_3$)$_2$ | 1 |

TABLE 1-continued $$R^3-\diamond-(CH_2)_m-N(R^1)-R^2$$

| R¹ | R² | R²⁴ | R³ | m |
|---|---|---|---|---|
| H | C(=O)R²⁴ | —(CH₂)₇CH=CH(CH₂)₃CH₃ | CH(CH₃)₂ | 1 |
| H | C(=O)R²⁴ | —(CH₂)₇CH=CHCH₂CH=CH(CH₂)₄CH₃ | CH(CH₃)₂ | 1 |
| H | C(=O)R²⁴ | —(CH₂)₇CH=CH(CH₂)₇CH₃ | CH(CH₃)₂ | 1 |
| H | C(=O)R²⁴ | —(CH₂)₇CH=CHCH₂CH=CH(CH₂)₄CH₃ | CH(CH₃)₂ | 1 |
| H | C(=O)R²⁴ | —(CH₂)₇CH=CH(CH₂)₇CH₃ | CH(CH₃)₂ | 1 |
| H | C(=O)R²⁴ | —(CH₂)₇CH=CHCH₂CH=CHCH₂CH=CHCH₂CH₃ | CH(CH₃)₂ | 1 |
| H | C(=O)R²⁴ | —(CH₂)₉CH=CH(CH₂)₅CH₃ | CH(CH₃)₂ | 1 |
| H | C(=O)R²⁴ | —(CH₂)₃CH=CHCH₂CH=CHCH₂CH=CHCH₂CH=CH(CH₂)₄CH₃ | CH(CH₃)₂ | 1 |
| H | C(=O)R²⁴ | —(CH₂)₁₁CH=CH(CH₂)₇CH₃ | CH(CH₃)₂ | 1 |
| H | C(=O)R²⁴ | —(CH₂)₃CH=CHCH₂CH=CHCH₂CH=CHCH=CHCH₂CH=CHCH₂CH₃ | CH(CH₃)₂ | 1 |
| H | C(=O)R²⁴ | —(CH₂)₄CH=CHCH(CH₃)₂ | CH(CH₃)₂ | 1 |
| H | C(=O)R²⁴ | —(CH₂)₂CH=CHCH₂CH=CHCH₂CH=CHCH₂CH=CHCH₂CH=CHCH₂CH₃ | CH(CH₃)₂ | 1 |
| H | C(=O)R²⁴ | —(CH₂)₆CH₃ | C(CH₃)₃ | 1 |
| H | C(=O)R²⁴ | —(CH₂)₈CH₃ | C(CH₃)₃ | 1 |
| H | C(=O)R²⁴ | —(CH₂)₁₀CH₃ | C(CH₃)₃ | 1 |
| H | C(=O)R²⁴ | —(CH₂)₁₂CH₃ | C(CH₃)₃ | 1 |
| H | C(=O)R²⁴ | —(CH₂)₁₄CH₃ | C(CH₃)₃ | 1 |
| H | C(=O)R²⁴ | —(CH₂)₁₆CH₃ | C(CH₃)₃ | 1 |
| H | C(=O)R²⁴ | —(CH₂)₁₈CH₃ | C(CH₃)₃ | 1 |
| H | C(=O)R²⁴ | —(CH₂)₂₀CH₃ | C(CH₃)₃ | 1 |
| H | C(=O)R²⁴ | —(CH₂)₂₂CH₃ | C(CH₃)₃ | 1 |
| H | C(=O)R²⁴ | —(CH₂)₂₄CH₃ | C(CH₃)₃ | 1 |
| H | C(=O)R²⁴ | —(CH₂)₇CH=CH(CH₂)₃CH₃ | C(CH₃)₃ | 1 |
| H | C(=O)R²⁴ | —(CH₂)₇CH=CHCH₂CH=CH(CH₂)₄CH₃ | C(CH₃)₃ | 1 |
| H | C(=O)R²⁴ | —(CH₂)₇CH=CH(CH₂)₇CH₃ | C(CH₃)₃ | 1 |
| H | C(=O)R²⁴ | —(CH₂)₇CH=CHCH₂CH=CH(CH₂)₄CH₃ | C(CH₃)₃ | 1 |
| H | C(=O)R²⁴ | —(CH₂)₇CH=CH(CH₂)₇CH₃ | C(CH₃)₃ | 1 |
| H | C(=O)R²⁴ | —(CH₂)₇CH=CHCH₂CH=CHCH₂CH=CHCH₂CH₃ | C(CH₃)₃ | 1 |
| H | C(=O)R²⁴ | —(CH₂)₉CH=CH(CH₂)₅CH₃ | C(CH₃)₃ | 1 |
| H | C(=O)R²⁴ | —(CH₂)₃CH=CHCH₂CH=CHCH₂CH=CHCH₂CH=CH(CH₂)₄CH₃ | C(CH₃)₃ | 1 |
| H | C(=O)R²⁴ | —(CH₂)₁₁CH=CH(CH₂)₇CH₃ | C(CH₃)₃ | 1 |
| H | C(=O)R²⁴ | —(CH₂)₃CH=CHCH₂CH=CHCH₂CH=CHCH=CHCH₂CH=CHCH₂CH₃ | C(CH₃)₃ | 1 |
| H | C(=O)R²⁴ | —(CH₂)₄CH=CHCH(CH₃)₂ | C(CH₃)₃ | 1 |
| H | C(=O)R²⁴ | —(CH₂)₂CH=CHCH₂CH=CHCH₂CH=CHCH₂CH=CHCH₂CH=CHCH₂CH₃ | C(CH₃)₃ | 1 |
| H | C(=O)R²⁴ | —(CH₂)₆CH₃ | cyclopropyl | 1 |
| H | C(=O)R²⁴ | —(CH₂)₈CH₃ | cyclopropyl | 1 |
| H | C(=O)R²⁴ | —(CH₂)₁₀CH₃ | cyclopropyl | 1 |
| H | C(=O)R²⁴ | —(CH₂)₁₂CH₃ | cyclopropyl | 1 |
| H | C(=O)R²⁴ | —(CH₂)₁₄CH₃ | cyclopropyl | 1 |
| H | C(=O)R²⁴ | —(CH₂)₁₆CH₃ | cyclopropyl | 1 |
| H | C(=O)R²⁴ | —(CH₂)₁₈CH₃ | cyclopropyl | 1 |
| H | C(=O)R²⁴ | —(CH₂)₂₀CH₃ | cyclopropyl | 1 |
| H | C(=O)R²⁴ | —(CH₂)₂₂CH₃ | cyclopropyl | 1 |
| H | C(=O)R²⁴ | —(CH₂)₂₄CH₃ | cyclopropyl | 1 |
| H | C(=O)R²⁴ | —(CH₂)₇CH=CH(CH₂)₃CH₃ | cyclopropyl | 1 |
| H | C(=O)R²⁴ | —(CH₂)₇CH=CHCH₂CH=CH(CH₂)₄CH₃ | cyclopropyl | 1 |
| H | C(=O)R²⁴ | —(CH₂)₇CH=CH(CH₂)₇CH₃ | cyclopropyl | 1 |
| H | C(=O)R²⁴ | —(CH₂)₇CH=CHCH₂CH=CH(CH₂)₄CH₃ | cyclopropyl | 1 |
| H | C(=O)R²⁴ | —(CH₂)₇CH=CH(CH₂)₇CH₃ | cyclopropyl | 1 |
| H | C(=O)R²⁴ | —(CH₂)₇CH=CHCH₂CH=CHCH₂CH=CHCH₂CH₃ | cyclopropyl | 1 |
| H | C(=O)R²⁴ | —(CH₂)₉CH=CH(CH₂)₅CH₃ | cyclopropyl | 1 |
| H | C(=O)R²⁴ | —(CH₂)₃CH=CHCH₂CH=CHCH₂CH=CHCH₂CH=CH(CH₂)₄CH₃ | cyclopropyl | 1 |
| H | C(=O)R²⁴ | —(CH₂)₁₁CH=CH(CH₂)₇CH₃ | cyclopropyl | 1 |
| H | C(=O)R²⁴ | —(CH₂)₃CH=CHCH₂CH=CHCH₂CH=CHCH=CHCH₂CH=CHCH₂CH₃ | cyclopropyl | 1 |
| H | C(=O)R²⁴ | —(CH₂)₄CH=CHCH(CH₃)₂ | cyclopropyl | 1 |
| H | C(=O)R²⁴ | —(CH₂)₂CH=CHCH₂CH=CHCH₂CH=CHCH₂CH=CHCH₂CH=CHCH₂CH₃ | cyclopropyl | 1 |
| H | C(=O)R²⁴ | —(CH₂)₆CH₃ | Cl | 1 |
| H | C(=O)R²⁴ | —(CH₂)₈CH₃ | Cl | 1 |
| H | C(=O)R²⁴ | —(CH₂)₁₀CH₃ | Cl | 1 |
| H | C(=O)R²⁴ | —(CH₂)₁₂CH₃ | Cl | 1 |
| H | C(=O)R²⁴ | —(CH₂)₁₄CH₃ | Cl | 1 |
| H | C(=O)R²⁴ | —(CH₂)₁₆CH₃ | Cl | 1 |
| H | C(=O)R²⁴ | —(CH₂)₁₈CH₃ | Cl | 1 |

TABLE 1-continued

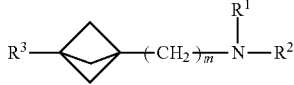

| R¹ | R² | R²⁴ | R³ | m |
|---|---|---|---|---|
| H | C(=O)R²⁴ | —(CH₂)₂₀CH₃ | Cl | 1 |
| H | C(=O)R²⁴ | —(CH₂)₂₂CH₃ | Cl | 1 |
| H | C(=O)R²⁴ | —(CH₂)₂₄CH₃ | Cl | 1 |
| H | C(=O)R²⁴ | —(CH₂)₇CH=CH(CH₂)₃CH₃ | Cl | 1 |
| H | C(=O)R²⁴ | —(CH₂)₇CH=CHCH₂CH=CH(CH₂)₄CH₃ | Cl | 1 |
| H | C(=O)R²⁴ | —(CH₂)₇CH=CH(CH₂)₇CH₃ | Cl | 1 |
| H | C(=O)R²⁴ | —(CH₂)₇CH=CHCH₂CH=CH(CH₂)₄CH₃ | Cl | 1 |
| H | C(=O)R²⁴ | —(CH₂)₇CH=CH(CH₂)₇CH₃ | Cl | 1 |
| H | C(=O)R²⁴ | —(CH₂)₇CH=CHCH₂CH=CHCH₂CH=CHCH₂CH₃ | Cl | 1 |
| H | C(=O)R²⁴ | —(CH₂)₉CH=CH(CH₂)₅CH₃ | Cl | 1 |
| H | C(=O)R²⁴ | —(CH₂)₃CH=CHCH₂CH=CHCH₂CH=CHCH₂CH=CH(CH₂)₄CH₃ | Cl | 1 |
| H | C(=O)R²⁴ | —(CH₂)₁₁CH=CH(CH₂)₇CH₃ | Cl | 1 |
| H | C(=O)R²⁴ | —(CH₂)₃CH=CHCH₂CH=CHCH₂CH=CHCH₂CH=CHCH₂CH=CHCH₂CH₃ | Cl | 1 |
| H | C(=O)R²⁴ | —(CH₂)₄CH=CHCH(CH₃)₂ | Cl | 1 |
| H | C(=O)R²⁴ | —(CH₂)₂CH=CHCH₂CH=CHCH₂CH=CHCH₂CH=CHCH₂CH=CHCH₂CH=CHCH₂CH₃ | Cl | 1 |
| H | C(=O)R²⁴ | —(CH₂)₆CH₃ | F | 1 |
| H | C(=O)R²⁴ | —(CH₂)₈CH₃ | F | 1 |
| H | C(=O)R²⁴ | —(CH₂)₁₀CH₃ | F | 1 |
| H | C(=O)R²⁴ | —(CH₂)₁₂CH₃ | F | 1 |
| H | C(=O)R²⁴ | —(CH₂)₁₄CH₃ | F | 1 |
| H | C(=O)R²⁴ | —(CH₂)₁₆CH₃ | F | 1 |
| H | C(=O)R²⁴ | —(CH₂)₁₈CH₃ | F | 1 |
| H | C(=O)R²⁴ | —(CH₂)₂₀CH₃ | F | 1 |
| H | C(=O)R²⁴ | —(CH₂)₂₂CH₃ | F | 1 |
| H | C(=O)R²⁴ | —(CH₂)₂₄CH₃ | F | 1 |
| H | C(=O)R²⁴ | —(CH₂)₇CH=CH(CH₂)₃CH₃ | F | 1 |
| H | C(=O)R²⁴ | —(CH₂)₇CH=CHCH₂CH=CH(CH₂)₄CH₃ | F | 1 |
| H | C(=O)R²⁴ | —(CH₂)₇CH=CH(CH₂)₇CH₃ | F | 1 |
| H | C(=O)R²⁴ | —(CH₂)₇CH=CHCH₂CH=CH(CH₂)₄CH₃ | F | 1 |
| H | C(=O)R²⁴ | —(CH₂)₇CH=CH(CH₂)₇CH₃ | F | 1 |
| H | C(=O)R²⁴ | —(CH₂)₇CH=CHCH₂CH=CHCH₂CH=CHCH₂CH₃ | F | 1 |
| H | C(=O)R²⁴ | —(CH₂)₉CH=CH(CH₂)₅CH₃ | F | 1 |
| H | C(=O)R²⁴ | —(CH₂)₃CH=CHCH₂CH=CHCH₂CH=CHCH₂CH=CH(CH₂)₄CH₃ | F | 1 |
| H | C(=O)R²⁴ | —(CH₂)₁₁CH=CH(CH₂)₇CH₃ | F | 1 |
| H | C(=O)R²⁴ | —(CH₂)₃CH=CHCH₂CH=CHCH₂CH=CHCH₂CH=CHCH₂CH=CHCH₂CH₃ | F | 1 |
| H | C(=O)R²⁴ | —(CH₂)₄CH=CHCH(CH₃)₂ | F | 1 |
| H | C(=O)R²⁴ | —(CH₂)₂CH=CHCH₂CH=CHCH₂CH=CHCH₂CH=CHCH₂CH=CHCH₂CH=CHCH₂CH₃ | F | 1 |
| H | C(=O)R²⁴ | —(CH₂)₆CH₃ | S(O)₂CH₃ | 1 |
| H | C(=O)R²⁴ | —(CH₂)₈CH₃ | S(O)₂CH₃ | 1 |
| H | C(=O)R²⁴ | —(CH₂)₁₀CH₃ | S(O)₂CH₃ | 1 |
| H | C(=O)R²⁴ | —(CH₂)₁₂CH₃ | S(O)₂CH₃ | 1 |
| H | C(=O)R²⁴ | —(CH₂)₁₄CH₃ | S(O)₂CH₃ | 1 |
| H | C(=O)R²⁴ | —(CH₂)₁₆CH₃ | S(O)₂CH₃ | 1 |
| H | C(=O)R²⁴ | —(CH₂)₁₈CH₃ | S(O)₂CH₃ | 1 |
| H | C(=O)R²⁴ | —(CH₂)₂₀CH₃ | S(O)₂CH₃ | 1 |
| H | C(=O)R²⁴ | —(CH₂)₂₂CH₃ | S(O)₂CH₃ | 1 |
| H | C(=O)R²⁴ | —(CH₂)₂₄CH₃ | S(O)₂CH₃ | 1 |
| H | C(=O)R²⁴ | —(CH₂)₇CH=CH(CH₂)₃CH₃ | S(O)₂CH₃ | 1 |
| H | C(=O)R²⁴ | —(CH₂)₇CH=CHCH₂CH=CH(CH₂)₄CH₃ | S(O)₂CH₃ | 1 |
| H | C(=O)R²⁴ | —(CH₂)₇CH=CH(CH₂)₇CH₃ | S(O)₂CH₃ | 1 |
| H | C(=O)R²⁴ | —(CH₂)₇CH=CHCH₂CH=CH(CH₂)₄CH₃ | S(O)₂CH₃ | 1 |
| H | C(=O)R²⁴ | —(CH₂)₇CH=CH(CH₂)₇CH₃ | S(O)₂CH₃ | 1 |
| H | C(=O)R²⁴ | —(CH₂)₇CH=CHCH₂CH=CHCH₂CH=CHCH₂CH₃ | S(O)₂CH₃ | 1 |
| H | C(=O)R²⁴ | —(CH₂)₉CH=CH(CH₂)₅CH₃ | S(O)₂CH₃ | 1 |
| H | C(=O)R²⁴ | —(CH₂)₃CH=CHCH₂CH=CHCH₂CH=CHCH₂CH=CH(CH₂)₄CH₃ | S(O)₂CH₃ | 1 |
| H | C(=O)R²⁴ | —(CH₂)₁₁CH=CH(CH₂)₇CH₃ | S(O)₂CH₃ | 1 |
| H | C(=O)R²⁴ | —(CH₂)₃CH=CHCH₂CH=CHCH₂CH=CHCH₂CH=CHCH₂CH=CHCH₂CH₃ | S(O)₂CH₃ | 1 |
| H | C(=O)R²⁴ | —(CH₂)₄CH=CHCH(CH₃)₂ | S(O)₂CH₃ | 1 |
| H | C(=O)R²⁴ | —(CH₂)₂CH=CHCH₂CH=CHCH₂CH=CHCH₂—CH=CHCH₂CH=CHCH₂CH=CHCH₂CH₃ | S(O)₂CH₃ | 1 |
| H | C(=O)R²⁴ | —(CH₂)₆CH₃ | CF₃ | 1 |
| H | C(=O)R²⁴ | —(CH₂)₈CH₃ | CF₃ | 1 |
| H | C(=O)R²⁴ | —(CH₂)₁₀CH₃ | CF₃ | 1 |
| H | C(=O)R²⁴ | —(CH₂)₁₂CH₃ | CF₃ | 1 |

TABLE 1-continued $$R^3 - \langle \rangle - (CH_2)_m - N{\overset{R^1}{\underset{R^2}{}}}$$

| R¹ | R² | R²ᴬ | R³ | m |
|---|---|---|---|---|
| H | C(=O)R²⁴ | —(CH₂)₁₄CH₃ | CF₃ | 1 |
| H | C(=O)R²⁴ | —(CH₂)₁₆CH₃ | CF₃ | 1 |
| H | C(=O)R²⁴ | —(CH₂)₁₈CH₃ | CF₃ | 1 |
| H | C(=O)R²⁴ | —(CH₂)₂₀CH₃ | CF₃ | 1 |
| H | C(=O)R²⁴ | —(CH₂)₂₂CH₃ | CF₃ | 1 |
| H | C(=O)R²⁴ | —(CH₂)₂₄CH₃ | CF₃ | 1 |
| H | C(=O)R²⁴ | —(CH₂)₇CH=CH(CH₂)₃CH₃ | CF₃ | 1 |
| H | C(=O)R²⁴ | —(CH₂)₇CH=CHCH₂CH=CH(CH₂)₄CH₃ | CF₃ | 1 |
| H | C(=O)R²⁴ | —(CH₂)₇CH=CH(CH₂)₇CH₃ | CF₃ | 1 |
| H | C(=O)R²⁴ | —(CH₂)₇CH=CHCH₂CH=CH(CH₂)₄CH₃ | CF₃ | 1 |
| H | C(=O)R²⁴ | —(CH₂)₇CH=CH(CH₂)₇CH₃ | CF₃ | 1 |
| H | C(=O)R²⁴ | —(CH₂)₇CH=CHCH₂CH=CHCH₂CH=CHCH₂CH₃ | CF₃ | 1 |
| H | C(=O)R²⁴ | —(CH₂)₉CH=CH(CH₂)₅CH₃ | CF₃ | 1 |
| H | C(=O)R²⁴ | —(CH₂)₃CH=CHCH₂CH=CHCH₂CH=CHCH₂CH=CH(CH₂)₄CH₃ | CF₃ | 1 |
| H | C(=O)R²⁴ | —(CH₂)₁₁CH=CH(CH₂)₇CH₃ | CF₃ | 1 |
| H | C(=O)R²⁴ | —(CH₂)₃CH=CHCH₂CH=CHCH₂CH=CHCH=CHCH₂CH=CHCH₂CH₃ | CF₃ | 1 |
| H | C(=O)R²⁴ | —(CH₂)₄CH=CHCH(CH₃)₂ | CF₃ | 1 |
| H | C(=O)R²⁴ | —(CH₂)₂CH=CHCH₂CH=CHCH₂CH=CHCH=CHCH₂CH=CHCH₂CH=CHCH₂CH₃ | CF₃ | 1 |
| H | C(=O)R²⁴ | —(CH₂)₆CH₃ | CHF₂ | 1 |
| H | C(=O)R²⁴ | —(CH₂)₈CH₃ | CHF₂ | 1 |
| H | C(=O)R²⁴ | —(CH₂)₁₀CH₃ | CHF₂ | 1 |
| H | C(=O)R²⁴ | —(CH₂)₁₂CH₃ | CHF₂ | 1 |
| H | C(=O)R²⁴ | —(CH₂)₁₄CH₃ | CHF₂ | 1 |
| H | C(=O)R²⁴ | —(CH₂)₁₆CH₃ | CHF₂ | 1 |
| H | C(=O)R²⁴ | —(CH₂)₁₈CH₃ | CHF₂ | 1 |
| H | C(=O)R²⁴ | —(CH₂)₂₀CH₃ | CHF₂ | 1 |
| H | C(=O)R²⁴ | —(CH₂)₂₂CH₃ | CHF₂ | 1 |
| H | C(=O)R²⁴ | —(CH₂)₂₄CH₃ | CHF₂ | 1 |
| H | C(=O)R²⁴ | —(CH₂)₇CH=CH(CH₂)₃CH₃ | CHF₂ | 1 |
| H | C(=O)R²⁴ | —(CH₂)₇CH=CHCH₂CH=CH(CH₂)₄CH₃ | CHF₂ | 1 |
| H | C(=O)R²⁴ | —(CH₂)₇CH=CH(CH₂)₇CH₃ | CHF₂ | 1 |
| H | C(=O)R²⁴ | —(CH₂)₇CH=CHCH₂CH=CH(CH₂)₄CH₃ | CHF₂ | 1 |
| H | C(=O)R²⁴ | —(CH₂)₇CH=CH(CH₂)₇CH₃ | CHF₂ | 1 |
| H | C(=O)R²⁴ | —(CH₂)₇CH=CHCH₂CH=CHCH₂CH=CHCH₂CH₃ | CHF₂ | 1 |
| H | C(=O)R²⁴ | —(CH₂)₉CH=CH(CH₂)₅CH₃ | CHF₂ | 1 |
| H | C(=O)R²⁴ | —(CH₂)₃CH=CHCH₂CH=CHCH₂CH=CHCH₂CH=CH(CH₂)₄CH₃ | CHF₂ | 1 |
| H | C(=O)R²⁴ | —(CH₂)₁₁CH=CH(CH₂)₇CH₃ | CHF₂ | 1 |
| H | C(=O)R²⁴ | —(CH₂)₃CH=CHCH₂CH=CHCH₂CH=CHCH=CHCH₂CH=CHCH₂CH₃ | CHF₂ | 1 |
| H | C(=O)R²⁴ | —(CH₂)₄CH=CHCH(CH₃)₂ | CHF₂ | 1 |
| H | C(=O)R²⁴ | —(CH₂)₂CH=CHCH₂CH=CHCH₂CH=CHCH=CHCH₂CH=CHCH₂CH=CHCH₂CH₃ | CHF₂ | 1 |
| H | C(=O)R²⁴ | —(CH₂)₆CH₃ | CF₂CH₃ | 1 |
| H | C(=O)R²⁴ | —(CH₂)₈CH₃ | CF₂CH₃ | 1 |
| H | C(=O)R²⁴ | —(CH₂)₁₀CH₃ | CF₂CH₃ | 1 |
| H | C(=O)R²⁴ | —(CH₂)₁₂CH₃ | CF₂CH₃ | 1 |
| H | C(=O)R²⁴ | —(CH₂)₁₄CH₃ | CF₂CH₃ | 1 |
| H | C(=O)R²⁴ | —(CH₂)₁₆CH₃ | CF₂CH₃ | 1 |
| H | C(=O)R²⁴ | —(CH₂)₁₈CH₃ | CF₂CH₃ | 1 |
| H | C(=O)R²⁴ | —(CH₂)₂₀CH₃ | CF₂CH₃ | 1 |
| H | C(=O)R²⁴ | —(CH₂)₂₂CH₃ | CF₂CH₃ | 1 |
| H | C(=O)R²⁴ | —(CH₂)₂₄CH₃ | CF₂CH₃ | 1 |
| H | C(=O)R²⁴ | —(CH₂)₇CH=CH(CH₂)₃CH₃ | CF₂CH₃ | 1 |
| H | C(=O)R²⁴ | —(CH₂)₇CH=CHCH₂CH=CH(CH₂)₄CH₃ | CF₂CH₃ | 1 |
| H | C(=O)R²⁴ | —(CH₂)₇CH=CH(CH₂)₇CH₃ | CF₂CH₃ | 1 |
| H | C(=O)R²⁴ | —(CH₂)₇CH=CHCH₂CH=CH(CH₂)₄CH₃ | CF₂CH₃ | 1 |
| H | C(=O)R²⁴ | —(CH₂)₇CH=CH(CH₂)₇CH₃ | CF₂CH₃ | 1 |
| H | C(=O)R²⁴ | —(CH₂)₇CH=CHCH₂CH=CHCH₂CH=CHCH₂CH₃ | CF₂CH₃ | 1 |
| H | C(=O)R²⁴ | —(CH₂)₉CH=CH(CH₂)₅CH₃ | CF₂CH₃ | 1 |
| H | C(=O)R²⁴ | —(CH₂)₃CH=CHCH₂CH=CHCH₂CH=CHCH₂CH=CH(CH₂)₄CH₃ | CF₂CH₃ | 1 |
| H | C(=O)R²⁴ | —(CH₂)₁₁CH=CH(CH₂)₇CH₃ | CF₂CH₃ | 1 |
| H | C(=O)R²⁴ | —(CH₂)₃CH=CHCH₂CH=CHCH₂CH=CHCH=CHCH₂CH=CHCH₂CH₃ | CF₂CH₃ | 1 |
| H | C(=O)R²⁴ | —(CH₂)₄CH=CHCH(CH₃)₂ | CF₂CH₃ | 1 |
| H | C(=O)R²⁴ | —(CH₂)₂CH=CHCH₂CH=CHCH₂CH=CHCH=CHCH₂CH=CHCH₂CH=CHCH₂CH₃ | CF₂CH₃ | 1 |
| H | C(=O)R²⁴ | —(CH₂)₆CH₃ | C(CH₃)₂OH | 1 |

TABLE 1-continued

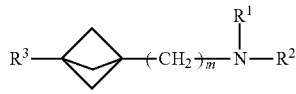

| R¹ | R² | R²⁴ | R³ | m |
|---|---|---|---|---|
| H | C(=O)R²⁴ | —(CH₂)₈CH₃ | C(CH₃)₂OH | 1 |
| H | C(=O)R²⁴ | —(CH₂)₁₀CH₃ | C(CH₃)₂OH | 1 |
| H | C(=O)R²⁴ | —(CH₂)₁₂CH₃ | C(CH₃)₂OH | 1 |
| H | C(=O)R²⁴ | —(CH₂)₁₄CH₃ | C(CH₃)₂OH | 1 |
| H | C(=O)R²⁴ | —(CH₂)₁₆CH₃ | C(CH₃)₂OH | 1 |
| H | C(=O)R²⁴ | —(CH₂)₁₈CH₃ | C(CH₃)₂OH | 1 |
| H | C(=O)R²⁴ | —(CH₂)₂₀CH₃ | C(CH₃)₂OH | 1 |
| H | C(=O)R²⁴ | —(CH₂)₂₂CH₃ | C(CH₃)₂OH | 1 |
| H | C(=O)R²⁴ | —(CH₂)₂₄CH₃ | C(CH₃)₂OH | 1 |
| H | C(=O)R²⁴ | —(CH₂)₇CH=CH(CH₂)₃CH₃ | C(CH₃)₂OH | 1 |
| H | C(=O)R²⁴ | —(CH₂)₇CH=CHCH₂CH=CH(CH₂)₄CH₃ | C(CH₃)₂OH | 1 |
| H | C(=O)R²⁴ | —(CH₂)₇CH=CH(CH₂)₇CH₃ | C(CH₃)₂OH | 1 |
| H | C(=O)R²⁴ | —(CH₂)₇CH=CHCH₂CH=CH(CH₂)₄CH₃ | C(CH₃)₂OH | 1 |
| H | C(=O)R²⁴ | —(CH₂)₇CH=CH(CH₂)₇CH₃ | C(CH₃)₂OH | 1 |
| H | C(=O)R²⁴ | —(CH₂)₇CH=CHCH₂CH=CHCH₂CH=CHCH₂CH₃ | C(CH₃)₂OH | 1 |
| H | C(=O)R²⁴ | —(CH₂)₉CH=CH(CH₂)₅CH₃ | C(CH₃)₂OH | 1 |
| H | C(=O)R²⁴ | —(CH₂)₃CH=CHCH₂CH=CHCH₂CH=CHCH₂CH=CH(CH₂)₄CH₃ | C(CH₃)₂OH | 1 |
| H | C(=O)R²⁴ | —(CH₂)₁₁CH=CH(CH₂)₇CH₃ | C(CH₃)₂OH | 1 |
| H | C(=O)R²⁴ | —(CH₂)₃CH=CHCH₂CH=CHCH₂CH=CHCH=CHCH₂CH=CHCH₂CH₃ | C(CH₃)₂OH | 1 |
| H | C(=O)R²⁴ | —(CH₂)₄CH=CHCH(CH₃)₂ | C(CH₃)₂OH | 1 |
| H | C(=O)R²⁴ | —(CH₂)₂CH=CHCH₂CH=CHCH₂CH=CHCH₂CH=CHCH₂CH=CHCH₂CH₃ | C(CH₃)₂OH | 1 |
| H | C(=O)R²⁴ | —(CH₂)₆CH₃ | H | 2 |
| H | C(=O)R²⁴ | —(CH₂)₈CH₃ | H | 2 |
| H | C(=O)R²⁴ | —(CH₂)₁₀CH₃ | H | 2 |
| H | C(=O)R²⁴ | —(CH₂)₁₂CH₃ | H | 2 |
| H | C(=O)R²⁴ | —(CH₂)₁₄CH₃ | H | 2 |
| H | C(=O)R²⁴ | —(CH₂)₁₆CH₃ | H | 2 |
| H | C(=O)R²⁴ | —(CH₂)₁₈CH₃ | H | 2 |
| H | C(=O)R²⁴ | —(CH₂)₂₀CH₃ | H | 2 |
| H | C(=O)R²⁴ | —(CH₂)₂₂CH₃ | H | 2 |
| H | C(=O)R²⁴ | —(CH₂)₂₄CH₃ | H | 2 |
| H | C(=O)R²⁴ | —(CH₂)₇CH=CH(CH₂)₃CH₃ | H | 2 |
| H | C(=O)R²⁴ | —(CH₂)₇CH=CHCH₂CH=CH(CH₂)₄CH₃ | H | 2 |
| H | C(=O)R²⁴ | —(CH₂)₇CH=CH(CH₂)₇CH₃ | H | 2 |
| H | C(=O)R²⁴ | —(CH₂)₇CH=CHCH₂CH=CH(CH₂)₄CH₃ | H | 2 |
| H | C(=O)R²⁴ | —(CH₂)₇CH=CH(CH₂)₇CH₃ | H | 2 |
| H | C(=O)R²⁴ | —(CH₂)₇CH=CHCH₂CH=CHCH₂CH=CHCH₂CH₃ | H | 2 |
| H | C(=O)R²⁴ | —(CH₂)₉CH=CH(CH₂)₅CH₃ | H | 2 |
| H | C(=O)R²⁴ | —(CH₂)₃CH=CHCH₂CH=CHCH₂CH=CHCH₂CH=CH(CH₂)₄CH₃ | H | 2 |
| H | C(=O)R²⁴ | —(CH₂)₁₁CH=CH(CH₂)₇CH₃ | H | 2 |
| H | C(=O)R²⁴ | —(CH₂)₃CH=CHCH₂CH=CHCH₂CH=CHCH=CHCH₂CH=CHCH₂CH₃ | H | 2 |
| H | C(=O)R²⁴ | —(CH₂)₄CH=CHCH(CH₃)₂ | H | 2 |
| H | C(=O)R²⁴ | —(CH₂)₂CH=CHCH₂CH=CHCH₂CH=CHCH₂CH=CHCH₂CH=CHCH₂CH₃ | H | 2 |
| H | C(=O)R²⁴ | —(CH₂)₆CH₃ | CH₃ | 2 |
| H | C(=O)R²⁴ | —(CH₂)₈CH₃ | CH₃ | 2 |
| H | C(=O)R²⁴ | —(CH₂)₁₀CH₃ | CH₃ | 2 |
| H | C(=O)R²⁴ | —(CH₂)₁₂CH₃ | CH₃ | 2 |
| H | C(=O)R²⁴ | —(CH₂)₁₄CH₃ | CH₃ | 2 |
| H | C(=O)R²⁴ | —(CH₂)₁₆CH₃ | CH₃ | 2 |
| H | C(=O)R²⁴ | —(CH₂)₁₈CH₃ | CH₃ | 2 |
| H | C(=O)R²⁴ | —(CH₂)₂₀CH₃ | CH₃ | 2 |
| H | C(=O)R²⁴ | —(CH₂)₂₂CH₃ | CH₃ | 2 |
| H | C(=O)R²⁴ | —(CH₂)₂₄CH₃ | CH₃ | 2 |
| H | C(=O)R²⁴ | —(CH₂)₇CH=CH(CH₂)₃CH₃ | CH₃ | 2 |
| H | C(=O)R²⁴ | —(CH₂)₇CH=CHCH₂CH=CH(CH₂)₄CH₃ | CH₃ | 2 |
| H | C(=O)R²⁴ | —(CH₂)₇CH=CH(CH₂)₇CH₃ | CH₃ | 2 |
| H | C(=O)R²⁴ | —(CH₂)₇CH=CHCH₂CH=CH(CH₂)₄CH₃ | CH₃ | 2 |
| H | C(=O)R²⁴ | —(CH₂)₇CH=CH(CH₂)₇CH₃ | CH₃ | 2 |
| H | C(=O)R²⁴ | —(CH₂)₇CH=CHCH₂CH=CHCH₂CH=CHCH₂CH₃ | CH₃ | 2 |
| H | C(=O)R²⁴ | —(CH₂)₉CH=CH(CH₂)₅CH₃ | CH₃ | 2 |
| H | C(=O)R²⁴ | —(CH₂)₃CH=CHCH₂CH=CHCH₂CH=CHCH₂CH=CH(CH₂)₄CH₃ | CH₃ | 2 |
| H | C(=O)R²⁴ | —(CH₂)₁₁CH=CH(CH₂)₇CH₃ | CH₃ | 2 |
| H | C(=O)R²⁴ | —(CH₂)₃CH=CHCH₂CH=CHCH₂CH=CHCH=CHCH₂CH=CHCH₂CH₃ | CH₃ | 2 |
| H | C(=O)R²⁴ | —(CH₂)₄CH=CHCH(CH₃)₂ | CH₃ | 2 |

TABLE 1-continued $$R^3 - \underset{}{\diamondsuit} - (CH_2)_m - \underset{R^2}{\overset{R^1}{N}}$$

| R¹ | R² | R²⁴ | R³ | m |
|---|---|---|---|---|
| H | C(=O)R²⁴ | —(CH₂)₂CH=CHCH₂CH=CHCH₂CH=CHCH₂CH=CHCH₂CH=CHCH₂CH=CHCH₂CH₃ | CH₃ | 2 |
| H | C(=O)R²⁴ | —(CH₂)₆CH₃ | CH(CH₃)₂ | 2 |
| H | C(=O)R²⁴ | —(CH₂)₈CH₃ | CH(CH₃)₂ | 2 |
| H | C(=O)R²⁴ | —(CH₂)₁₀CH₃ | CH(CH₃)₂ | 2 |
| H | C(=O)R²⁴ | —(CH₂)₁₂CH₃ | CH(CH₃)₂ | 2 |
| H | C(=O)R²⁴ | —(CH₂)₁₄CH₃ | CH(CH₃)₂ | 2 |
| H | C(=O)R²⁴ | —(CH₂)₁₆CH₃ | CH(CH₃)₂ | 2 |
| H | C(=O)R²⁴ | —(CH₂)₁₈CH₃ | CH(CH₃)₂ | 2 |
| H | C(=O)R²⁴ | —(CH₂)₂₀CH₃ | CH(CH₃)₂ | 2 |
| H | C(=O)R²⁴ | —(CH₂)₂₂CH₃ | CH(CH₃)₂ | 2 |
| H | C(=O)R²⁴ | —(CH₂)₂₄CH₃ | CH(CH₃)₂ | 2 |
| H | C(=O)R²⁴ | —(CH₂)₇CH=CH(CH₂)₃CH₃ | CH(CH₃)₂ | 2 |
| H | C(=O)R²⁴ | —(CH₂)₇CH=CHCH₂CH=CH(CH₂)₄CH₃ | CH(CH₃)₂ | 2 |
| H | C(=O)R²⁴ | —(CH₂)₇CH=CH(CH₂)₇CH₃ | CH(CH₃)₂ | 2 |
| H | C(=O)R²⁴ | —(CH₂)₇CH=CHCH₂CH=CH(CH₂)₄CH₃ | CH(CH₃)₂ | 2 |
| H | C(=O)R²⁴ | —(CH₂)₇CH=CH(CH₂)₇CH₃ | CH(CH₃)₂ | 2 |
| H | C(=O)R²⁴ | —(CH₂)₇CH=CHCH₂CH=CHCH₂CH=CHCH₂CH₃ | CH(CH₃)₂ | 2 |
| H | C(=O)R²⁴ | —(CH₂)₉CH=CH(CH₂)₅CH₃ | CH(CH₃)₂ | 2 |
| H | C(=O)R²⁴ | —(CH₂)₃CH=CHCH₂CH=CHCH₂CH=CHCH=CH(CH₂)₄CH₃ | CH(CH₃)₂ | 2 |
| H | C(=O)R²⁴ | —(CH₂)₁₁CH=CH(CH₂)₇CH₃ | CH(CH₃)₂ | 2 |
| H | C(=O)R²⁴ | —(CH₂)₃CH=CHCH₂CH=CHCH₂CH=CHCH₂CH=CHCH₂CH₃ | CH(CH₃)₂ | 2 |
| H | C(=O)R²⁴ | —(CH₂)₄CH=CHCH(CH₃)₂ | CH(CH₃)₂ | 2 |
| H | C(=O)R²⁴ | —(CH₂)₂CH=CHCH₂CH=CHCH₂CH=CHCH₂CH=CHCH₂CH=CHCH₂CH=CHCH₂CH₃ | CH(CH₃)₂ | 2 |
| H | C(=O)R²⁴ | —(CH₂)₆CH₃ | C(CH₃)₃ | 2 |
| H | C(=O)R²⁴ | —(CH₂)₈CH₃ | C(CH₃)₃ | 2 |
| H | C(=O)R²⁴ | —(CH₂)₁₀CH₃ | C(CH₃)₃ | 2 |
| H | C(=O)R²⁴ | —(CH₂)₁₂CH₃ | C(CH₃)₃ | 2 |
| H | C(=O)R²⁴ | —(CH₂)₁₄CH₃ | C(CH₃)₃ | 2 |
| H | C(=O)R²⁴ | —(CH₂)₁₆CH₃ | C(CH₃)₃ | 2 |
| H | C(=O)R²⁴ | —(CH₂)₁₈CH₃ | C(CH₃)₃ | 2 |
| H | C(=O)R²⁴ | —(CH₂)₂₀CH₃ | C(CH₃)₃ | 2 |
| H | C(=O)R²⁴ | —(CH₂)₂₂CH₃ | C(CH₃)₃ | 2 |
| H | C(=O)R²⁴ | —(CH₂)₂₄CH₃ | C(CH₃)₃ | 2 |
| H | C(=O)R²⁴ | —(CH₂)₇CH=CH(CH₂)₃CH₃ | C(CH₃)₃ | 2 |
| H | C(=O)R²⁴ | —(CH₂)₇CH=CHCH₂CH=CH(CH₂)₄CH₃ | C(CH₃)₃ | 2 |
| H | C(=O)R²⁴ | —(CH₂)₇CH=CH(CH₂)₇CH₃ | C(CH₃)₃ | 2 |
| H | C(=O)R²⁴ | —(CH₂)₇CH=CHCH₂CH=CH(CH₂)₄CH₃ | C(CH₃)₃ | 2 |
| H | C(=O)R²⁴ | —(CH₂)₇CH=CH(CH₂)₇CH₃ | C(CH₃)₃ | 2 |
| H | C(=O)R²⁴ | —(CH₂)₇CH=CHCH₂CH=CHCH₂CH=CHCH₂CH₃ | C(CH₃)₃ | 2 |
| H | C(=O)R²⁴ | —(CH₂)₉CH=CH(CH₂)₅CH₃ | C(CH₃)₃ | 2 |
| H | C(=O)R²⁴ | —(CH₂)₃CH=CHCH₂CH=CHCH₂CH=CHCH=CH(CH₂)₄CH₃ | C(CH₃)₃ | 2 |
| H | C(=O)R²⁴ | —(CH₂)₁₁CH=CH(CH₂)₇CH₃ | C(CH₃)₃ | 2 |
| H | C(=O)R²⁴ | —(CH₂)₃CH=CHCH₂CH=CHCH₂CH=CHCH₂CH=CHCH₂CH₃ | C(CH₃)₃ | 2 |
| H | C(=O)R²⁴ | —(CH₂)₄CH=CHCH(CH₃)₂ | C(CH₃)₃ | 2 |
| H | C(=O)R²⁴ | —(CH₂)₂CH=CHCH₂CH=CHCH₂CH=CHCH₂CH=CHCH₂CH=CHCH₂CH=CHCH₂CH₃ | C(CH₃)₃ | 2 |
| H | C(=O)R²⁴ | —(CH₂)₆CH₃ | cyclopropyl | 2 |
| H | C(=O)R²⁴ | —(CH₂)₈CH₃ | cyclopropyl | 2 |
| H | C(=O)R²⁴ | —(CH₂)₁₀CH₃ | cyclopropyl | 2 |
| H | C(=O)R²⁴ | —(CH₂)₁₂CH₃ | cyclopropyl | 2 |
| H | C(=O)R²⁴ | —(CH₂)₁₄CH₃ | cyclopropyl | 2 |
| H | C(=O)R²⁴ | —(CH₂)₁₆CH₃ | cyclopropyl | 2 |
| H | C(=O)R²⁴ | —(CH₂)₁₈CH₃ | cyclopropyl | 2 |
| H | C(=O)R²⁴ | —(CH₂)₂₀CH₃ | cyclopropyl | 2 |
| H | C(=O)R²⁴ | —(CH₂)₂₂CH₃ | cyclopropyl | 2 |
| H | C(=O)R²⁴ | —(CH₂)₂₄CH₃ | cyclopropyl | 2 |
| H | C(=O)R²⁴ | —(CH₂)₇CH=CH(CH₂)₃CH₃ | cyclopropyl | 2 |
| H | C(=O)R²⁴ | —(CH₂)₇CH=CHCH₂CH=CH(CH₂)₄CH₃ | cyclopropyl | 2 |
| H | C(=O)R²⁴ | —(CH₂)₇CH=CH(CH₂)₇CH₃ | cyclopropyl | 2 |
| H | C(=O)R²⁴ | —(CH₂)₇CH=CHCH₂CH=CH(CH₂)₄CH₃ | cyclopropyl | 2 |
| H | C(=O)R²⁴ | —(CH₂)₇CH=CH(CH₂)₇CH₃ | cyclopropyl | 2 |
| H | C(=O)R²⁴ | —(CH₂)₇CH=CHCH₂CH=CHCH₂CH=CHCH₂CH₃ | cyclopropyl | 2 |
| H | C(=O)R²⁴ | —(CH₂)₉CH=CH(CH₂)₅CH₃ | cyclopropyl | 2 |
| H | C(=O)R²⁴ | —(CH₂)₃CH=CHCH₂CH=CHCH₂CH=CHCH=CH(CH₂)₄CH₃ | cyclopropyl | 2 |
| H | C(=O)R²⁴ | —(CH₂)₁₁CH=CH(CH₂)₇CH₃ | cyclopropyl | 2 |

TABLE 1-continued $$R^3 - \diamond - (CH_2)_m - N{<}^{R^1}_{R^2}$$

| R¹ | R² | R²⁴ | R³ | m |
|---|---|---|---|---|
| H | C(=O)R²⁴ | —(CH₂)₃CH=CHCH₂CH=CHCH₂CH=CHCH₂CH=CHCH₂CH=CHCH₂CH₃ | cyclopropyl | 2 |
| H | C(=O)R²⁴ | —(CH₂)₄CH=CHCH(CH₃)₂ | cyclopropyl | 2 |
| H | C(=O)R²⁴ | —(CH₂)₂CH=CHCH₂CH=CHCH₂CH=CHCH₂CH=CHCH₂CH=CHCH₂CH₃ | cyclopropyl | 2 |
| H | C(=O)R²⁴ | —(CH₂)₆CH₃ | Cl | 2 |
| H | C(=O)R²⁴ | —(CH₂)₈CH₃ | Cl | 2 |
| H | C(=O)R²⁴ | —(CH₂)₁₀CH₃ | Cl | 2 |
| H | C(=O)R²⁴ | —(CH₂)₁₂CH₃ | Cl | 2 |
| H | C(=O)R²⁴ | —(CH₂)₁₄CH₃ | Cl | 2 |
| H | C(=O)R²⁴ | —(CH₂)₁₆CH₃ | Cl | 2 |
| H | C(=O)R²⁴ | —(CH₂)₁₈CH₃ | Cl | 2 |
| H | C(=O)R²⁴ | —(CH₂)₂₀CH₃ | Cl | 2 |
| H | C(=O)R²⁴ | —(CH₂)₂₂CH₃ | Cl | 2 |
| H | C(=O)R²⁴ | —(CH₂)₂₄CH₃ | Cl | 2 |
| H | C(=O)R²⁴ | —(CH₂)₇CH=CH(CH₂)₃CH₃ | Cl | 2 |
| H | C(=O)R²⁴ | —(CH₂)₇CH=CHCH₂CH=CH(CH₂)₄CH₃ | Cl | 2 |
| H | C(=O)R²⁴ | —(CH₂)₇CH=CH(CH₂)₇CH₃ | Cl | 2 |
| H | C(=O)R²⁴ | —(CH₂)₇CH=CHCH₂CH=CH(CH₂)₄CH₃ | Cl | 2 |
| H | C(=O)R²⁴ | —(CH₂)₇CH=CH(CH₂)₇CH₃ | Cl | 2 |
| H | C(=O)R²⁴ | —(CH₂)₇CH=CHCH₂CH=CHCH₂CH=CHCH₂CH₃ | Cl | 2 |
| H | C(=O)R²⁴ | —(CH₂)₉CH=CH(CH₂)₅CH₃ | Cl | 2 |
| H | C(=O)R²⁴ | —(CH₂)₃CH=CHCH₂CH=CHCH₂CH=CHCH₂CH=CH(CH₂)₄CH₃ | Cl | 2 |
| H | C(=O)R²⁴ | —(CH₂)₁₁CH=CH(CH₂)₇CH₃ | Cl | 2 |
| H | C(=O)R²⁴ | —(CH₂)₃CH=CHCH₂CH=CHCH₂CH=CHCH₂CH=CHCH₂CH=CHCH₂CH₃ | Cl | 2 |
| H | C(=O)R²⁴ | —(CH₂)₄CH=CHCH(CH₃)₂ | Cl | 2 |
| H | C(=O)R²⁴ | —(CH₂)₂CH=CHCH₂CH=CHCH₂CH=CHCH₂CH=CHCH₂CH=CHCH₂CH₃ | Cl | 2 |
| H | C(=O)R²⁴ | —(CH₂)₆CH₃ | F | 2 |
| H | C(=O)R²⁴ | —(CH₂)₈CH₃ | F | 2 |
| H | C(=O)R²⁴ | —(CH₂)₁₀CH₃ | F | 2 |
| H | C(=O)R²⁴ | —(CH₂)₁₂CH₃ | F | 2 |
| H | C(=O)R²⁴ | —(CH₂)₁₄CH₃ | F | 2 |
| H | C(=O)R²⁴ | —(CH₂)₁₆CH₃ | F | 2 |
| H | C(=O)R²⁴ | —(CH₂)₁₈CH₃ | F | 2 |
| H | C(=O)R²⁴ | —(CH₂)₂₀CH₃ | F | 2 |
| H | C(=O)R²⁴ | —(CH₂)₂₂CH₃ | F | 2 |
| H | C(=O)R²⁴ | —(CH₂)₂₄CH₃ | F | 2 |
| H | C(=O)R²⁴ | —(CH₂)₇CH=CH(CH₂)₃CH₃ | F | 2 |
| H | C(=O)R²⁴ | —(CH₂)₇CH=CHCH₂CH=CH(CH₂)₄CH₃ | F | 2 |
| H | C(=O)R²⁴ | —(CH₂)₇CH=CH(CH₂)₇CH₃ | F | 2 |
| H | C(=O)R²⁴ | —(CH₂)₇CH=CHCH₂CH=CH(CH₂)₄CH₃ | F | 2 |
| H | C(=O)R²⁴ | —(CH₂)₇CH=CH(CH₂)₇CH₃ | F | 2 |
| H | C(=O)R²⁴ | —(CH₂)₇CH=CHCH₂CH=CHCH₂CH=CHCH₂CH₃ | F | 2 |
| H | C(=O)R²⁴ | —(CH₂)₉CH=CH(CH₂)₅CH₃ | F | 2 |
| H | C(=O)R²⁴ | —(CH₂)₃CH=CHCH₂CH=CHCH₂CH=CHCH₂CH=CH(CH₂)₄CH₃ | F | 2 |
| H | C(=O)R²⁴ | —(CH₂)₁₁CH=CH(CH₂)₇CH₃ | F | 2 |
| H | C(=O)R²⁴ | —(CH₂)₃CH=CHCH₂CH=CHCH₂CH=CHCH₂CH=CHCH₂CH=CHCH₂CH₃ | F | 2 |
| H | C(=O)R²⁴ | —(CH₂)₄CH=CHCH(CH₃)₂ | F | 2 |
| H | C(=O)R²⁴ | —(CH₂)₂CH=CHCH₂CH=CHCH₂CH=CHCH₂CH=CHCH₂CH=CHCH₂CH₃ | F | 2 |
| H | C(=O)R²⁴ | —(CH₂)₆CH₃ | S(O)₂CH₃ | 2 |
| H | C(=O)R²⁴ | —(CH₂)₈CH₃ | S(O)₂CH₃ | 2 |
| H | C(=O)R²⁴ | —(CH₂)₁₀CH₃ | S(O)₂CH₃ | 2 |
| H | C(=O)R²⁴ | —(CH₂)₁₂CH₃ | S(O)₂CH₃ | 2 |
| H | C(=O)R²⁴ | —(CH₂)₁₄CH₃ | S(O)₂CH₃ | 2 |
| H | C(=O)R²⁴ | —(CH₂)₁₆CH₃ | S(O)₂CH₃ | 2 |
| H | C(=O)R²⁴ | —(CH₂)₁₈CH₃ | S(O)₂CH₃ | 2 |
| H | C(=O)R²⁴ | —(CH₂)₂₀CH₃ | S(O)₂CH₃ | 2 |
| H | C(=O)R²⁴ | —(CH₂)₂₂CH₃ | S(O)₂CH₃ | 2 |
| H | C(=O)R²⁴ | —(CH₂)₂₄CH₃ | S(O)₂CH₃ | 2 |
| H | C(=O)R²⁴ | —(CH₂)₇CH=CH(CH₂)₃CH₃ | S(O)₂CH₃ | 2 |
| H | C(=O)R²⁴ | —(CH₂)₇CH=CHCH₂CH=CH(CH₂)₄CH₃ | S(O)₂CH₃ | 2 |
| H | C(=O)R²⁴ | —(CH₂)₇CH=CH(CH₂)₇CH₃ | S(O)₂CH₃ | 2 |
| H | C(=O)R²⁴ | —(CH₂)₇CH=CHCH₂CH=CH(CH₂)₄CH₃ | S(O)₂CH₃ | 2 |
| H | C(=O)R²⁴ | —(CH₂)₇CH=CH(CH₂)₇CH₃ | S(O)₂CH₃ | 2 |
| H | C(=O)R²⁴ | —(CH₂)₇CH=CHCH₂CH=CHCH₂CH=CHCH₂CH₃ | S(O)₂CH₃ | 2 |
| H | C(=O)R²⁴ | —(CH₂)₉CH=CH(CH₂)₅CH₃ | S(O)₂CH₃ | 2 |

TABLE 1-continued $$R^3 - \langle \rangle - (CH_2)_m - N(R^1) - R^2$$

| $R^1$ | $R^2$ | $R^{24}$ | $R^3$ | m |
|---|---|---|---|---|
| H | C(=O)$R^{24}$ | —(CH$_2$)$_3$CH=CHCH$_2$CH=CHCH$_2$CH=CHCH$_2$CH=CH(CH$_2$)$_4$CH$_3$ | S(O)$_2$CH$_3$ | 2 |
| H | C(=O)$R^{24}$ | —(CH$_2$)$_{11}$CH=CH(CH$_2$)$_7$CH$_3$ | S(O)$_2$CH$_3$ | 2 |
| H | C(=O)$R^{24}$ | —(CH$_2$)$_3$CH=CHCH$_2$CH=CHCH$_2$CH=CHCH$_2$CH=CHCH$_2$CH=CHCH$_2$CH$_3$ | S(O)$_2$CH$_3$ | 2 |
| H | C(=O)$R^{24}$ | —(CH$_2$)$_4$CH=CHCH(CH$_3$)$_2$ | S(O)$_2$CH$_3$ | 2 |
| H | C(=O)$R^{24}$ | —(CH$_2$)$_2$CH=CHCH$_2$CH=CHCH$_2$CH=CHCH$_2$CH=CHCH$_2$CH=CHCH$_2$CH$_3$ | S(O)$_2$CH$_3$ | 2 |
| H | C(=O)$R^{24}$ | —(CH$_2$)$_6$CH$_3$ | CF$_3$ | 2 |
| H | C(=O)$R^{24}$ | —(CH$_2$)$_8$CH$_3$ | CF$_3$ | 2 |
| H | C(=O)$R^{24}$ | —(CH$_2$)$_{10}$CH$_3$ | CF$_3$ | 2 |
| H | C(=O)$R^{24}$ | —(CH$_2$)$_{12}$CH$_3$ | CF$_3$ | 2 |
| H | C(=O)$R^{24}$ | —(CH$_2$)$_{14}$CH$_3$ | CF$_3$ | 2 |
| H | C(=O)$R^{24}$ | —(CH$_2$)$_{16}$CH$_3$ | CF$_3$ | 2 |
| H | C(=O)$R^{24}$ | —(CH$_2$)$_{18}$CH$_3$ | CF$_3$ | 2 |
| H | C(=O)$R^{24}$ | —(CH$_2$)$_{20}$CH$_3$ | CF$_3$ | 2 |
| H | C(=O)$R^{24}$ | —(CH$_2$)$_{22}$CH$_3$ | CF$_3$ | 2 |
| H | C(=O)$R^{24}$ | —(CH$_2$)$_{24}$CH$_3$ | CF$_3$ | 2 |
| H | C(=O)$R^{24}$ | —(CH$_2$)$_7$CH=CH(CH$_2$)$_3$CH$_3$ | CF$_3$ | 2 |
| H | C(=O)$R^{24}$ | —(CH$_2$)$_7$CH=CHCH$_2$CH=CH(CH$_2$)$_4$CH$_3$ | CF$_3$ | 2 |
| H | C(=O)$R^{24}$ | —(CH$_2$)$_7$CH=CH(CH$_2$)$_7$CH$_3$ | CF$_3$ | 2 |
| H | C(=O)$R^{24}$ | —(CH$_2$)$_7$CH=CHCH$_2$CH=CH(CH$_2$)$_4$CH$_3$ | CF$_3$ | 2 |
| H | C(=O)$R^{24}$ | —(CH$_2$)$_7$CH=CH(CH$_2$)$_7$CH$_3$ | CF$_3$ | 2 |
| H | C(=O)$R^{24}$ | —(CH$_2$)$_7$CH=CHCH$_2$CH=CHCH$_2$CH=CHCH$_2$CH$_3$ | CF$_3$ | 2 |
| H | C(=O)$R^{24}$ | —(CH$_2$)$_9$CH=CH(CH$_2$)$_5$CH$_3$ | CF$_3$ | 2 |
| H | C(=O)$R^{24}$ | —(CH$_2$)$_3$CH=CHCH$_2$CH=CHCH$_2$CH=CHCH$_2$CH=CH(CH$_2$)$_4$CH$_3$ | CF$_3$ | 2 |
| H | C(=O)$R^{24}$ | —(CH$_2$)$_{11}$CH=CH(CH$_2$)$_7$CH$_3$ | CF$_3$ | 2 |
| H | C(=O)$R^{24}$ | —(CH$_2$)$_3$CH=CHCH$_2$CH=CHCH$_2$CH=CHCH$_2$CH=CHCH$_2$CH=CHCH$_2$CH$_3$ | CF$_3$ | 2 |
| H | C(=O)$R^{24}$ | —(CH$_2$)$_4$CH=CHCH(CH$_3$)$_2$ | CF$_3$ | 2 |
| H | C(=O)$R^{24}$ | —(CH$_2$)$_2$CH=CHCH$_2$CH=CHCH$_2$CH=CHCH$_2$CH=CHCH$_2$CH=CHCH$_2$CH$_3$ | CF$_3$ | 2 |
| H | C(=O)$R^{24}$ | —(CH$_2$)$_6$CH$_3$ | CHF$_2$ | 2 |
| H | C(=O)$R^{24}$ | —(CH$_2$)$_8$CH$_3$ | CHF$_2$ | 2 |
| H | C(=O)$R^{24}$ | —(CH$_2$)$_{10}$CH$_3$ | CHF$_2$ | 2 |
| H | C(=O)$R^{24}$ | —(CH$_2$)$_{12}$CH$_3$ | CHF$_2$ | 2 |
| H | C(=O)$R^{24}$ | —(CH$_2$)$_{14}$CH$_3$ | CHF$_2$ | 2 |
| H | C(=O)$R^{24}$ | —(CH$_2$)$_{16}$CH$_3$ | CHF$_2$ | 2 |
| H | C(=O)$R^{24}$ | —(CH$_2$)$_{18}$CH$_3$ | CHF$_2$ | 2 |
| H | C(=O)$R^{24}$ | —(CH$_2$)$_{20}$CH$_3$ | CHF$_2$ | 2 |
| H | C(=O)$R^{24}$ | —(CH$_2$)$_{22}$CH$_3$ | CHF$_2$ | 2 |
| H | C(=O)$R^{24}$ | —(CH$_2$)$_{24}$CH$_3$ | CHF$_2$ | 2 |
| H | C(=O)$R^{24}$ | —(CH$_2$)$_7$CH=CH(CH$_2$)$_3$CH$_3$ | CHF$_2$ | 2 |
| H | C(=O)$R^{24}$ | —(CH$_2$)$_7$CH=CHCH$_2$CH=CH(CH$_2$)$_4$CH$_3$ | CHF$_2$ | 2 |
| H | C(=O)$R^{24}$ | —(CH$_2$)$_7$CH=CH(CH$_2$)$_7$CH$_3$ | CHF$_2$ | 2 |
| H | C(=O)$R^{24}$ | —(CH$_2$)$_7$CH=CHCH$_2$CH=CH(CH$_2$)$_4$CH$_3$ | CHF$_2$ | 2 |
| H | C(=O)$R^{24}$ | —(CH$_2$)$_7$CH=CH(CH$_2$)$_7$CH$_3$ | CHF$_2$ | 2 |
| H | C(=O)$R^{24}$ | —(CH$_2$)$_7$CH=CHCH$_2$CH=CHCH$_2$CH=CHCH$_2$CH$_3$ | CHF$_2$ | 2 |
| H | C(=O)$R^{24}$ | —(CH$_2$)$_9$CH=CH(CH$_2$)$_5$CH$_3$ | CHF$_2$ | 2 |
| H | C(=O)$R^{24}$ | —(CH$_2$)$_3$CH=CHCH$_2$CH=CHCH$_2$CH=CHCH$_2$CH=CH(CH$_2$)$_4$CH$_3$ | CHF$_2$ | 2 |
| H | C(=O)$R^{24}$ | —(CH$_2$)$_{11}$CH=CH(CH$_2$)$_7$CH$_3$ | CHF$_2$ | 2 |
| H | C(=O)$R^{24}$ | —(CH$_2$)$_3$CH=CHCH$_2$CH=CHCH$_2$CH=CHCH$_2$CH=CHCH$_2$CH=CHCH$_2$CH$_3$ | CHF$_2$ | 2 |
| H | C(=O)$R^{24}$ | —(CH$_2$)$_4$CH=CHCH(CH$_3$)$_2$ | CHF$_2$ | 2 |
| H | C(=O)$R^{24}$ | —(CH$_2$)$_2$CH=CHCH$_2$CH=CHCH$_2$CH=CHCH$_2$CH=CHCH$_2$CH=CHCH$_2$CH$_3$ | CHF$_2$ | 2 |
| H | C(=O)$R^{24}$ | —(CH$_2$)$_6$CH$_3$ | CF$_2$CH$_3$ | 2 |
| H | C(=O)$R^{24}$ | —(CH$_2$)$_8$CH$_3$ | CF$_2$CH$_3$ | 2 |
| H | C(=O)$R^{24}$ | —(CH$_2$)$_{10}$CH$_3$ | CF$_2$CH$_3$ | 2 |
| H | C(=O)$R^{24}$ | —(CH$_2$)$_{12}$CH$_3$ | CF$_2$CH$_3$ | 2 |
| H | C(=O)$R^{24}$ | —(CH$_2$)$_{14}$CH$_3$ | CF$_2$CH$_3$ | 2 |
| H | C(=O)$R^{24}$ | —(CH$_2$)$_{16}$CH$_3$ | CF$_2$CH$_3$ | 2 |
| H | C(=O)$R^{24}$ | —(CH$_2$)$_{18}$CH$_3$ | CF$_2$CH$_3$ | 2 |
| H | C(=O)$R^{24}$ | —(CH$_2$)$_{20}$CH$_3$ | CF$_2$CH$_3$ | 2 |
| H | C(=O)$R^{24}$ | —(CH$_2$)$_{22}$CH$_3$ | CF$_2$CH$_3$ | 2 |
| H | C(=O)$R^{24}$ | —(CH$_2$)$_{24}$CH$_3$ | CF$_2$CH$_3$ | 2 |
| H | C(=O)$R^{24}$ | —(CH$_2$)$_7$CH=CH(CH$_2$)$_3$CH$_3$ | CF$_2$CH$_3$ | 2 |
| H | C(=O)$R^{24}$ | —(CH$_2$)$_7$CH=CHCH$_2$CH=CH(CH$_2$)$_4$CH$_3$ | CF$_2$CH$_3$ | 2 |
| H | C(=O)$R^{24}$ | —(CH$_2$)$_7$CH=CH(CH$_2$)$_7$CH$_3$ | CF$_2$CH$_3$ | 2 |
| H | C(=O)$R^{24}$ | —(CH$_2$)$_7$CH=CHCH$_2$CH=CH(CH$_2$)$_4$CH$_3$ | CF$_2$CH$_3$ | 2 |

TABLE 1-continued $$R^3 - \diamondsuit - (CH_2)_m - N(R^1)(R^2)$$

| R¹ | R² | R²·⁴ | R³ | m |
|---|---|---|---|---|
| H | C(=O)R²⁴ | —(CH₂)₇CH=CH(CH₂)₇CH₃ | CF₂CH₃ | 2 |
| H | C(=O)R²⁴ | —(CH₂)₇CH=CHCH₂CH=CHCH₂CH=CHCH₂CH₃ | CF₂CH₃ | 2 |
| H | C(=O)R²⁴ | —(CH₂)₉CH=CH(CH₂)₅CH₃ | CF₂CH₃ | 2 |
| H | C(=O)R²⁴ | —(CH₂)₃CH=CHCH₂CH=CHCH₂CH=CHCH=CH(CH₂)₄CH₃ | CF₂CH₃ | 2 |
| H | C(=O)R²⁴ | —(CH₂)₁₁CH=CH(CH₂)₇CH₃ | CF₂CH₃ | 2 |
| H | C(=O)R²⁴ | —(CH₂)₃CH=CHCH₂CH=CHCH₂CH=CHCH₂CH=CHCH₂CH₃ | CF₂CH₃ | 2 |
| H | C(=O)R²⁴ | —(CH₂)₄CH=CHCH(CH₃)₂ | CF₂CH₃ | 2 |
| H | C(=O)R²⁴ | —(CH₂)₂CH=CHCH₂CH=CHCH₂CH=CHCH₂CH=CHCH₂CH=CHCH₂CH₃ | CF₂CH₃ | 2 |
| H | C(=O)R²⁴ | —(CH₂)₆CH₃ | C(CH₃)₂OH | 2 |
| H | C(=O)R²⁴ | —(CH₂)₈CH₃ | C(CH₃)₂OH | 2 |
| H | C(=O)R²⁴ | —(CH₂)₁₀CH₃ | C(CH₃)₂OH | 2 |
| H | C(=O)R²⁴ | —(CH₂)₁₂CH₃ | C(CH₃)₂OH | 2 |
| H | C(=O)R²⁴ | —(CH₂)₁₄CH₃ | C(CH₃)₂OH | 2 |
| H | C(=O)R²⁴ | —(CH₂)₁₆CH₃ | C(CH₃)₂OH | 2 |
| H | C(=O)R²⁴ | —(CH₂)₁₈CH₃ | C(CH₃)₂OH | 2 |
| H | C(=O)R²⁴ | —(CH₂)₂₀CH₃ | C(CH₃)₂OH | 2 |
| H | C(=O)R²⁴ | —(CH₂)₂₂CH₃ | C(CH₃)₂OH | 2 |
| H | C(=O)R²⁴ | —(CH₂)₂₄CH₃ | C(CH₃)₂OH | 2 |
| H | C(=O)R²⁴ | —(CH₂)₇CH=CH(CH₂)₃CH₃ | C(CH₃)₂OH | 2 |
| H | C(=O)R²⁴ | —(CH₂)₇CH=CHCH₂CH=CH(CH₂)₄CH₃ | C(CH₃)₂OH | 2 |
| H | C(=O)R²⁴ | —(CH₂)₇CH=CH(CH₂)₇CH₃ | C(CH₃)₂OH | 2 |
| H | C(=O)R²⁴ | —(CH₂)₇CH=CHCH₂CH=CH(CH₂)₄CH₃ | C(CH₃)₂OH | 2 |
| H | C(=O)R²⁴ | —(CH₂)₇CH=CH(CH₂)₇CH₃ | C(CH₃)₂OH | 2 |
| H | C(=O)R²⁴ | —(CH₂)₇CH=CHCH₂CH=CHCH₂CH=CHCH₂CH₃ | C(CH₃)₂OH | 2 |
| H | C(=O)R²⁴ | —(CH₂)₉CH=CH(CH₂)₅CH₃ | C(CH₃)₂OH | 2 |
| H | C(=O)R²⁴ | —(CH₂)₃CH=CHCH₂CH=CHCH₂CH=CHCH=CH(CH₂)₄CH₃ | C(CH₃)₂OH | 2 |
| H | C(=O)R²⁴ | —(CH₂)₁₁CH=CH(CH₂)₇CH₃ | C(CH₃)₂OH | 2 |
| H | C(=O)R²⁴ | —(CH₂)₃CH=CHCH₂CH=CHCH₂CH=CHCH₂CH=CHCH₂CH₃ | C(CH₃)₂OH | 2 |
| H | C(=O)R²⁴ | —(CH₂)₄CH=CHCH(CH₃)₂ | C(CH₃)₂OH | 2 |
| H | C(=O)R²⁴ | —(CH₂)₂CH=CHCH₂CH=CHCH₂CH=CHCH₂CH=CHCH₂CH=CHCH₂CH₃ | C(CH₃)₂OH | 2 |
| H | C(=O)R²⁴ | —(CH₂)₆CH₃ | H | 3 |
| H | C(=O)R²⁴ | —(CH₂)₈CH₃ | H | 3 |
| H | C(=O)R²⁴ | —(CH₂)₁₀CH₃ | H | 3 |
| H | C(=O)R²⁴ | —(CH₂)₁₂CH₃ | H | 3 |
| H | C(=O)R²⁴ | —(CH₂)₁₄CH₃ | H | 3 |
| H | C(=O)R²⁴ | —(CH₂)₁₆CH₃ | H | 3 |
| H | C(=O)R²⁴ | —(CH₂)₁₈CH₃ | H | 3 |
| H | C(=O)R²⁴ | —(CH₂)₂₀CH₃ | H | 3 |
| H | C(=O)R²⁴ | —(CH₂)₂₂CH₃ | H | 3 |
| H | C(=O)R²⁴ | —(CH₂)₂₄CH₃ | H | 3 |
| H | C(=O)R²⁴ | —(CH₂)₇CH=CH(CH₂)₃CH₃ | H | 3 |
| H | C(=O)R²⁴ | —(CH₂)₇CH=CHCH₂CH=CH(CH₂)₄CH₃ | H | 3 |
| H | C(=O)R²⁴ | —(CH₂)₇CH=CH(CH₂)₇CH₃ | H | 3 |
| H | C(=O)R²⁴ | —(CH₂)₇CH=CHCH₂CH=CH(CH₂)₄CH₃ | H | 3 |
| H | C(=O)R²⁴ | —(CH₂)₇CH=CH(CH₂)₇CH₃ | H | 3 |
| H | C(=O)R²⁴ | —(CH₂)₇CH=CHCH₂CH=CHCH₂CH=CHCH₂CH₃ | H | 3 |
| H | C(=O)R²⁴ | —(CH₂)₉CH=CH(CH₂)₅CH₃ | H | 3 |
| H | C(=O)R²⁴ | —(CH₂)₃CH=CHCH₂CH=CHCH₂CH=CHCH=CH(CH₂)₄CH₃ | H | 3 |
| H | C(=O)R²⁴ | —(CH₂)₁₁CH=CH(CH₂)₇CH₃ | H | 3 |
| H | C(=O)R²⁴ | —(CH₂)₃CH=CHCH₂CH=CHCH₂CH=CHCH₂CH=CHCH₂CH₃ | H | 3 |
| H | C(=O)R²⁴ | —(CH₂)₄CH=CHCH(CH₃)₂ | H | 3 |
| H | C(=O)R²⁴ | —(CH₂)₂CH=CHCH₂CH=CHCH₂CH=CHCH₂CH=CHCH₂CH=CHCH₂CH₃ | H | 3 |
| H | C(=O)R²⁴ | —(CH₂)₆CH₃ | CH₃ | 3 |
| H | C(=O)R²⁴ | —(CH₂)₈CH₃ | CH₃ | 3 |
| H | C(=O)R²⁴ | —(CH₂)₁₀CH₃ | CH₃ | 3 |
| H | C(=O)R²⁴ | —(CH₂)₁₂CH₃ | CH₃ | 3 |
| H | C(=O)R²⁴ | —(CH₂)₁₄CH₃ | CH₃ | 3 |
| H | C(=O)R²⁴ | —(CH₂)₁₆CH₃ | CH₃ | 3 |
| H | C(=O)R²⁴ | —(CH₂)₁₈CH₃ | CH₃ | 3 |
| H | C(=O)R²⁴ | —(CH₂)₂₀CH₃ | CH₃ | 3 |
| H | C(=O)R²⁴ | —(CH₂)₂₂CH₃ | CH₃ | 3 |
| H | C(=O)R²⁴ | —(CH₂)₂₄CH₃ | CH₃ | 3 |
| H | C(=O)R²⁴ | —(CH₂)₇CH=CH(CH₂)₃CH₃ | CH₃ | 3 |

TABLE 1-continued

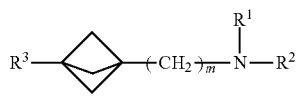

| R¹ | R² | R²⁴ | R³ | m |
|---|---|---|---|---|
| H | C(=O)R²⁴ | —(CH₂)₇CH=CHCH₂CH=CH(CH₂)₄CH₃ | CH₃ | 3 |
| H | C(=O)R²⁴ | —(CH₂)₇CH=CH(CH₂)₇CH₃ | CH₃ | 3 |
| H | C(=O)R²⁴ | —(CH₂)₇CH=CHCH₂CH=CH(CH₂)₄CH₃ | CH₃ | 3 |
| H | C(=O)R²⁴ | —(CH₂)₇CH=CH(CH₂)₇CH₃ | CH₃ | 3 |
| H | C(=O)R²⁴ | —(CH₂)₇CH=CHCH₂CH=CHCH₂CH=CHCH₂CH₃ | CH₃ | 3 |
| H | C(=O)R²⁴ | —(CH₂)₉CH=CH(CH₂)₅CH₃ | CH₃ | 3 |
| H | C(=O)R²⁴ | —(CH₂)₃CH=CHCH₂CH=CHCH₂CH=CHCH₂CH=CH(CH₂)₄CH₃ | CH₃ | 3 |
| H | C(=O)R²⁴ | —(CH₂)₁₁CH=CH(CH₂)₇CH₃ | CH₃ | 3 |
| H | C(=O)R²⁴ | —(CH₂)₃CH=CHCH₂CH=CHCH₂CH=CHCH₂CH=CHCH₂CH₃ | CH₃ | 3 |
| H | C(=O)R²⁴ | —(CH₂)₄CH=CHCH(CH₃)₂ | CH₃ | 3 |
| H | C(=O)R²⁴ | —(CH₂)₂CH=CHCH₂CH=CHCH₂CH=CHCH₂CH=CHCH₂CH=CHCH₂CH₃ | CH₃ | 3 |
| H | C(=O)R²⁴ | —(CH₂)₆CH₃ | CH(CH₃)₂ | 3 |
| H | C(=O)R²⁴ | —(CH₂)₈CH₃ | CH(CH₃)₂ | 3 |
| H | C(=O)R²⁴ | —(CH₂)₁₀CH₃ | CH(CH₃)₂ | 3 |
| H | C(=O)R²⁴ | —(CH₂)₁₂CH₃ | CH(CH₃)₂ | 3 |
| H | C(=O)R²⁴ | —(CH₂)₁₄CH₃ | CH(CH₃)₂ | 3 |
| H | C(=O)R²⁴ | —(CH₂)₁₆CH₃ | CH(CH₃)₂ | 3 |
| H | C(=O)R²⁴ | —(CH₂)₁₈CH₃ | CH(CH₃)₂ | 3 |
| H | C(=O)R²⁴ | —(CH₂)₂₀CH₃ | CH(CH₃)₂ | 3 |
| H | C(=O)R²⁴ | —(CH₂)₂₂CH₃ | CH(CH₃)₂ | 3 |
| H | C(=O)R²⁴ | —(CH₂)₂₄CH₃ | CH(CH₃)₂ | 3 |
| H | C(=O)R²⁴ | —(CH₂)₇CH=CH(CH₂)₃CH₃ | CH(CH₃)₂ | 3 |
| H | C(=O)R²⁴ | —(CH₂)₇CH=CHCH₂CH=CH(CH₂)₄CH₃ | CH(CH₃)₂ | 3 |
| H | C(=O)R²⁴ | —(CH₂)₇CH=CH(CH₂)₇CH₃ | CH(CH₃)₂ | 3 |
| H | C(=O)R²⁴ | —(CH₂)₇CH=CHCH₂CH=CH(CH₂)₄CH₃ | CH(CH₃)₂ | 3 |
| H | C(=O)R²⁴ | —(CH₂)₇CH=CH(CH₂)₇CH₃ | CH(CH₃)₂ | 3 |
| H | C(=O)R²⁴ | —(CH₂)₇CH=CHCH₂CH=CHCH₂CH=CHCH₂CH₃ | CH(CH₃)₂ | 3 |
| H | C(=O)R²⁴ | —(CH₂)₉CH=CH(CH₂)₅CH₃ | CH(CH₃)₂ | 3 |
| H | C(=O)R²⁴ | —(CH₂)₃CH=CHCH₂CH=CHCH₂CH=CHCH₂CH=CH(CH₂)₄CH₃ | CH(CH₃)₂ | 3 |
| H | C(=O)R²⁴ | —(CH₂)₁₁CH=CH(CH₂)₇CH₃ | CH(CH₃)₂ | 3 |
| H | C(=O)R²⁴ | —(CH₂)₃CH=CHCH₂CH=CHCH₂CH=CHCH₂CH=CHCH₂CH₃ | CH(CH₃)₂ | 3 |
| H | C(=O)R²⁴ | —(CH₂)₄CH=CHCH(CH₃)₂ | CH(CH₃)₂ | 3 |
| H | C(=O)R²⁴ | —(CH₂)₂CH=CHCH₂CH=CHCH₂CH=CHCH₂CH=CHCH₂CH=CHCH₂CH₃ | CH(CH₃)₂ | 3 |
| H | C(=O)R²⁴ | —(CH₂)₆CH₃ | C(CH₃)₃ | 3 |
| H | C(=O)R²⁴ | —(CH₂)₈CH₃ | C(CH₃)₃ | 3 |
| H | C(=O)R²⁴ | —(CH₂)₁₀CH₃ | C(CH₃)₃ | 3 |
| H | C(=O)R²⁴ | —(CH₂)₁₂CH₃ | C(CH₃)₃ | 3 |
| H | C(=O)R²⁴ | —(CH₂)₁₄CH₃ | C(CH₃)₃ | 3 |
| H | C(=O)R²⁴ | —(CH₂)₁₆CH₃ | C(CH₃)₃ | 3 |
| H | C(=O)R²⁴ | —(CH₂)₁₈CH₃ | C(CH₃)₃ | 3 |
| H | C(=O)R²⁴ | —(CH₂)₂₀CH₃ | C(CH₃)₃ | 3 |
| H | C(=O)R²⁴ | —(CH₂)₂₂CH₃ | C(CH₃)₃ | 3 |
| H | C(=O)R²⁴ | —(CH₂)₂₄CH₃ | C(CH₃)₃ | 3 |
| H | C(=O)R²⁴ | —(CH₂)₇CH=CH(CH₂)₃CH₃ | C(CH₃)₃ | 3 |
| H | C(=O)R²⁴ | —(CH₂)₇CH=CHCH₂CH=CH(CH₂)₄CH₃ | C(CH₃)₃ | 3 |
| H | C(=O)R²⁴ | —(CH₂)₇CH=CH(CH₂)₇CH₃ | C(CH₃)₃ | 3 |
| H | C(=O)R²⁴ | —(CH₂)₇CH=CHCH₂CH=CH(CH₂)₄CH₃ | C(CH₃)₃ | 3 |
| H | C(=O)R²⁴ | —(CH₂)₇CH=CH(CH₂)₇CH₃ | C(CH₃)₃ | 3 |
| H | C(=O)R²⁴ | —(CH₂)₇CH=CHCH₂CH=CHCH₂CH=CHCH₂CH₃ | C(CH₃)₃ | 3 |
| H | C(=O)R²⁴ | —(CH₂)₉CH=CH(CH₂)₅CH₃ | C(CH₃)₃ | 3 |
| H | C(=O)R²⁴ | —(CH₂)₃CH=CHCH₂CH=CHCH₂CH=CHCH₂CH=CH(CH₂)₄CH₃ | C(CH₃)₃ | |
| H | C(=O)R²⁴ | —(CH₂)₁₁CH=CH(CH₂)₇CH₃ | C(CH₃)₃ | 3 |
| H | C(=O)R²⁴ | —(CH₂)₃CH=CHCH₂CH=CHCH₂CH=CHCH₂CH=CHCH₂CH₃ | C(CH₃)₃ | 3 |
| H | C(=O)R²⁴ | —(CH₂)₄CH=CHCH(CH₃)₂ | C(CH₃)₃ | 3 |
| H | C(=O)R²⁴ | —(CH₂)₂CH=CHCH₂CH=CHCH₂CH=CHCH₂CH=CHCH₂CH=CHCH₂CH₃ | C(CH₃)₃ | 3 |
| H | C(=O)R²⁴ | —(CH₂)₆CH₃ | cyclopropyl | 3 |
| H | C(=O)R²⁴ | —(CH₂)₈CH₃ | cyclopropyl | 3 |
| H | C(=O)R²⁴ | —(CH₂)₁₀CH₃ | cyclopropyl | 3 |
| H | C(=O)R²⁴ | —(CH₂)₁₂CH₃ | cyclopropyl | 3 |
| H | C(=O)R²⁴ | —(CH₂)₁₄CH₃ | cyclopropyl | 3 |
| H | C(=O)R²⁴ | —(CH₂)₁₆CH₃ | cyclopropyl | 3 |
| H | C(=O)R²⁴ | —(CH₂)₁₈CH₃ | cyclopropyl | 3 |
| H | C(=O)R²⁴ | —(CH₂)₂₀CH₃ | cyclopropyl | 3 |

TABLE 1-continued

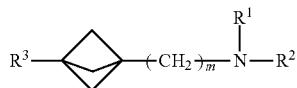

| R¹ | R² | R²⁴ | R³ | m |
|---|---|---|---|---|
| H | C(=O)R²⁴ | —(CH₂)₂₂CH₃ | cyclopropyl | 3 |
| H | C(=O)R²⁴ | —(CH₂)₂₄CH₃ | cyclopropyl | 3 |
| H | C(=O)R²⁴ | —(CH₂)₇CH=CH(CH₂)₃CH₃ | cyclopropyl | 3 |
| H | C(=O)R²⁴ | —(CH₂)₇CH=CHCH₂CH=CH(CH₂)₄CH₃ | cyclopropyl | 3 |
| H | C(=O)R²⁴ | —(CH₂)₇CH=CH(CH₂)₇CH₃ | cyclopropyl | 3 |
| H | C(=O)R²⁴ | —(CH₂)₇CH=CHCH₂CH=CH(CH₂)₄CH₃ | cyclopropyl | 3 |
| H | C(=O)R²⁴ | —(CH₂)₇CH=CH(CH₂)₇CH₃ | cyclopropyl | 3 |
| H | C(=O)R²⁴ | —(CH₂)₇CH=CHCH₂CH=CHCH₂CH=CHCH₂CH₃ | cyclopropyl | 3 |
| H | C(=O)R²⁴ | —(CH₂)₉CH=CH(CH₂)₅CH₃ | cyclopropyl | 3 |
| H | C(=O)R²⁴ | —(CH₂)₃CH=CHCH₂CH=CHCH₂CH=CHCH₂CH=CH(CH₂)₄CH₃ | cyclopropyl | 3 |
| H | C(=O)R²⁴ | —(CH₂)₁₁CH=CH(CH₂)₇CH₃ | cyclopropyl | 3 |
| H | C(=O)R²⁴ | —(CH₂)₃CH=CHCH₂CH=CHCH₂CH=CHCH=CHCH₂CH=CHCH₂CH₃ | cyclopropyl | 3 |
| H | C(=O)R²⁴ | —(CH₂)₄CH=CHCH(CH₃)₂ | cyclopropyl | 3 |
| H | C(=O)R²⁴ | —(CH₂)₂CH=CHCH₂CH=CHCH₂CH=CHCH=CHCH₂CH=CHCH₂CH₃ | cyclopropyl | 3 |
| H | C(=O)R²⁴ | —(CH₂)₆CH₃ | Cl | 3 |
| H | C(=O)R²⁴ | —(CH₂)₈CH₃ | Cl | 3 |
| H | C(=O)R²⁴ | —(CH₂)₁₀CH₃ | Cl | 3 |
| H | C(=O)R²⁴ | —(CH₂)₁₂CH₃ | Cl | 3 |
| H | C(=O)R²⁴ | —(CH₂)₁₄CH₃ | Cl | 3 |
| H | C(=O)R²⁴ | —(CH₂)₁₆CH₃ | Cl | 3 |
| H | C(=O)R²⁴ | —(CH₂)₁₈CH₃ | Cl | 3 |
| H | C(=O)R²⁴ | —(CH₂)₂₀CH₃ | Cl | 3 |
| H | C(=O)R²⁴ | —(CH₂)₂₂CH₃ | Cl | 3 |
| H | C(=O)R²⁴ | —(CH₂)₂₄CH₃ | Cl | 3 |
| H | C(=O)R²⁴ | —(CH₂)₇CH=CH(CH₂)₃CH₃ | Cl | 3 |
| H | C(=O)R²⁴ | —(CH₂)₇CH=CHCH₂CH=CH(CH₂)₄CH₃ | Cl | 3 |
| H | C(=O)R²⁴ | —(CH₂)₇CH=CH(CH₂)₇CH₃ | Cl | 3 |
| H | C(=O)R²⁴ | —(CH₂)₇CH=CHCH₂CH=CH(CH₂)₄CH₃ | Cl | 3 |
| H | C(=O)R²⁴ | —(CH₂)₇CH=CH(CH₂)₇CH₃ | Cl | 3 |
| H | C(=O)R²⁴ | —(CH₂)₇CH=CHCH₂CH=CHCH₂CH=CHCH₂CH₃ | Cl | 3 |
| H | C(=O)R²⁴ | —(CH₂)₉CH=CH(CH₂)₅CH₃ | Cl | 3 |
| H | C(=O)R²⁴ | —(CH₂)₃CH=CHCH₂CH=CHCH₂CH=CHCH₂CH=CH(CH₂)₄CH₃ | Cl | 3 |
| H | C(=O)R²⁴ | —(CH₂)₁₁CH=CH(CH₂)₇CH₃ | Cl | 3 |
| H | C(=O)R²⁴ | —(CH₂)₃CH=CHCH₂CH=CHCH₂CH=CHCH=CHCH₂CH=CHCH₂CH₃ | Cl | 3 |
| H | C(=O)R²⁴ | —(CH₂)₄CH=CHCH(CH₃)₂ | Cl | 3 |
| H | C(=O)R²⁴ | —(CH₂)₂CH=CHCH₂CH=CHCH₂CH=CHCH=CHCH₂CH=CHCH₂CH₃ | Cl | 3 |
| H | C(=O)R²⁴ | —(CH₂)₆CH₃ | F | 3 |
| H | C(=O)R²⁴ | —(CH₂)₈CH₃ | F | 3 |
| H | C(=O)R²⁴ | —(CH₂)₁₀CH₃ | F | 3 |
| H | C(=O)R²⁴ | —(CH₂)₁₂CH₃ | F | 3 |
| H | C(=O)R²⁴ | —(CH₂)₁₄CH₃ | F | 3 |
| H | C(=O)R²⁴ | —(CH₂)₁₆CH₃ | F | 3 |
| H | C(=O)R²⁴ | —(CH₂)₁₈CH₃ | F | 3 |
| H | C(=O)R²⁴ | —(CH₂)₂₀CH₃ | F | 3 |
| H | C(=O)R²⁴ | —(CH₂)₂₂CH₃ | F | 3 |
| H | C(=O)R²⁴ | —(CH₂)₂₄CH₃ | F | 3 |
| H | C(=O)R²⁴ | —(CH₂)₇CH=CH(CH₂)₃CH₃ | F | 3 |
| H | C(=O)R²⁴ | —(CH₂)₇CH=CHCH₂CH=CH(CH₂)₄CH₃ | F | 3 |
| H | C(=O)R²⁴ | —(CH₂)₇CH=CH(CH₂)₇CH₃ | F | 3 |
| H | C(=O)R²⁴ | —(CH₂)₇CH=CHCH₂CH=CH(CH₂)₄CH₃ | F | 3 |
| H | C(=O)R²⁴ | —(CH₂)₇CH=CH(CH₂)₇CH₃ | F | 3 |
| H | C(=O)R²⁴ | —(CH₂)₇CH=CHCH₂CH=CHCH₂CH=CHCH₂CH₃ | F | 3 |
| H | C(=O)R²⁴ | —(CH₂)₉CH=CH(CH₂)₅CH₃ | F | 3 |
| H | C(=O)R²⁴ | —(CH₂)₃CH=CHCH₂CH=CHCH₂CH=CHCH₂CH=CH(CH₂)₄CH₃ | F | 3 |
| H | C(=O)R²⁴ | —(CH₂)₁₁CH=CH(CH₂)₇CH₃ | F | 3 |
| H | C(=O)R²⁴ | —(CH₂)₃CH=CHCH₂CH=CHCH₂CH=CHCH=CHCH₂CH=CHCH₂CH₃ | F | 3 |
| H | C(=O)R²⁴ | —(CH₂)₄CH=CHCH(CH₃)₂ | F | 3 |
| H | C(=O)R²⁴ | —(CH₂)₂CH=CHCH₂CH=CHCH₂CH=CHCH=CHCH₂CH=CHCH₂CH₃ | F | 3 |
| H | C(=O)R²⁴ | —(CH₂)₆CH₃ | S(O)₂CH₃ | 3 |
| H | C(=O)R²⁴ | —(CH₂)₈CH₃ | S(O)₂CH₃ | 3 |
| H | C(=O)R²⁴ | —(CH₂)₁₀CH₃ | S(O)₂CH₃ | 3 |
| H | C(=O)R²⁴ | —(CH₂)₁₂CH₃ | S(O)₂CH₃ | 3 |
| H | C(=O)R²⁴ | —(CH₂)₁₄CH₃ | S(O)₂CH₃ | 3 |

TABLE 1-continued

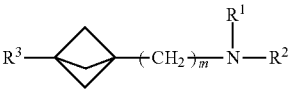

| R¹ | R² | R²⁴ | R³ | m |
|---|---|---|---|---|
| H | C(=O)R²⁴ | —(CH₂)₁₆CH₃ | S(O)₂CH₃ | 3 |
| H | C(=O)R²⁴ | —(CH₂)₁₈CH₃ | S(O)₂CH₃ | 3 |
| H | C(=O)R²⁴ | —(CH₂)₂₀CH₃ | S(O)₂CH₃ | 3 |
| H | C(=O)R²⁴ | —(CH₂)₂₂CH₃ | S(O)₂CH₃ | 3 |
| H | C(=O)R²⁴ | —(CH₂)₂₄CH₃ | S(O)₂CH₃ | 3 |
| H | C(=O)R²⁴ | —(CH₂)₇CH=CH(CH₂)₃CH₃ | S(O)₂CH₃ | 3 |
| H | C(=O)R²⁴ | —(CH₂)₇CH=CHCH₂CH=CH(CH₂)₄CH₃ | S(O)₂CH₃ | 3 |
| H | C(=O)R²⁴ | —(CH₂)₇CH=CH(CH₂)₇CH₃ | S(O)₂CH₃ | 3 |
| H | C(=O)R²⁴ | —(CH₂)₇CH=CHCH₂CH=CH(CH₂)₄CH₃ | S(O)₂CH₃ | 3 |
| H | C(=O)R²⁴ | —(CH₂)₇CH=CH(CH₂)₇CH₃ | S(O)₂CH₃ | 3 |
| H | C(=O)R²⁴ | —(CH₂)₇CH=CHCH₂CH=CHCH₂CH=CHCH₂CH₃ | S(O)₂CH₃ | 3 |
| H | C(=O)R²⁴ | —(CH₂)₉CH=CH(CH₂)₅CH₃ | S(O)₂CH₃ | 3 |
| H | C(=O)R²⁴ | —(CH₂)₃CH=CHCH₂CH=CHCH₂CH=CHCH₂CH=CH(CH₂)₄CH₃ | S(O)₂CH₃ | 3 |
| H | C(=O)R²⁴ | —(CH₂)₁₁CH=CH(CH₂)₇CH₃ | S(O)₂CH₃ | 3 |
| H | C(=O)R²⁴ | —(CH₂)₃CH=CHCH₂CH=CHCH₂CH=CHCH=CHCH₂CH=CHCH₂CH₃ | S(O)₂CH₃ | 3 |
| H | C(=O)R²⁴ | —(CH₂)₄CH=CHCH(CH₃)₂ | S(O)₂CH₃ | 3 |
| H | C(=O)R²⁴ | —(CH₂)₂CH=CHCH₂CH=CHCH₂CH=CHCH₂CH=CHCH₂CH=CHCH₂CH₃ | S(O)₂CH₃ | 3 |
| H | C(=O)R²⁴ | —(CH₂)₆CH₃ | CF₃ | 3 |
| H | C(=O)R²⁴ | —(CH₂)₈CH₃ | CF₃ | 3 |
| H | C(=O)R²⁴ | —(CH₂)₁₀CH₃ | CF₃ | 3 |
| H | C(=O)R²⁴ | —(CH₂)₁₂CH₃ | CF₃ | 3 |
| H | C(=O)R²⁴ | —(CH₂)₁₄CH₃ | CF₃ | 3 |
| H | C(=O)R²⁴ | —(CH₂)₁₆CH₃ | CF₃ | 3 |
| H | C(=O)R²⁴ | —(CH₂)₁₈CH₃ | CF₃ | 3 |
| H | C(=O)R²⁴ | —(CH₂)₂₀CH₃ | CF₃ | 3 |
| H | C(=O)R²⁴ | —(CH₂)₂₂CH₃ | CF₃ | 3 |
| H | C(=O)R²⁴ | —(CH₂)₂₄CH₃ | CF₃ | 3 |
| H | C(=O)R²⁴ | —(CH₂)₇CH=CH(CH₂)₃CH₃ | CF₃ | 3 |
| H | C(=O)R²⁴ | —(CH₂)₇CH=CHCH₂CH=CH(CH₂)₄CH₃ | CF₃ | 3 |
| H | C(=O)R²⁴ | —(CH₂)₇CH=CH(CH₂)₇CH₃ | CF₃ | 3 |
| H | C(=O)R²⁴ | —(CH₂)₇CH=CHCH₂CH=CH(CH₂)₄CH₃ | CF₃ | 3 |
| H | C(=O)R²⁴ | —(CH₂)₇CH=CH(CH₂)₇CH₃ | CF₃ | 3 |
| H | C(=O)R²⁴ | —(CH₂)₇CH=CHCH₂CH=CHCH₂CH=CHCH₂CH₃ | CF₃ | 3 |
| H | C(=O)R²⁴ | —(CH₂)₉CH=CH(CH₂)₅CH₃ | CF₃ | 3 |
| H | C(=O)R²⁴ | —(CH₂)₃CH=CHCH₂CH=CHCH₂CH=CHCH₂CH=CH(CH₂)₄CH₃ | CF₃ | 3 |
| H | C(=O)R²⁴ | —(CH₂)₁₁CH=CH(CH₂)₇CH₃ | CF₃ | 3 |
| H | C(=O)R²⁴ | —(CH₂)₃CH=CHCH₂CH=CHCH₂CH=CHCH=CHCH₂CH=CHCH₂CH₃ | CF₃ | 3 |
| H | C(=O)R²⁴ | —(CH₂)₄CH=CHCH(CH₃)₂ | CF₃ | 3 |
| H | C(=O)R²⁴ | —(CH₂)₂CH=CHCH₂CH=CHCH₂CH=CHCH₂CH=CHCH₂CH=CHCH₂CH₃ | CF₃ | 3 |
| H | C(=O)R²⁴ | —(CH₂)₆CH₃ | CHF₂ | 3 |
| H | C(=O)R²⁴ | —(CH₂)₈CH₃ | CHF₂ | 3 |
| H | C(=O)R²⁴ | —(CH₂)₁₀CH₃ | CHF₂ | 3 |
| H | C(=O)R²⁴ | —(CH₂)₁₂CH₃ | CHF₂ | 3 |
| H | C(=O)R²⁴ | —(CH₂)₁₄CH₃ | CHF₂ | 3 |
| H | C(=O)R²⁴ | —(CH₂)₁₆CH₃ | CHF₂ | 3 |
| H | C(=O)R²⁴ | —(CH₂)₁₈CH₃ | CHF₂ | 3 |
| H | C(=O)R²⁴ | —(CH₂)₂₀CH₃ | CHF₂ | 3 |
| H | C(=O)R²⁴ | —(CH₂)₂₂CH₃ | CHF₂ | 3 |
| H | C(=O)R²⁴ | —(CH₂)₂₄CH₃ | CHF₂ | 3 |
| H | C(=O)R²⁴ | —(CH₂)₇CH=CH(CH₂)₃CH₃ | CHF₂ | 3 |
| H | C(=O)R²⁴ | —(CH₂)₇CH=CHCH₂CH=CH(CH₂)₄CH₃ | CHF₂ | 3 |
| H | C(=O)R²⁴ | —(CH₂)₇CH=CH(CH₂)₇CH₃ | CHF₂ | 3 |
| H | C(=O)R²⁴ | —(CH₂)₇CH=CHCH₂CH=CH(CH₂)₄CH₃ | CHF₂ | 3 |
| H | C(=O)R²⁴ | —(CH₂)₇CH=CH(CH₂)₇CH₃ | CHF₂ | 3 |
| H | C(=O)R²⁴ | —(CH₂)₇CH=CHCH₂CH=CHCH₂CH=CHCH₂CH₃ | CHF₂ | 3 |
| H | C(=O)R²⁴ | —(CH₂)₉CH=CH(CH₂)₅CH₃ | CHF₂ | 3 |
| H | C(=O)R²⁴ | —(CH₂)₃CH=CHCH₂CH=CHCH₂CH=CHCH₂CH=CH(CH₂)₄CH₃ | CHF₂ | 3 |
| H | C(=O)R²⁴ | —(CH₂)₁₁CH=CH(CH₂)₇CH₃ | CHF₂ | 3 |
| H | C(=O)R²⁴ | —(CH₂)₃CH=CHCH₂CH=CHCH₂CH=CHCH=CHCH₂CH=CHCH₂CH₃ | CHF₂ | 3 |
| H | C(=O)R²⁴ | —(CH₂)₄CH=CHCH(CH₃)₂ | CHF₂ | 3 |
| H | C(=O)R²⁴ | —(CH₂)₂CH=CHCH₂CH=CHCH₂CH=CHCH₂CH=CHCH₂CH=CHCH₂CH₃ | CHF₂ | 3 |
| H | C(=O)R²⁴ | —(CH₂)₆CH₃ | CF₂CH₃ | 3 |
| H | C(=O)R²⁴ | —(CH₂)₈CH₃ | CF₂CH₃ | 3 |

TABLE 1-continued

| R¹ | R² | R²⁴ | R³ | m |
|---|---|---|---|---|
| H | C(=O)R²⁴ | —(CH₂)₁₀CH₃ | CF₂CH₃ | 3 |
| H | C(=O)R²⁴ | —(CH₂)₁₂CH₃ | CF₂CH₃ | 3 |
| H | C(=O)R²⁴ | —(CH₂)₁₄CH₃ | CF₂CH₃ | 3 |
| H | C(=O)R²⁴ | —(CH₂)₁₆CH₃ | CF₂CH₃ | 3 |
| H | C(=O)R²⁴ | —(CH₂)₁₈CH₃ | CF₂CH₃ | 3 |
| H | C(=O)R²⁴ | —(CH₂)₂₀CH₃ | CF₂CH₃ | 3 |
| H | C(=O)R²⁴ | —(CH₂)₂₂CH₃ | CF₂CH₃ | 3 |
| H | C(=O)R²⁴ | —(CH₂)₂₄CH₃ | CF₂CH₃ | 3 |
| H | C(=O)R²⁴ | —(CH₂)₇CH=CH(CH₂)₃CH₃ | CF₂CH₃ | 3 |
| H | C(=O)R²⁴ | —(CH₂)₇CH=CHCH₂CH=CH(CH₂)₄CH₃ | CF₂CH₃ | 3 |
| H | C(=O)R²⁴ | —(CH₂)₇CH=CH(CH₂)₇CH₃ | CF₂CH₃ | 3 |
| H | C(=O)R²⁴ | —(CH₂)₇CH=CHCH₂CH=CH(CH₂)₄CH₃ | CF₂CH₃ | 3 |
| H | C(=O)R²⁴ | —(CH₂)₇CH=CH(CH₂)₇CH₃ | CF₂CH₃ | 3 |
| H | C(=O)R²⁴ | —(CH₂)₇CH=CHCH₂CH=CHCH₂CH=CHCH₂CH₃ | CF₂CH₃ | 3 |
| H | C(=O)R²⁴ | —(CH₂)₉CH=CH(CH₂)₅CH₃ | CF₂CH₃ | 3 |
| H | C(=O)R²⁴ | —(CH₂)₃CH=CHCH₂CH=CHCH₂CH=CHCH₂CH=CH(CH₂)₄CH₃ | CF₂CH₃ | 3 |
| H | C(=O)R²⁴ | —(CH₂)₁₁CH=CH(CH₂)₇CH₃ | CF₂CH₃ | 3 |
| H | C(=O)R²⁴ | —(CH₂)₃CH=CHCH₂CH=CHCH₂CH=CHCH₂CH=CHCH₂CH₃ | CF₂CH₃ | 3 |
| H | C(=O)R²⁴ | —(CH₂)₄CH=CHCH(CH₃)₂ | CF₂CH₃ | 3 |
| H | C(=O)R²⁴ | —(CH₂)₂CH=CHCH₂CH=CHCH₂CH=CHCH₂CH=CHCH₂CH=CHCH₂CH₃ | CF₂CH₃ | 3 |
| H | C(=O)R²⁴ | —(CH₂)₆CH₃ | C(CH₃)₂OH | 3 |
| H | C(=O)R²⁴ | —(CH₂)₈CH₃ | C(CH₃)₂OH | 3 |
| H | C(=O)R²⁴ | —(CH₂)₁₀CH₃ | C(CH₃)₂OH | 3 |
| H | C(=O)R²⁴ | —(CH₂)₁₂CH₃ | C(CH₃)₂OH | 3 |
| H | C(=O)R²⁴ | —(CH₂)₁₄CH₃ | C(CH₃)₂OH | 3 |
| H | C(=O)R²⁴ | —(CH₂)₁₆CH₃ | C(CH₃)₂OH | 3 |
| H | C(=O)R²⁴ | —(CH₂)₁₈CH₃ | C(CH₃)₂OH | 3 |
| H | C(=O)R²⁴ | —(CH₂)₂₀CH₃ | C(CH₃)₂OH | 3 |
| H | C(=O)R²⁴ | —(CH₂)₂₂CH₃ | C(CH₃)₂OH | 3 |
| H | C(=O)R²⁴ | —(CH₂)₂₄CH₃ | C(CH₃)₂OH | 3 |
| H | C(=O)R²⁴ | —(CH₂)₇CH=CH(CH₂)₃CH₃ | C(CH₃)₂OH | 3 |
| H | C(=O)R²⁴ | —(CH₂)₇CH=CHCH₂CH=CH(CH₂)₄CH₃ | C(CH₃)₂OH | 3 |
| H | C(=O)R²⁴ | —(CH₂)₇CH=CH(CH₂)₇CH₃ | C(CH₃)₂OH | 3 |
| H | C(=O)R²⁴ | —(CH₂)₇CH=CHCH₂CH=CH(CH₂)₄CH₃ | C(CH₃)₂OH | 3 |
| H | C(=O)R²⁴ | —(CH₂)₇CH=CH(CH₂)₇CH₃ | C(CH₃)₂OH | 3 |
| H | C(=O)R²⁴ | —(CH₂)₇CH=CHCH₂CH=CHCH₂CH=CHCH₂CH₃ | C(CH₃)₂OH | 3 |
| H | C(=O)R²⁴ | —(CH₂)₉CH=CH(CH₂)₅CH₃ | C(CH₃)₂OH | 3 |
| H | C(=O)R²⁴ | —(CH₂)₃CH=CHCH₂CH=CHCH₂CH=CHCH₂CH=CH(CH₂)₄CH₃ | C(CH₃)₂OH | 3 |
| H | C(=O)R²⁴ | —(CH₂)₁₁CH=CH(CH₂)₇CH₃ | C(CH₃)₂OH | 3 |
| H | C(=O)R²⁴ | —(CH₂)₃CH=CHCH₂CH=CHCH₂CH=CHCH₂CH=CHCH₂CH₃ | C(CH₃)₂OH | 3 |
| H | C(=O)R²⁴ | —(CH₂)₄CH=CHCH(CH₃)₂ | C(CH₃)₂OH | 3 |
| H | C(=O)R²⁴ | —(CH₂)₂CH=CHCH₂CH=CHCH₂CH=CHCH₂CH=CHCH₂CH=CHCH₂CH₃ | C(CH₃)₂OH | 3 |

In some embodiments, when m is 0, then R² is H. In some embodiments, when m is 0, R¹ and R² are each H, then R³ may not be t-butyl. In some embodiments, a compound of Formula (I), or a pharmaceutically salt thereof may not be

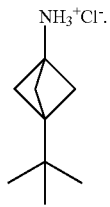

In some embodiments, when m is 0, R¹ is H, and R² is H, then R³ may not be selected from H, CH₃, F, I, hydroxy, unsubstituted phenyl, an optionally substituted bicyclo[1.1.1]pentane and CF₃. In some embodiments, when m is 0, R¹ is CH₃, and R² is H, then R³ may not be hydroxy. In some embodiments, a compound of Formula (I) cannot be N,N-diethyl-alpha-methyl-bicyclo[1.1.1]pentane-1-methanamine, or a pharmaceutically acceptable salt thereof. In some embodiments, when m is 0 and R¹ is H, then R² may not be H. In some embodiments, when m is 1, A¹ is CH₂, R³ is H and R² is hydrogen, then R¹ may not be hydrogen.

In some embodiments, R¹ cannot be H. In other embodiments, R¹ cannot be D. In still other embodiments, R¹ cannot be a substituted C₁₋₆ alkyl. In yet still other embodiments, R¹ cannot be an unsubstituted C₁₋₆ alkyl. In some embodiments, R¹ cannot be a substituted C₁₋₆ haloalkyl. In other embodiments, R¹ cannot be an unsubstituted C₁₋₆ haloalkyl.

In some embodiments, R² cannot be H. In some embodiments, R² cannot be an amino group directly attached to the bicyclopentane ring. In other embodiments, R² cannot be an amino group attached to the bicyclopentane ring through an optionally substituted methylene. In some embodiments, $R^2$ cannot be a mono-substituted group directly attached to the bicyclopentane ring. In other embodiments, $R^2$ cannot be a mono-substituted group attached to the bicyclopentane ring through an optionally substituted methylene.

In some embodiments, $R^2$ cannot be $C(=O)R^{2A}$. In some embodiments, $R^2$ cannot be an N-amido group directly attached to the bicyclopentane ring. In other embodiments, $R^2$ cannot be an N-amido group attached to the bicyclopentane ring through an optionally substituted methylene.

In some embodiments, $R^{2A}$ cannot be H. In other embodiments, $R^{2A}$ cannot be D. In still other embodiments, $R^{2A}$ cannot be a substituted $C_{1-30}$ alkyl. In yet still other embodiments, $R^{2A}$ cannot be an unsubstituted $C_{1-30}$ alkyl.

In some embodiments, $R^{2A}$ cannot be a substituted $C_{2-30}$ alkenyl. In other embodiments, $R^{2A}$ cannot be an unsubstituted $C_{2-30}$ alkenyl. In still other embodiments, $R^{2A}$ cannot be a substituted $C_{2-30}$ alkynyl. In yet still other embodiments, $R^{2A}$ cannot be an unsubstituted $C_{2-30}$ alkynyl.

In some embodiments, $R^{2A}$ cannot be a substituted $C_{3-30}$ cycloalkyl. In other embodiments, $R^{2A}$ cannot be an unsubstituted $C_{3-30}$ cycloalkyl. In still other embodiments, $R^{2A}$ cannot be a substituted $C_{3-30}$ cycloalkenyl. In yet still other embodiments, $R^{2A}$ cannot be an unsubstituted $C_{3-30}$ cycloalkenyl. In some embodiments, $R^{2A}$ cannot be a substituted $C_{8-30}$ cycloalkynyl. In some embodiments, $R^{2A}$ cannot be an unsubstituted $C_{8-30}$ cycloalkynyl. In some embodiments, a cycloalkyl, a cycloalkenyl and/or a cycloalkynyl can be mono-cyclic. In other embodiments, a cycloalkyl, a cycloalkenyl and a cycloalkynyl can be bi-cyclic or tri-cyclic. As described herein, the rings of a multi-cyclic cycloalkyl, cycloalkenyl and cycloalkynyl can be joined together in a fused, bridged and/or spiro fashion.

In some embodiments, $R^{2A}$ cannot be a substituted $C_{6-30}$ aryl. In other embodiments, $R^{2A}$ cannot be an unsubstituted $C_{6-30}$ aryl. In some embodiments, $R^{2A}$ cannot be a substituted or unsubstituted phenyl.

In some embodiments, $R^{2A}$ cannot be a substituted heteroaryl. In other embodiments, $R^{2A}$ cannot be an unsubstituted heteroaryl. In some embodiments, $R^{2A}$ cannot be a substituted or unsubstituted mono-cyclic heteroaryl. In some embodiments, $R^{2A}$ cannot be a substituted or unsubstituted multi-cyclic heteroaryl, such as, a substituted or unsubstituted bi-cyclic heteroaryl.

In some embodiments, $R^{2A}$ cannot be a substituted heterocyclyl. In other embodiments, $R^{2A}$ cannot be an unsubstituted heterocyclyl. In some embodiments, $R^{2A}$ cannot be a substituted or unsubstituted mono-cyclic heterocyclyl. In some embodiments, $R^{2A}$ cannot be a substituted or unsubstituted multi-cyclic heterocyclyl (such as a bi-cyclic heterocyclyl).

In some embodiments, $R^{2A}$ cannot be a substituted aryl($C_{1-6}$ alkyl). In other embodiments, $R^{2A}$ cannot be an unsubstituted aryl($C_{1-6}$ alkyl). In some embodiments, $R^{2A}$ cannot be a substituted or unsubstituted benzyl. In some embodiments, $R^{2A}$ cannot be a substituted heteroaryl($C_{1-6}$ alkyl). In other embodiments, $R^{2A}$ cannot be an unsubstituted heteroaryl($C_{1-6}$ alkyl). In some embodiments, $R^{2A}$ cannot be a substituted or unsubstituted mono-cyclic heteroaryl($C_{1-6}$ alkyl). In some embodiments, $R^{2A}$ cannot be a substituted or unsubstituted multi-cyclic heteroaryl($C_{1-6}$ alkyl), such as a substituted or unsubstituted bi-cyclic heteroaryl($C_{1-6}$ alkyl). In some embodiments, $R^{2A}$ cannot be a substituted heterocyclyl($C_{1-6}$ alkyl). In other embodiments, $R^{2A}$ cannot be an unsubstituted heterocyclyl($C_{1-6}$ alkyl). In some embodiments, $R^{2A}$ cannot be a substituted or unsubstituted mono-cyclic heterocyclyl($C_{1-6}$ alkyl). In some embodiments, $R^{2A}$ cannot be a substituted or unsubstituted multi-cyclic heterocyclyl($C_{1-6}$ alkyl), for example, a substituted or unsubstituted bi-cyclic heterocyclyl($C_{1-6}$ alkyl).

In some embodiments, $R^{2A}$ cannot be a substituted $C_{1-8}$ haloalkyl. In other embodiments, $R^{2A}$ cannot be an unsubstituted $C_{1-8}$ haloalkyl. In some embodiments, $R^{2A}$ cannot be one or more of the following $CF_3$, $CHF_2$, $CH_2F$, $CH_2CF_3$, $CH_2CHF_2$ and $CH_2CH_2F$.

In some embodiments, $R^3$ cannot be H. In other embodiments, $R^3$ cannot be D. In still other embodiments, $R^3$ cannot be a halo. In some embodiments, $R^3$ cannot be F. In some embodiments, $R^3$ cannot Cl. In yet still other embodiments, $R^3$ cannot be hydroxy.

In some embodiments, $R^3$ cannot be a substituted $C_{1-8}$ alkyl. In other embodiments, $R^3$ cannot be an unsubstituted $C_{1-8}$ alkyl.

In some embodiments, $R^3$ cannot be a substituted $C_{2-8}$ alkenyl. In other embodiments, $R^3$ cannot be an unsubstituted $C_{2-8}$ alkenyl. In some embodiments, $R^3$ cannot be a substituted $C_{2-4}$ alkenyl. In other embodiments, $R^3$ cannot be an unsubstituted $C_{2-4}$ alkenyl. In some embodiments, $R^3$ cannot be a substituted $C_{2-8}$ alkynyl. In other embodiments, $R^3$ cannot be an unsubstituted $C_{2-8}$ alkynyl. In some embodiments, $R^3$ cannot be a substituted $C_{2-4}$ alkynyl. In other embodiments, $R^3$ cannot be an unsubstituted $C_{2-4}$ alkynyl.

In some embodiments, $R^3$ cannot be a substituted $C_{3-20}$ cycloalkyl. In other embodiments, $R^3$ cannot be an unsubstituted $C_{3-20}$ cycloalkyl. In some embodiments, $R^3$ cannot be a substituted $C_{3-20}$ cycloalkenyl. In other embodiments, $R^3$ cannot be an unsubstituted $C_{3-20}$ cycloalkenyl. In some embodiments, $R^3$ cannot be a substituted $C_{3-20}$ cycloalkynyl. In other embodiments, $R^3$ cannot be an unsubstituted $C_{3-20}$ cycloalkynyl.

In some embodiments, $R^3$ cannot be a substituted $C_{6-20}$ aryl. In other embodiments, $R^3$ cannot be an unsubstituted $C_{6-20}$ aryl. In some embodiments, $R^3$ cannot be an unsubstituted phenyl. In other embodiments, $R^3$ cannot be a substituted phenyl. In some embodiments, $R^3$ cannot be a substituted naphthyl. In some embodiments, $R^3$ cannot be an unsubstituted naphthyl.

In some embodiments, $R^3$ cannot be a substituted heteroaryl. In other embodiments, $R^3$ cannot be an unsubstituted heteroaryl. In some embodiments, $R^3$ cannot be a substituted mono-cyclic heteroaryl. In other embodiments, $R^3$ cannot be an unsubstituted mono-cyclic heteroaryl. In still other embodiments, $R^3$ cannot be a substituted multi-cyclic heteroaryl (for example, a substituted bi-cyclic heteroaryl). In yet still other embodiments, $R^3$ cannot be an unsubstituted multi-cyclic heteroaryl (for example, an unsubstituted bi-cyclic heteroaryl).

In some embodiments, $R^3$ cannot be a substituted heterocyclyl. In other embodiments, $R^3$ cannot be an unsubstituted heterocyclyl. In some embodiments, $R^3$ cannot be a substituted mono-cyclic heterocyclyl. In other embodiments, $R^3$ cannot be an unsubstituted mono-cyclic heterocyclyl. In still other embodiments, $R^3$ cannot be a substituted bi-cyclic heterocyclyl. In yet still other embodiments, $R^3$ cannot be an unsubstituted bi-cyclic heterocyclyl.

In some embodiments, $R^3$ cannot be a substituted aryl($C_{1-6}$ alkyl). In other embodiments, $R^3$ cannot be an unsubstituted aryl($C_{1-6}$ alkyl). In some embodiments, $R^3$ cannot be a substituted or unsubstituted benzyl.

In some embodiments, $R^3$ cannot be a substituted heteroaryl($C_{1-6}$ alkyl). In other embodiments, $R^3$ cannot be an unsubstituted heteroaryl($C_{1-6}$ alkyl). In still other embodiments, $R^3$ cannot be a substituted heterocyclyl($C_{1-6}$ alkyl). In other embodiments, $R^3$ cannot be an unsubstituted heterocyclyl($C_{1-6}$ alkyl). In some embodiments, $R^3$ cannot be a substituted mono-cyclic heterocyclyl($C_{1-6}$ alkyl). In other embodiments, $R^3$ cannot be an unsubstituted mono-cyclic heterocyclyl($C_{1-6}$ alkyl). In still other embodiments, $R^3$ cannot be a substituted multi-cyclic heterocyclyl($C_{1-6}$ alkyl), such as, a substituted bi-cyclic heterocyclyl($C_{1-6}$ alkyl). In yet still other embodiments, $R^3$ cannot be an unsubstituted multi-cyclic heterocyclyl($C_{1-6}$ alkyl), such as, an unsubstituted bi-cyclic heterocyclyl($C_{1-6}$ alkyl).

In some embodiments, $R^3$ cannot be a substituted $C_{1-8}$ haloalkyl. In other embodiments, $R^3$ cannot be an unsubstituted $C_{1-8}$ haloalkyl. In some embodiments, $R^3$ cannot be $CF_3$.

In some embodiments, $R^3$ cannot be a substituted sulfonyl. In other embodiments, $R^3$ cannot be an unsubstituted sulfonyl. In some embodiments, $R^3$ cannot be $SO_2R^{++}$, wherein $R^{++}$ can be hydrogen, an optionally substituted $C_{1-6}$ alkyl, an optionally substituted $C_{2-6}$ alkenyl, an optionally substituted $C_{3-6}$ cycloalkyl, an optionally substituted mono-cyclic aryl, an optionally substituted mono-cyclic heteroaryl or an optionally substituted mono-cyclic heterocyclyl. In other embodiments, $R^3$ cannot be $SO_2R^{++}$, wherein $R^{++}$ can be an unsubstituted $C_{1-6}$ alkyl, an unsubstituted $C_{2-6}$ alkenyl or an unsubstituted $C_{3-6}$ cycloalkyl. In some embodiments, $R^3$ cannot be $SO_2CH_3$.

In some embodiments, m cannot be 0. In other embodiments, m cannot be 1. In still other embodiments, m cannot be 2. In yet still other embodiments, m cannot be 3. In some embodiments, $R^4$ cannot be H. In other embodiments, $R^4$ cannot be D. In still other embodiments, $R^4$ cannot be an unsubstituted $C_{1-8}$ alkyl. In yet still other embodiments, $R^4$ cannot be an unsubstituted $C_{1-6}$ haloalkyl, such as $CF_3$, $CHF_2$ or $CH_2F$. In some embodiments, $R^5$ cannot be H. In other embodiments, $R^5$ cannot be D. In other embodiments, $R^5$ cannot be an unsubstituted $C_{1-8}$ alkyl. In yet still other embodiments, $R^5$ cannot be an unsubstituted $C_{1-6}$ haloalkyl, such as $CF_3$, $CHF_2$ or $CH_2F$. In some embodiments, $R^4$ and $R^5$ cannot be taken together to form an optionally substituted $C_{3-6}$ cycloalkyl.

Other embodiments disclosed herein relate to a compound of Formula (II), or a pharmaceutically acceptable salt thereof:

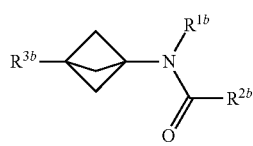

(II)

wherein: $R^{1b}$ can be H or $CH_3$; $R^{2b}$ can be $CH_2F$, $CHF_2$, $CF_3$ or an unsubstituted $C_{1-4}$ alkyl; and $R^{3b}$ can be H, $CH_2F$, $CHF_2$, $CF_3$, an unsubstituted $C_{1-4}$ alkyl or a hydro-substituted $C_{1-4}$ alkyl.

In some embodiments, $R^{1b}$ can be H. In other embodiments, $R^{1b}$ can be $CH_3$.

In some embodiments, $R^{2b}$ can be $CH_2F$. In other embodiments, $R^{2b}$ can be $CHF_2$. In still other embodiments, $R^{2b}$ can be $CF_3$. In yet still other embodiments, $R^{2b}$ can be an unsubstituted $C_{1-4}$ alkyl (such as methyl, ethyl, n-propyl, iso-propyl, n-butyl, iso-butyl and tert-butyl).

In some embodiments, $R^{3b}$ can be H. In other embodiments, $R^{3b}$ can be $CH_2F$. In still other embodiments, $R^{3b}$ can be $CHF_2$. In yet still other embodiments, $R^{3b}$ can be $CF_3$. In some embodiments, $R^{3b}$ can be an unsubstituted $C_{1-4}$ alkyl, for example, methyl, ethyl, n-propyl, iso-propyl, n-butyl, iso-butyl and tert-butyl. In other embodiments, $R^{3b}$ can be a hydro-substituted $C_{1-4}$ alkyl, for example, —$C(CH_3)_2OH$.

In some embodiments, $R^{1b}$ can be H or $CH_3$; $R^{2b}$ can be $CH_2F$, $CHF_2$, $CF_3$ or an unsubstituted $C_{1-4}$ alkyl; and $R^{3b}$ can be $CH_2F$, $CHF_2$ or $CF_3$. In some embodiments, $R^{1b}$ can be H or $CH_3$; $R^{2b}$ can be $CH_2F$, $CHF_2$, $CF_3$ or an unsubstituted $C_{1-4}$ alkyl; and $R^{3b}$ can be an unsubstituted $C_{1-4}$ alkyl or a hydro-substituted $C_{1-4}$ alkyl. In some embodiments, $R^{1b}$ can be H or $CH_3$; $R^{2b}$ can be an unsubstituted $C_{1-4}$ alkyl; and $R^{3b}$ can be an unsubstituted $C_{1-4}$ alkyl or a hydro-substituted $C_{1-4}$ alkyl. In some embodiments, $R^{1b}$ can be H or $CH_3$; $R^{2b}$ can be $CH_2F$, $CHF_2$ or $CF_3$; and $R^{3b}$ can be an unsubstituted $C_{1-4}$ alkyl or a hydro-substituted $C_{1-4}$ alkyl.

Examples of compounds of Formula (II) include, but are not limited to:

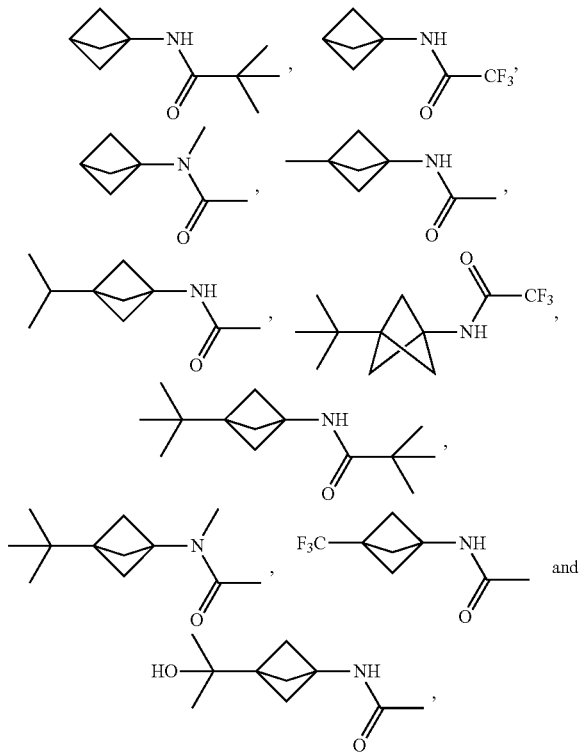

or a pharmaceutically acceptable salt of the foregoing.

Methods

The various compounds contemplated herein can be synthesized from known starting materials by various routes. Some suitable routes are illustrated in Schemes 1 and 2, with syntheses described in more detail in the following description and Examples.

Scheme 1

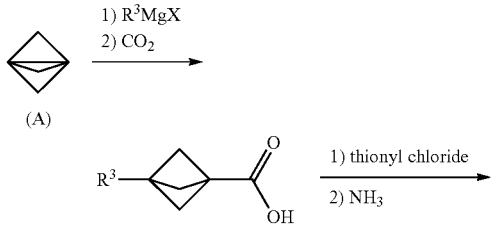

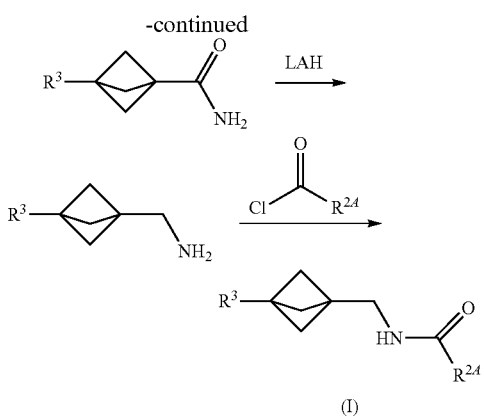

As shown in Scheme 1, compounds of Formula (I) can be prepared starting from a compound of Formula (A). The reaction of a compound of Formula (A) with a Grignard reagent followed by trapping with an electrophile such as carbon dioxide leads to a carboxylic acid compound. The carboxylic acid compound can be transformed to a carboxamide through an amide bond formation reaction with ammonia as the amine source. The carboxamide compound can be reduced using standard reducing reagents such as lithium aluminum hydride to give a primary amine. A second amide bond formation reaction with various reagents such as carboxylic acids, acid chlorides, or acid anhydrides leads to compounds of Formula (I).

For example, the reaction of [1.1.1]propellane with tert-butylmagnesium chloride followed by quenching the reaction with carbon dioxide gives 3-(tert-butyl)bicyclo[1.1.1]pentane-1-carboxylic acid. The conversion of 3-(tert-butyl) bicyclo[1.1.1]pentane-1-carboxylic acid to 3-(tert-butyl) bicyclo[1.1.1]pentane-1-carboxamide can be carried out using various amide bond formation reactions, for example by forming an acid chloride using reagents such as thionyl chloride or oxalyl chloride and then treating the formed 3-(tert-butyl)bicyclo[1.1.1]pentane-1-carbonyl chloride with ammonia. The reduction of 3-(tert-butyl)bicyclo[1.1.1]pentane-1-carboxamide can be carried out using such reagents as lithium aluminum hydride to give (3-(tert-butyl) bicyclo[1.1.1]pentan-1-yl)methanamine. The treatment of (3-(tert-butyl)bicyclo[1.1.1]pentan-1-yl)methanamine with reagents such as acetic anhydride or acetyl chloride gives N-((3-(tert-butyl)bicyclo[1.1.1]pentan-1-yl)methyl)acetamide.

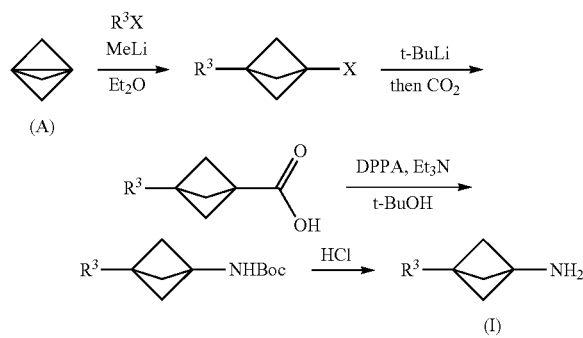

Compounds of Formula (I) can also be prepared starting from a compound of Formula (A) via the route shown in Scheme 2. Compound of Formula (A) can be reacted with methyl lithium and $R^3X$ in ether, wherein X is a suitable leaving group (for example, a halogen). A carboxylic acid moiety can be formed using t-butyl lithium and carbon dioxide. The carboxylic acid compound can be transformed and form a protected amine via a Curtius rearrangement using an azide, a reagent(s) that can provide the protecting group and a base, such as diphenylphosphoryl azide (DPPA), t-BuOH and triethyl amine, respectively. The protecting group can be removed using methods known to those skilled in the art, such as an acid. If desired and/or needed, the carboxylic acid compound can be converted to a carboxylic acid chloride before forming the protected amine.

Salts can be formed using methods known to those skilled in the art and described herein, for example, reacting an amine with a suitable acid (such as HCl).

Pharmaceutical Compositions

Some embodiments described herein relate to a pharmaceutical composition, that can include an effective amount of one or more compounds described herein (e.g., a compound of Formulae (I) and/or (II), or a pharmaceutically acceptable salt thereof) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory infection may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments provided herein relate to a method of treating a disease or condition that can include administering to a subject an effective amount of a compound of Formulae (I) and/or (II), or a pharmaceutically acceptable salt thereof. Other embodiments provided herein relate to a method of treating a disease or condition that can include contacting a cell in the central and/or peripheral nervous system of a subject with an effective amount of a compound of Formulae (I) and/or (II), or a pharmaceutically acceptable salt thereof. In some embodiments, the subject can be at risk of developing a disease or condition that is responsive to acetaminophen and/or a NSAID. In some embodiments, the disease or condition can be one or more of the following: pain, fever, inflammation, ischemic injury (such as myocardial and/or cerebral) and/or neuronal injury. In some embodiments, the subject can be post-operative and has, or is believed to have or has actually developed post-operative pain. In some embodiments, a compound of Formulae (I) and/or (II), or a pharmaceutically acceptable salt thereof, can be provided (such as administered) prophylactically, for example, prophylactically for pain (such as post-operative pain).

In some embodiments, a compound of Formulae (I) and/or (II), or a pharmaceutically acceptable salt thereof, can contact a cell in the central nervous system, for example, the brain and/or spinal cord. In some embodiments, a compound of Formulae (I) and/or (II), or a pharmaceutically acceptable salt thereof, can contact a cell in the peripheral nervous system, for example, the ganglia and/or nervous system outside the brain and spinal cord.

In some embodiments, a compound of Formulae (I) and/or (II), or a pharmaceutically acceptable salt thereof, can contact a TRP (transient receptor potential) channels modulator (such as TRPV1 and/or TRPA1), and thereby treat a disease or condition described herein. In some embodiments, a compound of Formulae (I) and/or (II), or a pharmaceutically acceptable salt thereof, can contact a cannabinoid receptors modulator (such as CB1 and/or CB2), and thereby treat a disease or condition described herein. In some embodiments, a compound of Formulae (I) and/or (II), or a pharmaceutically acceptable salt thereof, can contact a serotonin receptor (for example, 5HT1, 5HT2, 5HT3, 5HT4, 5HT5, 5HT6 and/or 5HT7) and modulate its activity, and thereby treat a disease or condition described herein. In some embodiments, a compound of Formulae (I) and/or (II), or a pharmaceutically acceptable salt thereof, can act as an anandamide reuptake inhibitor, and thereby treat a disease or condition described herein. In some embodiments, a compound of Formulae (I) and/or (II), or a pharmaceutically acceptable salt thereof, can be a substrate for the fatty acid amide hydrolase (FAAH), and thereby treat a disease or condition described herein.

Some embodiments generally related to a method of treating pain of any etiology, including acute and chronic pain, and any pain in which acetaminophen is prescribed. Examples of pain include post-surgical pain; post-operative pain (including dental pain); migraine; headache and trigeminal neuralgia; pain associated with burn, wound and/or kidney stone; pain associated with trauma (including traumatic head injury); neuropathic pain (e.g., central and peripheral pain); pain associated with musculo-skeletal disorders; strains; sprains; contusions; fractures; myalgia; nociceptive pain (for example, rheumatoid arthritis and osteoarthritis); cystitis; visceral pain (such as, pancreatitis, inflammatory bowel disease and internal organ pain); ankylosing spondylitis; sero-negative (non-rheumatoid) arthropathies; non-articular rheumatism and peri-articular disorders; and mixed pain. Central pain includes post-stroke pain, pain associated with multiple sclerosis, spinal cord injury, migraine and HIV-related neuropathic pain. Peripheral pain includes post-herpetic neuralgia and diabetic neuropathy. Mixed pain includes pain associated with cancer (including "break-through pain" and pain associated with terminal cancer), lower back and fibromyalgia. Examples of pain with an inflammatory component (in addition to some of those described above) include rheumatic pain, pain associated with mucositis and pain associated with dysmenorrhea. In some embodiments, a method and/or a composition described herein can be used for treating or preventing post-surgical pain. In some embodiments, a method and/or a composition described herein can be used for treating or preventing of cancer pain. In some embodiments, a method and/or a composition described herein can be used for treating or preventing of osteoarthritis and/or rheumatoid arthritis pain. In some embodiments, a method and/or a composition described herein can be used for treating or preventing of migraine pain. In some embodiments, a method and/or a composition described herein can be used for treating or preventing of lower back pain and/or fibromyalgia pain. In some embodiments, a method and/or a composition described herein can be used for treating or preventing pain that is selected from pain associated with surgery, trauma, osteoarthritis, rheumatoid arthritis, lower back pain, fibromyalgia, postherpetic neuralgia, diabetic neuropathy, HIV-associated neuropathy and complex regional pain syndrome. Additionally information regarding pain is provided in Melnikova, I., "Pain market" (2010) 9 (8):589-590, which is hereby incorporated by reference in its entirety.

In some embodiments, a compound of Formulae (I) and/or (II), or a pharmaceutically acceptable salt thereof, can be used for treating or preventing pain and/or a fever (e.g., in adults, children and/or infants). Compounds of Formulae (I) and/or (II), or pharmaceutically acceptable salts thereof, can be used to treat a variety and varying degrees of pain. In some embodiments, the pain can be acute pain (e.g., acute pain following surgery, such as orthopedic surgery of adults, children, and/or infants).

In some embodiments, a compound of Formulae (I) and/or (II), or a pharmaceutically acceptable salt thereof, can be used for treating and/or preventing a fever, such as endotoxin-induced fever (e.g., endotoxin-induced fever in adults, children, and/or infants). In some embodiments, the fever can be selected from low-grade fever, moderate fever, high-grade fever and hyperpyrexia fever. In some embodiments, the fever can be selected from Pel-Ebstein fever, continuous fever, intermittent fever and remittent fever.

As described herein, compounds of Formulae (I) and/or (II), or pharmaceutically acceptable salts thereof, can be used in a various subjects. In some embodiments, the subject can be a child and/or an infant, for example, a child or infant with a fever. In other embodiments, the subject can be an adult.

Some embodiments described herein relate to a method of delaying the onset of analgesia in a subject in need thereof, wherein the method can include administering to the subject an effective amount of Formulae (I) and/or (II) that delays drug action by greater than about 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours, or 24 hours. Other embodiments described herein relate to a method of delaying the onset of analgesia in a subject in need thereof, wherein the method can include contacting a cell in the central and/or peripheral nervous system of a subject with an effective amount of Formulae (I) and/or (II) that delays drug action by greater than about 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours, or 24 hours.

As described herein, compounds of Formulae (I) and/or (II), or a pharmaceutically acceptable salt thereof, can be administered by a variety of methods. In any of the methods described herein, administration can be by injection, infusion and/or intravenous administration over the course of 1 minute, 5 minutes, 10 minutes, 30 minutes, 1 hour, 2 hours, 6 hours, 12 hours, 24 hours or longer, or any intermediate time. Such administration can, in some circumstances, substitute for or significantly reduce the need for administration of an opiate. Some methods described herein can include intravenous administration to a subject in need thereof, for example, to a subject to manage post-operative or other acute or chronic pain, in either a bolus dose or by infusion over minutes, hours, or days. Other methods described herein can include oral, intravenous and/or intraperitoneal administration to a subject in need thereof, for example, to a subject to manage post-operative or other acute or chronic pain.

Other embodiments described herein relate to a method for selecting a therapy for managing or treating pain in a subject in need thereof, that can include evaluating whether the subject is at risk for hepatic toxicity from pain therapy, and selecting therapy that includes a compound of Formulae (I) and/or (II), or a pharmaceutically acceptable salt thereof, to reduce or eliminate such risk. The method can further include providing the selected therapy that includes a compound of Formulae (I) and/or (II), or a pharmaceutically acceptable salt thereof, to the subject. In some embodiments, a compound of Formulae (I) and/or (II), or a pharmaceutically acceptable salt thereof, can be of significant benefit in pain management in hospitals or other care facilities (for example, a nursing home).

As used herein, the terms "prevent" and "preventing," mean a subject does not experience and/or develop pain and/or fever, or the severity of the pain and/or fever is less compared to the severity of the pain and/or fever if the subject has not been administered/received the compound. Examples of forms of prevention include prophylactic administration to a subject who is going to undergo surgery.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or conditions.

In general, however, a suitable dose will often be in the range of from about 0.15 mg/kg to about 100 mg/kg. For example, a suitable dose may be in the range from about 1 mg/kg to about 75 mg/kg of body weight per day, such as about 0.75 mg/kg to about 50 mg/kg of body weight of the recipient per day, about 1 mg/kg to 90 mg/kg of body weight of the recipient per day, or about 10 mg/kg to about 60 mg/kg of body weight of the recipient per day.

The compound may be administered in unit dosage form; for example, containing 1 to 2000 mg, 10 to 1000 mg or 5 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of compounds of Formulae (I) and/or (II), or pharmaceutically acceptable salts thereof, can be determined by comparing their in vitro activity, and in vivo activity in animal models. Such comparison can be done against an established analgesic drug, such as acetaminophen.

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Drugs

One or more compounds of Formulae (I) and/or (II), or a pharmaceutically acceptable salt thereof, can be provided alone or in combination with another drug(s). In some embodiments, the other drug(s) can be an opioid analgesic. Any of the known opioid analgesics can be combined with a compound of Formulae (I) and/or (II), or a pharmaceutically acceptable salt thereof. As non-limiting examples, such opioid analgesics include morphine, codeine, hydrocodone, oxycodone, fentanyl, pethidine, methadone, pentazocine, sufentanil, levorphanol, dihydrocodeine, nalbuphine, butorphanol, tramadol, meptazinol, buprenorphine, dipipanone, alfentanil, remifentanil, oxymorphone, tapentadol, propoxyphene and hydromorphone.

In some embodiments, a compound of Formulae (I) and/or (II), or a pharmaceutically acceptable salt thereof, can be provided in a dosage form (for example, an oral dosage form, an intravenous dosage form and/or an intraperitoneal dosage form), in combination with one of the following exemplary opioids: 1-20 mg hydrocodone (such as hydrocodone bitartrate), preferably 2.5 mg, 5 mg, 7.5 mg or 10 mg of hydrocodone or salt thereof; or 1-20 mg oxycodone, preferably 2.5 mg, 5 mg, 7.5 mg or 10 mg of hydrocodone or salt thereof (such as the hydrochloride salt). In some embodiments, the amount of a compound of Formulae (I) and/or (II), or a pharmaceutically acceptable salt thereof, can be in the range of about 20 to about 2000 mg.

Other combinations include combination of a compound of Formulae (I) and/or (II), or a pharmaceutically acceptable salt thereof, with butalbital, codeine, dihydrocodeine, ibuprofen, aspirin and/or naproxen. The other drug(s) can be provided using routes known to those skilled in the art and/or described herein. In some embodiments, a compound of Formulae (I) and/or (II), or a pharmaceutically acceptable salt thereof, and another drug(s) can be provided in the same dosage form. In other embodiments, a compound of Formulae (I) and/or (II), or a pharmaceutically acceptable salt thereof, and another drug(s) can be provided in the separate dosage forms. In some embodiments, a compound of Formulae (I) and/or (II), or a pharmaceutically acceptable salt thereof, and another drug(s) can be by the same route (for example, both intravenously) or by different routes (for example, one orally and the other intraperitoneally). In some embodiments, a compound of Formulae (I) and/or (II), or a pharmaceutically acceptable salt thereof, can be provided before another drug(s) (such as an opiate). In other embodiments, a compound of Formulae (I) and/or (II), or a pharmaceutically acceptable salt thereof, can be provided simultaneously with another drug(s) (such as an opiate). In still other embodiments, a compound of Formulae (I) and/or (II), or a pharmaceutically acceptable salt thereof, can be provided after another drug(s) (such as an opiate).

In some embodiments, a combination of a compound of Formulae (I) and/or (II), or a pharmaceutically acceptable salt thereof, and an opioid analgesic can synergistically relieve pain. In some embodiments, the synergistic relief of pain can reduce opioid use. Some embodiments disclosed herein relate to a method of managing, treating and/or reducing pain that can include administering an effective amount of a combination of a compound of Formulae (I) and/or (II), or a pharmaceutically acceptable salt thereof, and an opioid analgesic to a subject. Some embodiments disclosed herein relate to a method for reducing opioid use in pain management, that can include administering an amount of a compound of Formulae (I) and/or (II), or a pharmaceutically acceptable salt thereof, in combination with an amount of an opioid analgesic, wherein the amount of the opioid analgesic in the combination is less than the amount of opioid analgesic needed to achieve approximately the same level of pain management when the opioid analgesic is administered alone. Methods known for evaluating pain management is known to those skilled in the art, for example, pain assessment tools. Some embodiments disclosed herein relate to a method for decreasing the risk of opioid dependency that can include administering an amount of a compound of Formulae (I) and/or (II), or a pharmaceutically acceptable salt thereof, in combination with an amount of an opioid analgesic, wherein the amount of the opioid analgesic in the combination is less than the amount of opioid analgesic needed to achieve approximately the same level of pain management when the opioid analgesic is administered alone. Some embodiments disclosed herein relate to a method for treating pain and/or fever along with treating opioid dependency that can include administering an amount of a compound of Formulae (I) and/or (II), or a pharmaceutically acceptable salt thereof, in combination with an amount of an opioid analgesic.

EXAMPLES

Additional embodiments are disclosed in further detail in the following examples, which are not in any way intended to limit the scope of the claims.

Example 1

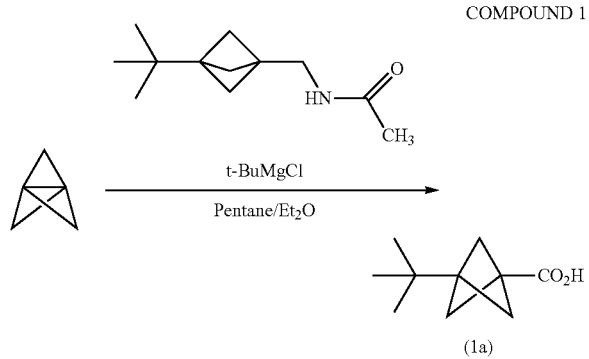

COMPOUND 1

To a solution of propellane (0.311 M in Et$_2$O/pentane, 0.400 g, 6.05 mmol, 19.5 mL) cooled to −50° C. was added dropwise tert-butylmagnesium chloride (2.0 M in Et$_2$O, 0.710 g, 6.05 mmol, 3.03 mL). The solution was allowed to warm to room temperature (rt) and stirred for 4 d. After 4 d, the solution was cooled to 0° C. and CO$_2$ was rapidly bubbled through the solution for 10 mins. The solution was allowed to warm to rt and then the mixture was washed with H$_2$O (3×20 mL). The combined aqueous layers were acidified with HCl (acidic by pH paper). Brine (15 mL) was added, and the mixture was extracted with EtOAc (4×20 mL). The combined organics were dried (Na$_2$SO$_4$) and concentrated under reduced pressure to afford 1a (0.748 g, 74%) as a white solid. $^1$H NMR (400 MHz, DMSO-d$_6$) δ 12.22 (s, COOH, 1H), 1.72 (s, 6H), 0.81 (s, 9H).

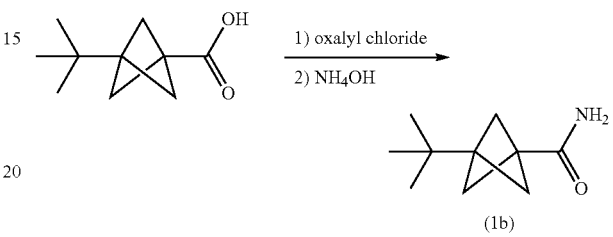

To a solution of 1a (0.8 g, 4.76 mmol) in 1,2-DCE (25 mL) and DMF (0.08 mL) was added oxalyl chloride (0.9 mL, 10.5 mmol) dropwise. A gas evolution was observed, and the reaction became a clear light yellow solution. Gas evolution subsided after 10 mins, and the reaction was stirred at rt. After 3 h, the reaction was cooled to 0° C. and an ammonium hydroxide solution (28% NH$_3$ in H$_2$O, 16.0 mL, 237.8 mmol) was added rapidly to the solution via syringe. The reaction was stirred overnight at rt. After 16 h, the reaction was filtered, and the collected solid was washed with DCM. The aqueous layer was washed DCM (2×). The combined organic layers were dried over Na$_2$SO$_4$, filtered and concentrated in vacuo to provide 1b (0.772 g, 91%) as a light yellow solid. $^1$H-NMR (400 MHz, CDCl$_3$) δ 1.83 (s, 3H), 0.85 (s, 6H); LC/MS (APCI) m/z 168.1 [C$_9$H$_{17}$NO+H]$^+$.

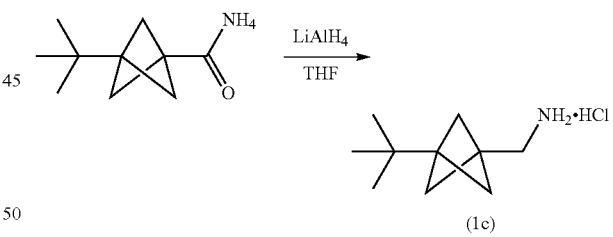

A solution of 1b (0.772 g, 4.62 mmol) in THF (23 mL) was cooled to 0° C. and treated with LiAlH$_4$ (2M in THF, 5.1 mL, 10.2 mmol) dropwise. Gas evolution was observed over the 5 mins. Following the addition, the reaction was warmed to rt. After 17 h, the reaction was cooled to 0° C. and treated with H$_2$O (386 μL), followed by 15% w/v aqueous NaOH solution (386 μL) and H$_2$O (1.2 mL). The reaction was stirred for 45 mins at rt. The reaction was filtered, and the collected aluminum salts were washed with EtOAc. The combined filtrates were treated with Na$_2$SO$_4$ and were subsequently filtered. The filtrate was cooled to 0° C. and HCl (4M in dioxane, 5.8 mL, 23.1 mmol) was added dropwise. The reaction was stirred at rt for 30 min and then concentrated in vacuo to provide a white solid. The white solid was triturated with Et$_2$O to provide 1c (655 mg, 75%)

as a white solid. $^1$H-NMR (400 MHz, CD$_3$OD) δ 3.01 (s, 2H), 1.62 (s, 6H), 0.88 (s, 9H); LC/MS (APCI) m/z 154.1 [C$_{10}$H$_{19}$N+H]$^+$.

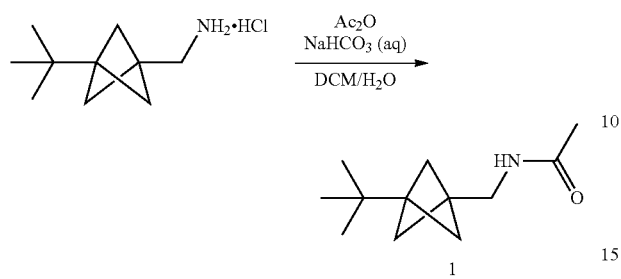

A solution of 1c (0.140 g, 0.74 mmol) in DCM (3.7 mL) and sat. aq. NaHCO3 (11.1 mL) at 0° C. was treated with acetic anhydride (0.350 mL, 3.7 mmol). The mixture was stirred at 0° C. After 2.5 h, the reaction was complete as indicated by LCMS. The mixture was extracted with DCM (3×15 mL). The combined organics were washed with H$_2$O (20 mL) and brine (20 mL), dried (MgSO4) and concentrated under reduced pressure to afford the crude product that was further purified by SiO$_2$ chromatography (0-60% EtOAc/Hexanes) to provide 1 (76.7 mg, 53%) as a white solid. $^1$H-NMR (400 MHz, DMSO-d$_6$) δ 7.70 (br s, 1H), 3.10 (d, J=5.6 Hz, 2H), 1.80 (s, 3H), 1.38 (s, 6H), 0.80 (s, 9H); LC/MS (APCI) m/z 196.1 [C$_{12}$H$_{21}$NO+H]$^+$.

Example 2

COMPOUND 2

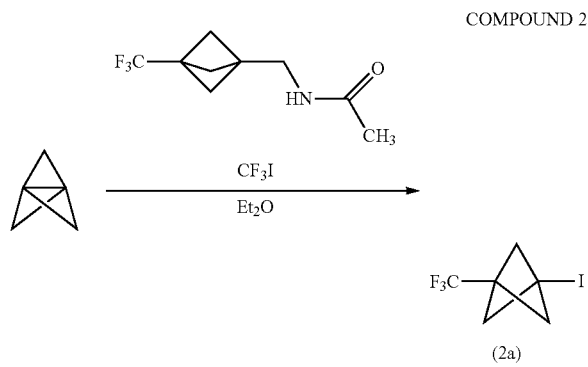

Trifluoromethyliodide (1.96 g, 9.98 mmol, 0.768 mL) was condensed into a pressure vessel at −78° C. A solution of propellane (0.211 M in Et$_2$O, 0.300 g, 4.54 mmol, 21.5 mL) at −78° C. was cannulated over, and the vessel was sealed and allowed to warm to rt. The solution was allowed to stand for 3 d at rt and protected from light. The volatiles were removed at 0° C. under reduced pressure to provide the crude product as an off-white solid. Hexanes (15 mL) were added, and the solution was cooled to −78° C. at which time the product precipitated out as a white solid. The solid was then washed with cold (−78° C.) hexanes (3×5 mL), and the product was dried under a slight vacuum to afford 2a (1.022 g. 86%) as a white solid. $^1$H NMR (400 MHz, CDCl$_3$) δ 2.47 (s, 6H).

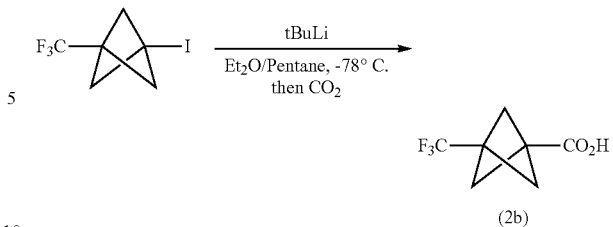

1-(Trifluoromethyl)-3-iodobicyclo[1.1.1]pentane (1.02 g, 3.89 mmol) was dissolved in anhydrous diethyl ether (13.0 mL) and cooled to −78° C. A solution of tBuLi (1.7 M in pentane, 0.549 g, 8.56 mmol, 5.04 mL) was added slowly, and the solution was stirred at −78° C. After 30 mins, CO$_2$ was bubbled through the solution for 10 mins, and the reaction was allowed to warm to rt. Diethyl ether (10 mL) was added, and the mixture was extracted with H$_2$O (3×20 mL). The combined aqueous layers were acidified with 2M HCl then extracted with Et$_2$O (3×20 mL). The combined organics were dried (MgSO4) and concentrated under reduced pressure to afford 2b (0.603 g, 86%) as a white solid which was carried forward without further purification. $^1$H NMR (400 MHz, DMSO-d$_6$) δ 12.77 (br s, COOH, 1H), 2.20 (s, 6H).

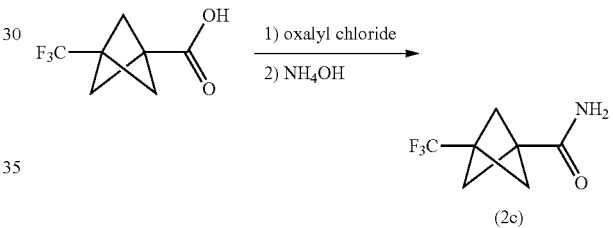

To a solution of 2b (0.9 g, 4.76 mmol) in 1,2-DCE (17 mL) and DMF (0.040 mL) was added oxalyl chloride (0.93 mL, 11.0 mmol) dropwise. Gas evolution was observed, and the reaction became a clear light yellow solution. Gas evolution subsided after 5 mins, and the reaction was stirred at rt. After 2 h, the reaction was cooled to 0° C. and an ammonium hydroxide solution (28% NH$_3$ in H$_2$O, 16.9 mL, 249.8 mmol) was added rapidly to the solution by syringe. The reaction was stirred overnight at rt. After 16 h, the reaction was filtered, and the collected solid was washed with water (40 mL) and 95:5 EtOAc:MeOH (200 mL). The aqueous layer was washed with 95:5 EtOAc:MeOH (2×). The combined organic layers were dried over Na$_2$SO$_4$, filtered and concentrated in vacuo to provide 2c (0.690 g, 77%) as a white solid. $^1$H-NMR (400 MHz, DMSO-d$_6$) δ 7.44 (s, 1H), 7.14 (s, 1H), 2.12 (s, 6H); LC/MS (APCI) m/z 180.0 [C$_7$H$_8$F$_3$NO+H]$^+$.

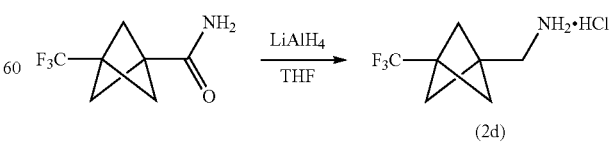

A solution of 2c (0.597 g, 3.34 mmol) in THF (24 mL) was cooled to 0° C. and treated with LiAlH$_4$ (2 M in THF, 4.2 mL, 16.7 mmol) dropwise. Gas evolution was observed over 5 mins. The reaction was warmed to rt. After 17 h, the reaction was cooled to 0° C. and treated with H$_2$O (300 μL), followed by 15% w/v aqueous NaOH solution (300 μL) and H$_2$O (900 mL). The reaction was stirred for 45 mins at rt. The mixture was filtered, and the collected aluminum salts were washed with EtOAc. The combined filtrates were treated with Na$_2$SO$_4$ and were subsequently filtered. The filtrate was cooled to 0° C. and HCl (4M in dioxane, 4.2 mL, 16.7 mmol) was added dropwise. The reaction was stirred at rt for 30 mins and then concentrated in vacuo to provide a white solid. The white solid was triturated with Et$_2$O to provide 2d (528.5 mg, 79%) as a white solid. $^1$H-NMR (400 MHz, CD$_3$OD) δ 3.13 (s, 2H), 2.06 (s, 6H); LC/MS (APCI) m/z 166.1 [C$_7$H$_{10}$F$_3$N+H]$^+$.

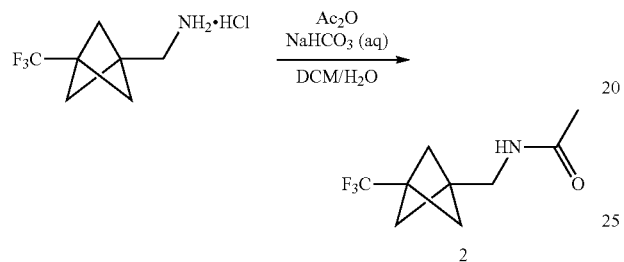

2

A solution of 2d (0.327 g, 1.62 mmol) in DCM (8.11 mL) and sat. aq. NaHCO$_3$ (16.2 mL) at 0° C. was treated with acetic anhydride (0.828 g, 8.11 mmol, 0.767 mL) and stirred at 0° C. After completion by LCMS (~4 h), the solution was extracted with DCM (4×30 mL). The combined organics were washed with sat. NaHCO$_3$ (20 mL), brine (20 mL), dried (Na$_2$SO$_4$) and concentrated under reduced pressure to afford the crude product as an off-white solid that was further purified by flash chromatography (SiO$_2$, Hexanes/EtOAc) to afford 2 (0.304 g, 91%) as a white solid. $^1$H NMR (400 MHz, CDCl$_3$) δ 5.47 (br s, NH, 1H), 3.39 (d, J=6.06 Hz, 2H), 2.00 (s, 3H), 1.89 (s, 6H); LC/MS (APCI) m/z 208.10 [C$_9$H$_{12}$F$_3$NO+H]$^+$.

Example 3

COMPOUND 3

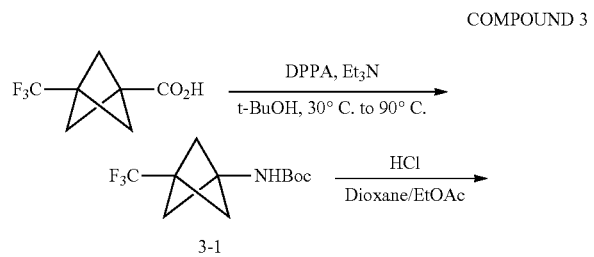

A solution of 3-(trifluoromethyl)bicyclo[1.1.1]pentane-1-carboxylic acid (0.580 g, 3.22 mmol) in anhydrous tert-BuOH (16.1 mL) was treated with Et$_3$N (0.652 g, 6.44 mmol, 0.898 mL) and diphenylphosphoryl azide (1.06 g, 3.86 mmol, 0.833 mL). The resulting solution was stirred at 30° C. under N$_2$ for 4 h, and then warmed to 90° C. and stirred overnight. The solution was concentrated under reduced pressure, diluted with H$_2$O (30 mL) and extracted with EtOAc (3×20 mL). The combined organics were dried (MgSO4) and concentrated to afford the crude product that was further purified by flash chromatography (SiO$_2$, Hexanes/EtOAc) to provide 3-1 (0.703 g, 87%) as a white solid. $^1$H NMR (400 MHz, CDCl$_3$) δ 4.95 (br s, NH, 1H), 2.22 (s, 6H), 1.45 (s, 9H); LC/MS (APCI) m/z 152.1 [C$_{11}$H$_{16}$F$_3$NO$_2$—C$_5$H$_9$O$_2$+H]$^+$.

A solution of 3-1 (0.703 g, 2.80 mmol) in EtOAc (7.0 mL) was treated with HCl (4.0 M in dioxane, 28.0 mmol, 7.0 mL), and the mixture was stirred at rt overnight. After stirring overnight, white precipitate formed. The mixture was concentrated under reduced pressure. The resulting white solid was triturated with diethyl ether and filtered to afford 3 (0.421 g, 80%) as a white solid. $^1$H NMR (400 MHz, DMSO-d$_6$) δ 9.19 (br s, NH, 3H), 2.26 (s, 6H); LC/MS (APCI) m/z 152.1 [C$_6$H$_8$F$_3$N+H]$^+$.

Example 4

COMPOUND 4

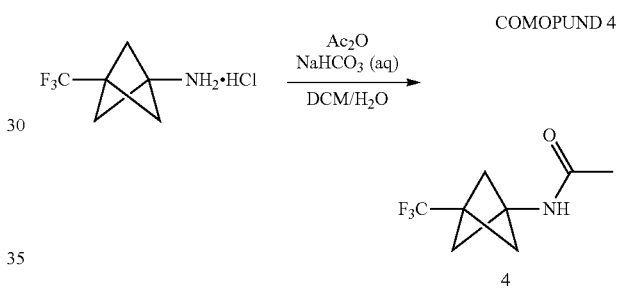

4

A solution of 3 (1.00 g, 5.33 mmol) in DCM (26.7 mL) and sat. aq. NaHCO$_3$ (53.3 mL) at 0° C. was treated with acetic anhydride (2.72 g, 26.7 mmol, 2.52 mL), and the mixture was stirred at 0° C. After completion (determined by LCMS, ~3 h), the solution was extracted with DCM (4×20 mL). The combined organics were dried (Na$_2$SO$_4$) and concentrated under reduced pressure to afford the crude product as an off-white solid. Purification by flash chromatography (SiO$_2$, Hexanes/EtOAc) to afford 4 (0.868 g, 84%) as a white solid. $^1$H NMR (400 MHz, CDCl$_3$) δ 5.88 (br s, NH, 1H), 2.29 (s, 6H), 1.95 (s, 3H); LC/MS (APCI) m/z 194.1 [C$_8$H$_{10}$F$_3$NO+H]$^+$.

Example 5

COMPOUND 5

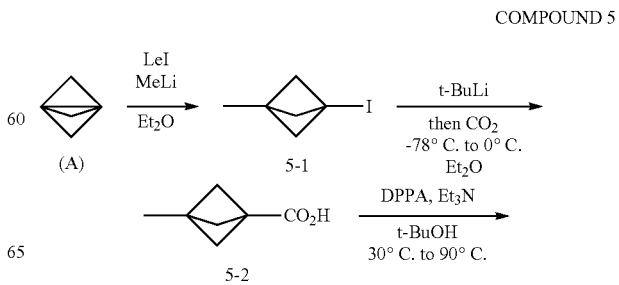

-continued

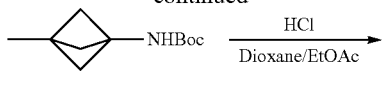
5-3

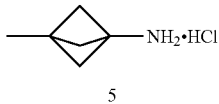
5

Example 6

COMPOUND 6

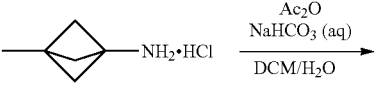

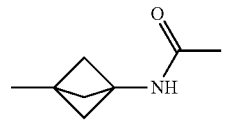
6

A solution of methyllithium (5.30 mL, 8.48 mmol) was added dropwise to a 0.311M solution of tricyclo[1.1.1.0¹,3]pentane (28.7 mL, 8.93 mmol) in Et$_2$O and methyl iodide (0.530 mL, 8.48 mmol) at −40° C. Once the addition was complete, the solution was allowed to warm to rt and stir for 24 h. The mixture was then cooled to −40° C., and MeOH (10 mL) was added. The resulting solution was poured into an ice-cold mixture of H$_2$O (50 mL) and pentane (50 mL). After separation of the layers, the organic phase was washed with H$_2$O (2×50 mL), dried (Na$_2$SO$_4$) and concentrated to a volume of ~2 mL under reduced pressure at 0° C. The final concentration was determined by ¹H NMR and 5-1 (0.942 g, 51%) was obtained as a colorless solution in Et$_2$O. ¹H NMR (400 MHz, CDCl$_3$) δ 2.21 (s, 6H), 1.21 (s, 3H).

5-1 (0.940 g, 4.52 mmol) was dissolved in anhydrous Et$_2$O (15.1 mL) and cooled to −78° C. A solution of tert-butyllithium (1.7M in pentane, 0.637 g, 9.94 mmol, 5.85 mL) was added dropwise, and the solution was stirred at −78° C. for 1 h. After 1 h, CO$_2$ was bubbled through the solution for 10 mins, and the reaction was allowed to warm to rt. Diethyl ether (10 mL) was added, and the mixture was extracted with H$_2$O (3×20 mL). The combined aqueous layers were acidified with 1M HCl, and then extracted with Et$_2$O (3×20 mL). The combined organics were dried (MgSO4) and concentrated under reduced pressure to afford 5-2 (0.501 g, 88%) as a white solid, which was carried forward without further purification. ¹H NMR (400 MHz, DMSO-d$_6$) δ 12.11 (br s, COOH, 1H), 1.82 (s, 6H), 1.14 (s, 3H).

5-2 (0.500 g, 3.96 mmol) was dissolved in tert-BuOH (19.8 mL). Et$_3$N (0.802 g, 7.93 mmol, 1.11 mL) and activated 3 Å molecular sieves were added followed by diphenylphosphoryl azide (1.025 mL, 4.76 mmol). The resulting solution was stirred at 30° C. for 4 h, and then heated to reflux overnight. The solution was cooled to rt and then concentrated under reduced pressure. The residual oil was diluted with EtOAc (20 mL) and H$_2$O (20 mL), and extracted with EtOAc (4×20 mL). The combined organics were dried (Na$_2$SO$_4$) and concentrated to afford the crude product that was further purified by flash chromatography (SiO$_2$, Hexanes/EtOAc) to provide 5-3 (0.513 g, 66%) as a semi-pure white solid. ¹H NMR (400 MHz, CDCl$_3$) δ 4.87 (br s, NH, 1H), 1.85 (s, 6H), 1.43 (s, 9H), 1.21 (s, 3H); LC/MS (APCI) m/z 98.1 [C$_{11}$H$_{19}$NO$_2$—C$_5$H$_9$O$_2$+H]$^+$.

To a solution of 5-3 (0.513 g, 2.60 mmol) in EtOAc (6.50 mL) was added HCl (4 M in dioxane, 6.50 mL, 26.0 mmol). The resulting solution was stirred at rt overnight. After stirring overnight, the mixture became cloudy with partial precipitation of the product. The suspension was concentrated, and the residual solid was triturated with Et$_2$O (2×10 mL). The precipitate was collected by filtration, and the filter cake was washed with Et$_2$O (20 mL). The white solid was dried under vacuum to afford 5 (0.219 g, 63%) as a white powder. ¹H NMR (400 MHz, DMSO-d$_6$) δ 8.69 (br s, NH, 3H), 1.84 (s, 6H), 1.22 (s, 3H); LC/MS (APCI) m/z 98.1 [C$_6$H$_{11}$N+H]$^+$.

A solution of 5 (0.150 g, 1.12 mmol) in DCM (5.6 mL) and sat. aq. NaHCO$_3$ (11.2 mL) at 0° C. was treated with acetic anhydride (0.573 g, 5.61 mmol, 0.531 mL), and the mixture was stirred at 0° C. After 2 h, the solution was extracted with DCM (4×10 mL), and the combined organics were washed with sat. aq. NaHCO$_3$ (10 mL) and brine (10 mL), dried (MgSO4) and concentrated under reduced pressure to afford the crude product that was further purified by flash chromatography (SiO$_2$, Hexanes/EtOAc) to afford 6 (0.127 g, 81%) as a white solid. ¹H NMR (400 MHz, CDCl$_3$) δ 5.78 (br s, NH, 1H), 1.93 (s, 6H), 1.91 (s, 3H), 1.21 (s, 3H); LC/MS (APCI) m/z 140.1 [C$_8$H$_{13}$NO+H]$^+$.

Example 7

COMPOUND 7

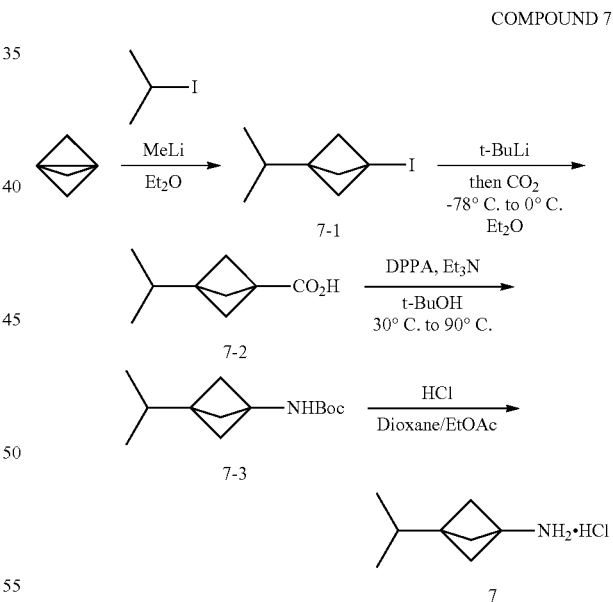

A solution of MeLi (1.6 M, 10.1 mmol, 6.29 mL) was added dropwise to a solution of isopropyliodide (1.71 g, 10.1 mmol, 1.00 mL) and propellane (0.311 M in Et$_2$O, 0.700 g, 10.6 mmol, 34.1 mL) cooled to −40° C. The mixture was allowed to warm to rt and stirred for 24 h. The mixture was then cooled to −40° C. and MeOH (20 mL) was added. The resulting solution was poured into an ice-cold mixture of H$_2$O (50 mL) and pentane (50 mL). After separation of the layers, the organic phase was washed with H$_2$O (2×50 mL), dried (Na$_2$SO$_4$) and concentrated under reduced pressure at 0° C. to afford 7-1 (2.67 g, >99%) as a semi-pure colorless oil that was used without further purification. $^1$H NMR (400 MHz, CDCl$_3$) δ 2.15 (s, 6H), 1.78 (sep, J=6.8 Hz, 1H), 0.82 (d, J=6.8 Hz, 6H).

7-1 (2.50 g, 10.6 mmol) was dissolved in anhydrous Et$_2$O (35.3 mL) and cooled to −78° C. A solution of tert-BuLi (1.7M in pentane, 1.49 g, 23.3 mmol, 13.7 mL) was added dropwise, and the solution was stirred at −78° C. for 1 h. After 1 h, CO$_2$ was bubbled through the solution for 10 mins, and the reaction was allowed to warm to rt. Et$_2$O (10 mL) was added, and the mixture was extracted with H$_2$O (3×20 mL). The combined aqueous layers were acidified with 1M HCl and then extracted with DCM (3×30 mL). The combined organics were dried (MgSO4) and concentrated under reduced pressure to afford 7-2 (1.42 g, 87%) as an oily solid which was carried forward without further purification. $^1$H NMR (400 MHz, DMSO-d$_6$) δ 12.18 (br s, COOH, 1H), 1.73 (s, 6H), 1.64 (sep, J=6.8 Hz, 1H), 0.79 (d, J=6.8 Hz, 6H).

A solution of 7-2 (1.42 g, 9.21 mmol) in anhydr. tert-BuOH (46.0 mL) was treated with Et$_3$N (1.86 g, 18.4 mmol, 2.57 mL) and diphenylphosphoryl azide (3.04 g, 11.1 mmol, 2.38 mL). The resulting solution was stirred at 30° C. under N$_2$. After 4 h, the solution was warmed to 90° C. and stirred overnight. The solution was concentrated under reduced pressure and then diluted with H$_2$O (30 mL). The solution was extracted with EtOAc (3×20 mL). The combined organics were dried (MgSO4) and concentrated to afford the crude product that was further purified by flash chromatography (SiO$_2$, Hexanes/EtOAc) to provide 7-3 (1.42 g, 69%) as a white solid. $^1$H NMR (400 MHz, CDCl$_3$) δ 4.90 (br s, NH, 1H), 1.77 (s, 6H), 1.75 (sep, J=6.8 Hz, 1H), 1.44 (s, 9H), 0.82 (d, J=6.8 Hz, 6H).

A solution of 7-3 (1.42 g, 6.30 mmol) in EtOAc (15.8 mL) was treated with HCl (4.0M in dioxane, 63.0 mmol, 15.8 mL), and the mixture was stirred at rt overnight. The solution was concentrated under reduced pressure to afford the crude compound as an off-white solid. The solid was triturated with Et$_2$O (3×5 mL) to afford 7 (0.858 g, 84%) as a white powder. $^1$H NMR (400 MHz, DMSO-d$_6$) δ 8.78 (br s, NH, 3H), 1.77 (sep, J=6.8 Hz, 1H), 1.75 (s, 6H), 0.81 (d, J=6.8 Hz, 6H); LC/MS (APCI) m/z 126.1 [C$_8$H$_{15}$N+H]$^+$.

Example 8

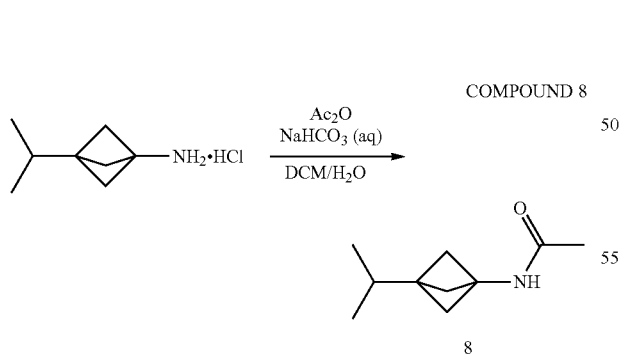

COMPOUND 8

A solution of 7 (0.300 g, 1.86 mmol) in DCM (9.3 mL) and sat. aq. NaHCO$_3$ (18.6 mL) at 0° C. was treated with acetic anhydride (0.947 g, 9.28 mmol, 0.877 mL), and the mixture was stirred at 0° C. After 2 h, the solution was extracted with DCM (4×20 mL). The combined organics were washed with sat. aq. NaHCO$_3$ (20 mL) and brine (20 mL), dried (Na$_2$SO$_4$) and concentrated under reduced pressure to afford the crude product as an off-white solid that was further purified by flash chromatography (SiO$_2$, Hexanes/EtOAc) to afford 8 (0.289 g, 93%) as a white solid. $^1$H NMR (400 MHz, CDCl$_3$) δ 5.80 (br s, NH, 1H), 1.92 (s, 3H), 1.85 (s, 6H), 1.76 (sep, J=6.8 Hz, 1H), 0.83 (d, J=6.8 Hz, 6H); LC/MS (APCI) m/z 168.1 [C$_{10}$H$_{17}$NO+H]$^+$.

Example 9

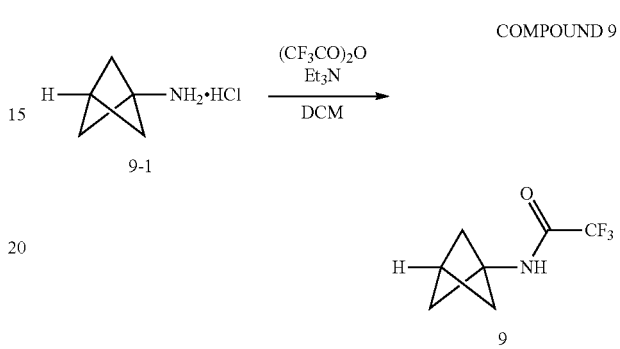

COMPOUND 9

A solution of 9-1 (0.300 g, 2.51 mmol) in DCM (8.36 mL) at 0° C. was treated with Et$_3$N (0.635 g, 6.27 mmol, 0.874 mL) and trifluoroacetic anhydride (0.632 g, 3.01 mmol, 0.425 mL). The mixture was allowed to warm to rt and stir overnight. The mixture was extracted with DCM (4×5 mL). The combined organic layers were washed with 1M HCl (5 mL), H$_2$O (5 mL), sat. NaHCO$_3$ (5 mL) and then brine (5 mL). The combined organic layers were dried (Na$_2$SO$_4$) and concentrated under reduced pressure to provide the crude product that was further purified by flash chromatography (SiO$_2$, Hexanes/EtOAc) to afford 9 (0.232 g, 52%) as a white solid. $^1$H NMR (400 MHz, CDCl$_3$) δ 6.60 (br s, NH, 1H), 2.54 (s, 1H), 2.17 (s, 6H); LC/MS (APCI) m/z 180.1 [C$_7$H$_8$F$_3$NO+H]$^+$.

Example 10

COMPOUND 10

A solution of 10-1 (0.300 g, 1.71 mmol) in DCM (5.69 mL) at 0° C. was treated with Et$_3$N (0.432 g, 4.27 mmol, 0.595 mL) and trifluoroacetic anhydride (0.430 g, 2.05 mmol, 0.289 mL). The mixture was allowed to warm to rt. After 3 h, the mixture was extracted with DCM (4×5 mL). The combined organic layers were washed with 1M HCl (5 mL), H$_2$O (5 mL), sat. NaHCO$_3$ (5 mL) and then brine (5 mL). The combined organic layers were dried (Na$_2$SO$_4$) and concentrated under reduced pressure to provide the crude product that was further purified by flash chromatography (SiO$_2$, Hexanes/EtOAc) to afford 10 (0.375 g, 93%) as a white solid. $^1$H NMR (400 MHz, CDCl$_3$) δ 6.55 (br s, NH, 1H), 1.94 (s, 6H), 0.88 (s, 9H); LC/MS (APCI) m/z 234.1 [C$_{11}$H$_{16}$F$_3$NO—H]$^+$.

Example 11

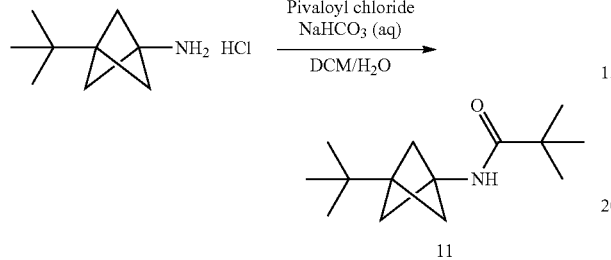

COMPOUND 11

A solution of 10-1 (0.200 g, 1.14 mmol) in DCM (5.69 mL) and sat. aq. NaHCO$_3$ (11.4 mL) at 0° C. was treated with pivaloyl chloride (0.690 g, 5.69 mmol, 0.635 mL). The mixture was stirred at rt for 2 h. The mixture was then extracted with DCM (4×5 mL). The combined organic layers were washed with 1M HCl (5 mL), H$_2$O (5 mL), sat. NaHCO$_3$ (5 mL) and then brine (5 mL). The combined organic layers were dried (Na$_2$SO$_4$) and concentrated under reduced pressure to provide the crude product that was further purified by flash chromatography (SiO$_2$, Hexanes/EtOAc) to afford 11 (0.224 g, 88%) as a white solid. $^1$H NMR (400 MHz, CDCl$_3$) δ 5.91 (br s, NH, 1H), 1.85 (s, 6H), 1.17 (s, 9H), 0.86 (s, 9H); LC/MS (APCI) m/z 224.2 [C$_{14}$H$_{25}$NO+H]$^+$.

Example 12

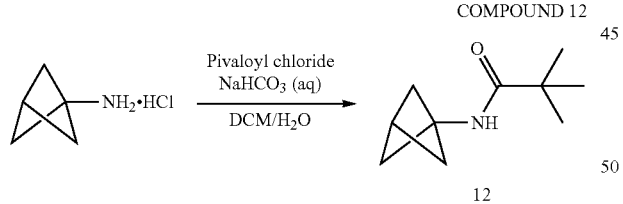

COMPOUND 12

A solution of 9-1 (0.300 g, 2.51 mmol) in DCM (12.5 mL) and sat. aq. NaHCO$_3$ (25.1 mL) at 0° C. was treated with pivaloyl chloride (1.51 g, 12.5 mmol, 1.4 mL), and the mixture was stirred at rt. After 2 h, the mixture was extracted with DCM (4×10 mL). The combined organic layers were washed with 1M HCl (10 mL), H$_2$O (10 mL), sat. NaHCO$_3$ (10 mL) and then brine (10 mL). The combined organic layers were dried (Na$_2$SO$_4$) and concentrated under reduced pressure to provide the crude product that was further purified by flash chromatography (SiO$_2$, Hexanes/EtOAc) to afford 12 (0.220 g, 52%) as a white solid. $^1$H NMR (400 MHz, CDCl$_3$) δ 5.95 (br s, NH, 1H), 2.44 (s, 1H), 2.08 (s, 6H), 1.17 (s, 9H); LC/MS (APCI) m/z 168.1 [C$_{10}$H$_{17}$NO+H]$^+$.

Example 13

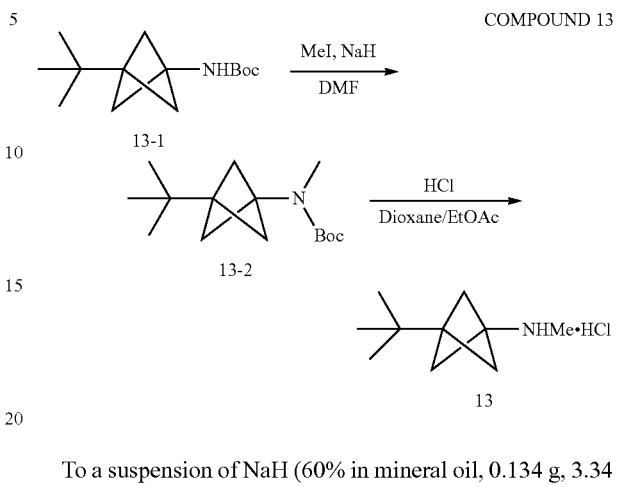

COMPOUND 13

To a suspension of NaH (60% in mineral oil, 0.134 g, 3.34 mmol) in anhydrous DMF (0.62 mL) at 0° C. was added a solution of 13-1 (0.400 g, 1.67 mmol) in DMF (3.34 mL). The mixture was stirred for 5 mins followed by the addition of MeI (0.710 g, 5.01 mmol, 0.312 mL). The resulting solution was allowed to warm to rt. After 2 h, the reaction was quenched by the addition of water (1 mL). The mixture was diluted with EtOAc (20 mL) and H$_2$O (50 mL), and extracted with EtOAc (3×20 mL). The combined organics were dried (Na$_2$SO$_4$) and concentrated under reduced pressure to afford an oil that was further purified by flash chromatography (SiO$_2$, 0-50% EtOAc/Hexanes) to afford 13-2 (0.394 g, 93%) as a colorless oil. $^1$H NMR (400 MHz, CDCl$_3$) δ 2.78 (s, 3H), 1.80 (s, 6H), 1.46 (s, 9H), 0.86 (s, 9H); LC/MS (APCI) m/z 154.2 [C$_{15}$H$_{27}$NO$_2$—C$_5$H$_9$O$_2$+H]$^+$.

A solution of 13-2 (0.394 g, 1.55 mmol) in EtOAc (3.88 mL) was treated with HCl (4.0M in dioxane, 15.5 mmol, 3.9 mL), and the mixture was stirred at rt overnight. The solution was concentrated under reduced pressure to afford the crude compound as a white solid. The solid was filtered and washed with Et$_2$O (3×10 mL) to afford 13 (0.294 g, >99%) as a white solid. $^1$H NMR (400 MHz, DMSO-d$_6$) δ 9.43 (br s, NH, 3H), 2.46 (s, 3H), 1.75 (s, 6H), 0.86 (s, 9H).

Example 14

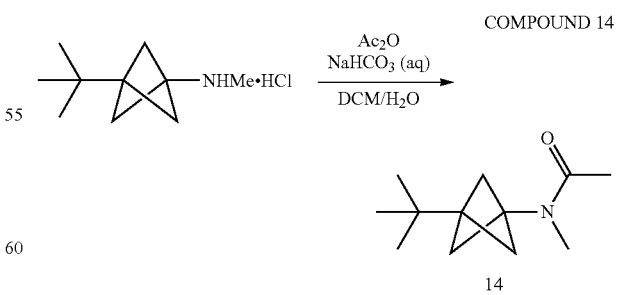

COMPOUND 14

A solution of 13 (0.294 g, 1.55 mmol) in DCM (7.75 mL) and sat. aq. NaHCO$_3$ (15.5 mL) at 0° C. was treated with acetic anhydride (0.791 g, 7.75 mmol, 0.732 mL), and the mixture was stirred at 0° C. After 1.5 h, the solution was extracted with DCM (4×20 mL). The combined organics were washed with sat. aq. NaHCO$_3$ (20 mL) and brine (20 mL), dried (Na$_2$SO$_4$) and concentrated under reduced pressure to afford the crude product as an off-white solid that was further purified by flash chromatography (SiO$_2$, Hexanes/EtOAc) to afford 14 (0.272 g, 90%) as a white solid. $^1$H NMR (400 MHz, CDCl$_3$) δ 2.87 (s, 3H), 2.12 (s, 3H), 1.91 (s, 6H), 0.88 (s, 9H); LC/MS (APCI) m/z 196.2 [C$_{12}$H$_{21}$NO+H]$^+$.

Example 15

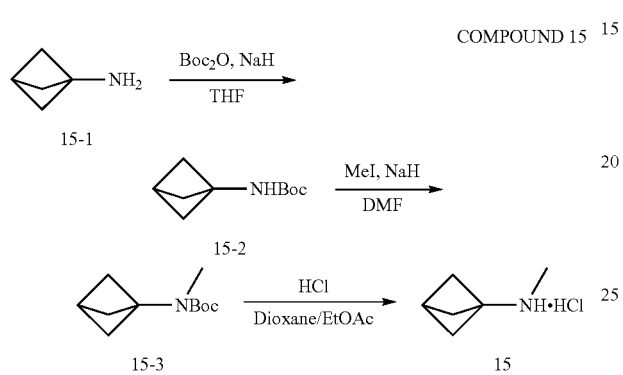

COMPOUND 15

To a suspension of 15-1 (0.800 g, 6.69 mmol) and NaH (60% in mineral oil, 0.562 g, 14.1 mmol) in THF (33.4 mL) at 0° C. was added Boc$_2$O (1.61 g, 7.36 mmol, 1.71 mL). The resulting solution was allowed to warm to rt and stir for 24 h. The solution was then cooled to 0° C. and H$_2$O (2 mL) was slowly added. The mixture was further diluted with H$_2$O (20 mL) and extracted with EtOAc (4×20 mL). The combined organics were dried (Na$_2$SO$_4$) and concentrated under reduced pressure to provide a semi-solid that was further purified by flash chromatography (SiO$_2$, Hexanes/EtOAc) to afford 15-2 (0.708 g, 58%) as a white solid. $^1$H NMR (400 MHz, CDCl$_3$) δ 4.91 (br s, NH, 1H), 2.39 (s, 1H), 2.00 (s, 6H), 1.44 (s, 9H); LC/MS (APCI) m/z 84.1 [C$_{10}$H$_{17}$NO$_2$—C$_5$H$_9$O$_2$+H]$^+$.

To a suspension of NaH (60% in mineral oil, 0.0921 g, 3.84 mmol) in anhydrous DMF (0.710 mL) at 0° C. was added a solution of 15-2 (0.352 g, 1.92 mmol) in DMF (3.84 mL). The mixture was stirred for 5 mins and then MeI (0.817 g, 5.76 mmol, 0.358 mL) was added. The resulting solution was allowed to warm to rt and stir for 4 h. The solution was then cooled to 0° C., and H$_2$O (2 mL) was slowly added. The mixture was diluted with H$_2$O (20 mL) and extracted with EtOAc (3×20 mL). The combined organics were dried (Na$_2$SO$_4$) and concentrated to afford a semi-pure oil that was further purified by flash chromatography (SiO$_2$, Hexanes/EtOAc) to afford 15-3 (0.248 g, 65%) as a yellow oil. $^1$H NMR (400 MHz, CDCl$_3$) δ 2.78 (s, 3H), 2.36 (s, 1H), 2.02 (s, 6H), 1.46 (s, 9H); LC/MS (APCI) m/z 98.1 [C$_{11}$H$_{19}$NO$_2$—C$_5$H$_9$O$_2$+H]$^+$.

A solution of 15-3 (0.247 g, 1.25 mmol) in EtOAc (3.13 mL) was treated with HCl (4.0M in dioxane, 12.5 mmol, 3.13 mL), and the mixture was stirred overnight at rt. The solution was concentrated under reduced pressure to afford the crude compound as an off-white solid. The solid was triturated with Et$_2$O (3×5 mL) and filtered to afford 15 (0.143 g, 86%) as a white solid. $^1$H NMR (400 MHz, DMSO-d$_6$) δ 9.60 (br s, NH, 2H), 2.66 (s, 1H), 2.44 (s, 3H), 1.97 (s, 6H); LC/MS (APCI) m/z 98.1 [C$_6$H$_{11}$N+H]$^+$.

Example 16

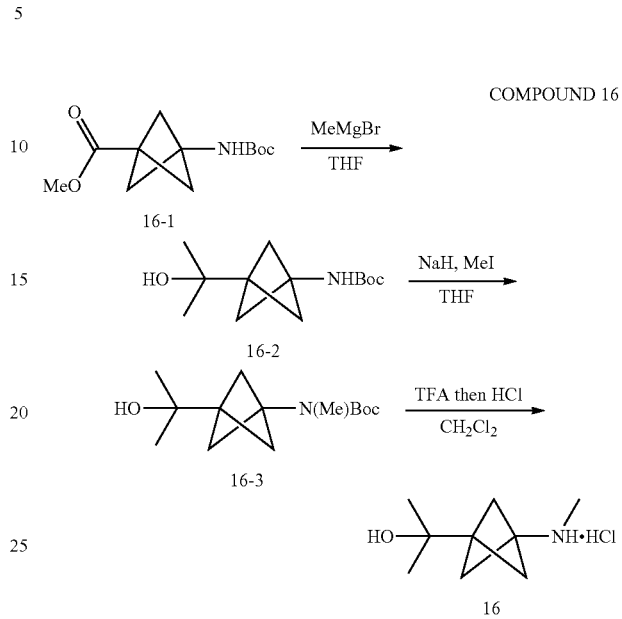

COMPOUND 16

A solution of 16-1 ((prepared according to Eur. J. Org. Chem. 2004, 493-498), 0.400 g, 1.67 mmol) in THF (6.2 mL) was cooled to 0° C. and treated with MgBrCH$_3$ (4.0M in Et$_2$O, 2.1 mL, 6.22 mmol). After 15 mins, the reaction was warmed to rt. After 4 h, the reaction was cooled to 0° C. and quenched with sat. aq. NH$_4$Cl solution (5 mL). After warming to rt, the reaction was diluted with EtOAc and H$_2$O. The organic layer was separated. The aqueous layer was saturated with NaCl(s) and then extracted with EtOAc (3×20 mL). The combined organics were dried (Na$_2$SO$_4$) and concentrated under reduced pressure to afford an oil that was further purified by flash chromatography (SiO$_2$, 0-100% EtOAc/Hexanes) to afford 16-2 (0.190 g, 63%) as a colorless oil. $^1$H NMR (400 MHz, CDCl$_3$) δ 1.93 (s, 6H), 1.47 (s, 9H), 1.21 (s, 6H).

To a solution of 16-2 (0.200 g, 0.829 mmol) in THF (4.14 mL) at 0° C. was added NaH (60% in mineral oil, 0.0497 g, 1.243 mmol). The mixture was stirred for 10 mins, followed by the addition of MeI (0.124 g, 0.870 mmol, 54.2 µL). The resulting solution was allowed to warm to rt, and then stirred overnight. The solution was cooled to 0° C., and H$_2$O (2 mL) was slowly added. The mixture was diluted with H$_2$O (5 mL) and extracted with EtOAc (3×10 mL). The combined organics were dried (Na$_2$SO$_4$) and concentrated to an oil that was further purified by flash chromatography (SiO$_2$, Hexanes/EtOAc) to afford 16-3 (0.120 g, 57%) as a clear colorless oil. $^1$H NMR (400 MHz, DMSO-d$_6$) δ 4.15 (s, 1H), 2.69 (s, 3H), 1.80 (s, 6H), 1.39 (s, 9H), 1.04 (s, 6H); LC/MS (APCI) m/z 156.10 [C$_{14}$H$_{25}$NO$_3$—C$_5$H$_9$O$_2$+H]$^+$.

A solution of 16-3 (120 mg, 0.470 mmol) in DCM (4.7 mL) was cooled to 0° C. and treated with TFA (1.2 mL). The reaction was warmed to rt and stirred for 3 h. The reaction was then concentrated in vacuo to provide a clear colorless oil. The crude mixture was redissolved in CH$_2$Cl$_2$ and re-concentrated (2×) to remove residual TFA. DCM (3 mL) was added to the crude product. The solution was cooled to 0° C., and then treated with HCl (4.0M in dioxane, 8.0 mmol, 2.00 mL). The mixture was stirred for 30 mins at rt.

The solution was concentrated under reduced pressure to afford the crude compound as an off-white solid. The solid was triturated with Et$_2$O and filtered to provide 16 (56.5 mg, 63%) as a white solid. $^1$H NMR (400 Mhz, DMSO-d$_6$) δ 9.41 (br s, 2H), 4.38 (s, 1H), 2.46 (s, 3H), 1.79 (s, 6H), 1.06 (s, 6H); LC/MS (APCI) m/z 156.10 [C$_9$H$_{17}$NO+H]$^+$.

Example 17

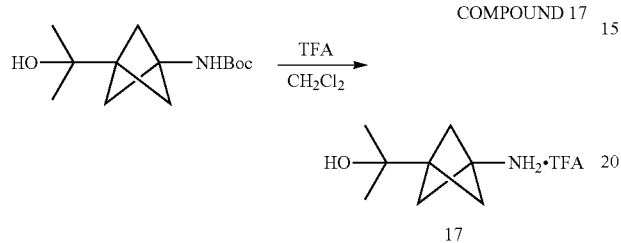

COMPOUND 17

A solution of 16-2 (190 mg, 0.787 mmol) in DCM (8 mL) was cooled to 0° C. and treated with TFA (2 mL). The mixture was warmed to rt and stirred for 2 h. The mixture was concentrated in vacuo. The crude mixture was then dissolved in CH$_2$Cl$_2$ and re-concentrated (2×) to remove residual TFA. The crude reaction was then triturated with EtOAc, followed by Et$_2$O. The mixture was filtered to afford 17 (185.7 mg, 92%) as a white solid. $^1$H NMR (400 Mhz, CD$_3$OD): δ 1.97 (s, 6H), 1.19 (s, 6H); LC/MS (APCI) m/z 142.10 [C$_8$H$_{15}$NO+H]$^+$.

Example 18

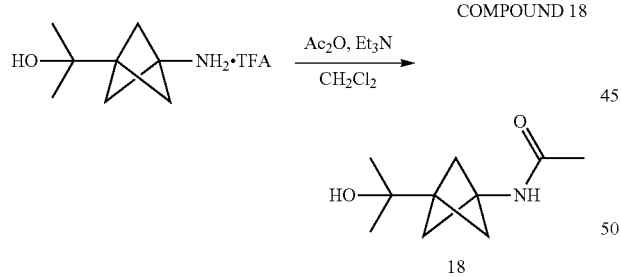

COMPOUND 18

A solution of 17 (185.7 mg, 0.728 mmol) in DCM (3.7 mL) was cooled to 0° C. and treated with triethylamine (355 μL, 2.55 mmol) and acetic anhydride (103 μL, 1.09 mmol). The reaction was warmed gradually overnight. After 16 h, water was added, and the reaction solution was extracted with DCM (3×10 mL). The combined organics were dried (Na$_2$SO$_4$) and concentrated under reduced pressure to afford the crude product as an off-white solid that was further purified by flash chromatography (SiO$_2$, CH$_2$Cl$_2$/MeOH) to afford 18 (0.107 g, 80%) as a white solid. $^1$H NMR (400 Mhz, DMSO-d$_6$): δ 8.26 (s, 1H), 4.09 (s, 1H), 1.76 (s, 6H), 1.73 (s, 3H), 1.03 (s, 6H); LC/MS (APCI) m/z 184.10 [C$_{10}$H$_{17}$NO$_2$+H]$^+$.

Example 19

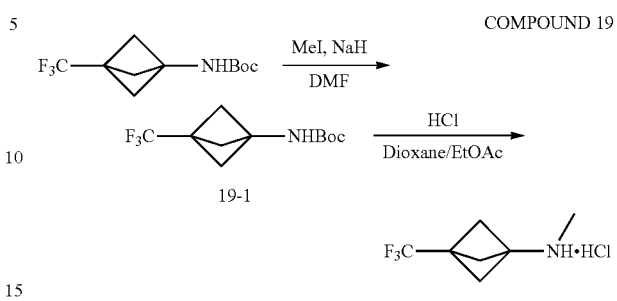

COMPOUND 19

A solution of tert-butyl (3-(trifluoromethyl)bicyclo[1.1.1]pentan-1-yl)carbamate (0.200 g, 0.796 mmol) in DMF (1.990 mL) at 0° C. was treated with NaH (0.038 g, 1.592 mmol). The suspension was stirred for 5 mins followed by the addition of iodomethane (0.149 mL, 2.388 mmol). The solution was allowed to warm to rt and followed by LCMS. Once complete (2 h), the solution was cooled to 0° C. and quenched with H$_2$O (1 mL). The mixture was diluted with H$_2$O (10 mL) and extracted with EtOAc (4×10 mL). The combined organics were dried (Na$_2$SO$_4$) and concentrated to give the crude product which was further purified by flash chromatography (SiO$_2$, Hexanes/EtOAc) to provide 19-1 (126 mg, 60%) as a viscous colorless oil. $^1$H NMR (400 MHz, CDCl$_3$) δ 2.80 (s, 3H), 2.24 (s, 6H), 1.47 (s, 9H); LC/MS (APCI) m/z 166.10 [C$_{12}$H$_{18}$F$_3$NO$_2$—C$_5$H$_9$O$_2$+H$^+$].

A solution of tert-butyl methyl(3-(trifluoromethyl)bicyclo[1.1.1]pentan-1-yl)carbamate (0.125 g, 0.471 mmol) in ethyl acetate (1.178 mL) was treated with HCl (4M in dioxane) (1.178 mL, 4.71 mmol). The solution was stirred at rt overnight. The suspension was concentrated, and then triturated with Et$_2$O (2×10 mL). The precipitate was collected by filtration and the filter cake was washed with Et$_2$O (20 mL). The white solid was dried under vacuum to afford 19 (80.4 mg, 85%) as a white powder. $^1$H NMR (400 MHz, DMSO-d$_6$) δ 10.12 (br s, NH 2H), 2.56 (s, 3H), 2.29 (s, 6H); LC/MS (APCI) m/z 166.10 [C$_7$H$_{10}$F$_3$N+H$^+$].

Example 20

COMPOUND 20

A solution of N-methylbicyclo[1.1.1]pentan-1-amine hydrochloride (0.160 g, 1.20 mmol) in DCM (5.99 mL) and sat. aq. NaHCO$_3$ (12.0 mL) at 0° C. was treated with acetic anhydride (0.610 g, 5.99 mmol, 0.566 mL). The solution was stirred at 0° C. After completion by LCMS (~4 h), the solution was extracted with DCM (4×20 mL). The combined organics were washed with sat. aq. NaHCO$_3$ (20 mL) and brine (20 mL), dried (MgSO4) and concentrated under reduced pressure to afford the crude product as an off-white solid. The crude product was further purified by flash chromatography (SiO$_2$, Hexanes/EtOAc) to afford 20 (0.128 g, 76%) as a colorless oil. $^1$H NMR (400 MHz, CDCl$_3$) δ 2.86 (s, 3H), 2.46 (s, 1H), 2.12 (s, 9H); LC/MS (APCI) m/z 140.10 [C$_8$H$_{13}$NO+H]$^+$.

Example 21

COMPOUND 21

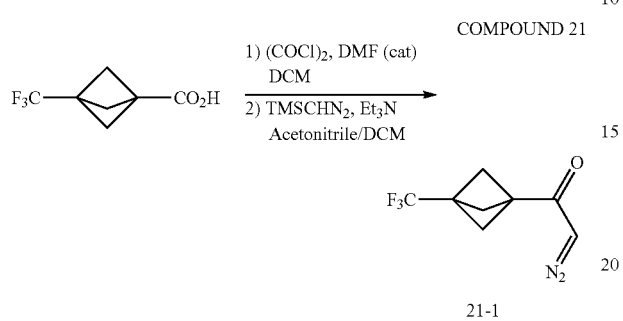

A solution of 3-(trifluoromethyl)bicyclo[1.1.1]pentane-1-carboxylic acid (0.300 g, 1.67 mmol) in DCM (8.33 mL) at 0° C. was treated with oxalyl chloride (0.292 mL, 3.33 mmol) and DMF (couple of drops). Bubbling began immediately, and the solution became homogenous. The solution was warmed to rt and stirred for 2.5 h. The solvent was removed under high vacuum. The residue was dissolved in anhydrous acetonitrile (8.33 mL) and THF (8.33 mL). Et$_3$N (0.557 mL, 4.00 mmol) was added, and after stirring for ~5 mins, the mixture was cooled to 0° C. A 2M solution of TMS-diazomethane (3.33 mL, 6.66 mmol) in ether was added. The solution was warmed to rt and stirred for 5.5 h. Once complete, the reaction was quenched by the addition of 10% citric acid (~10 mL). The majority of the organic layer was removed via rotovap. The mixture was diluted with EtOAc (150 mL) washed with 10% citric acid (20 mL), H$_2$O (20 mL), sat. aq. NaHCO$_3$ (20 mL), and brine (20 mL). The organic layer was dried (Na$_2$SO$_4$) and concentrated to provide the crude product which was further purified by flash chromatography (SiO$_2$, Hexanes/EtOAc) to provide 21-1 (0.190 g, 56%) as a pale yellow oil. $^1$H NMR (400 MHz, CDCl$_3$) δ 5.31 (s, 1H), 2.20 (s, 6H).

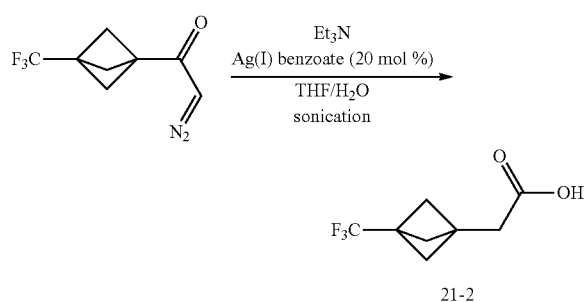

A solution of 2-diazo-1-(3-(trifluoromethyl)bicyclo[1.1.1]pentan-1-yl)ethanone (0.190 g, 0.930 mmol) in THF (27 mL) and water (9.30 mL) was treated with a THF solution (10 mL) of silver(I) benzoate (0.043 g, 0.186 mmol) and Et$_3$N (0.518 mL, 3.72 mmol). The resulting dark solution was sonicated at rt for 30 mins while protected from light. The mixture was concentrated to ~30% of its original volume. The solution was acidified with 1N HCl, diluted with H$_2$O (30 mL) and extracted with EtOAc (4×30 mL). The combined organics were dried (Na$_2$SO$_4$) and concentrated to afford the crude product which was partially purified by flash chromatography (SiO$_2$, Hexanes/EtOAc, 1% AcOH) to give 21-2 (0.125 g, 69%) as a light yellow oil which was used without further purification. $^1$H NMR (400 MHz, CDCl$_3$) δ 2.63 (s, 2H), 2.02 (s, 6H).

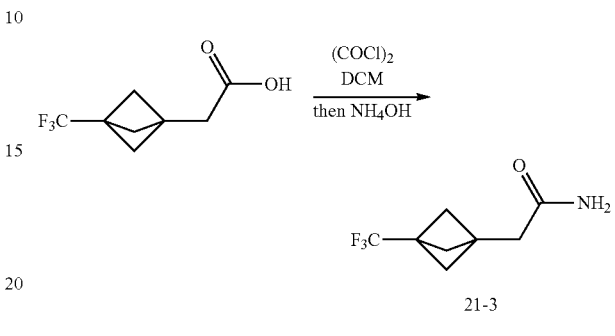

A solution of 2-(3-(trifluoromethyl)bicyclo[1.1.1]pentan-1-yl)acetic acid (0.125 g, 0.644 mmol) in DCM (3.22 mL) was cooled to 0° C. and DMF (2 drops) were added. Oxalyl chloride (0.124 mL, 1.416 mmol) was injected. The solution was allowed to warm to rt and stir for 2.5 h. The solution was then cooled to 0° C. Ammonium hydroxide (4.43 mL, 32.2 mmol) was added in one portion with rapid stirring and a white precipitate formed. The reaction was stirred overnight, diluted with H$_2$O (5 mL) and extracted with EtOAc (5×15 mL). The combined organics were dried (Na$_2$SO$_4$) and concentrated to provide 21-3 (102 mg, 82%) as a white solid, which was used without further purification. $^1$H NMR (400 MHz, DMSO-d$_6$) δ 7.27 (br s, NH, 1H), 6.79 (br s, NH, 1H), 2.31 (s, 2H), 1.89 (s, 6H); LC/MS (APCI) m/z 194.10 [C$_8$H$_{10}$F$_3$NO+H]$^+$.

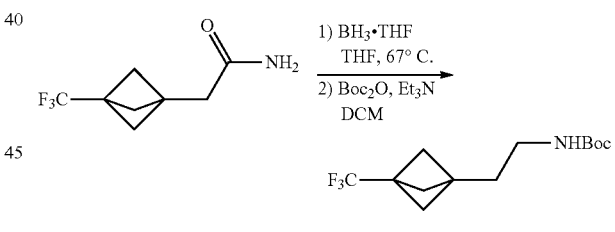

A solution of 2-(3-(trifluoromethyl)bicyclo[1.1.1]pentan-1-yl)acetamide (0.041 g, 0.212 mmol) in anhydrous THF (1.061 mL) was treated with a 1.0M solution of borane tetrahydrofuran complex (0.425 mL, 0.425 mmol) in THF. The solution was heated to 67° C. and stirred until complete as determined by LCMS. Once complete, the reaction was cooled to rt and quenched by the addition of 1M HCl in H$_2$O. The solution was stirred for 1 h, concentrated and used without further purification.

A solution of crude 2-(3-(trifluoromethyl)bicyclo[1.1.1]pentan-1-yl)ethanamine, hydrochloride (0.038 g, 0.176 mmol) in DCM (1.762 mL) was treated with Et$_3$N (0.074 mL, 0.529 mmol) and Boc-anhydride (0.049 mL, 0.211 mmol). The solution was stirred at rt for 2 h, diluted with 10% citric acid (2 mL) and extracted with DCM (4×3 mL). The combined organic layers were dried (Na$_2$SO$_4$) and concentrated to provide the crude product, which was further purified by flash chromatography (SiO$_2$, Hexanes/EtOAc) to provide 21-4 (19.1 mg, 39%) as a white solid. $^1$H NMR (400 MHz, CDCl$_3$) δ 4.45 (br s, NH, 1H), 3.14 (m, 2H), 1.87 (s, 6H), 1.70 (t, J=7.21, 2H), 1.44 (s, 9H); LC/MS (APCI) m/z 180.10 [C$_{13}$H$_{20}$F$_3$NO$_2$—C$_5$H$_9$O$_2$+H]$^+$.

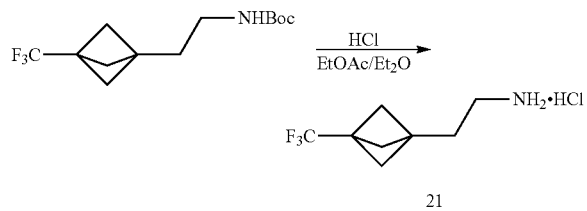

A solution of tert-butyl (2-(3-(trifluoromethyl)bicyclo[1.1.1]pentan-1-yl)ethyl)carbamate (0.0191 g, 0.068 mmol) in ethyl acetate (0.684 mL) was treated with a 2M solution of HCl (0.684 mL, 1.37 mmol) in Et$_2$O. The solution was stirred overnight. Additional HCl in ether (10 eq.) was added, and the reaction was stirred for 48 h. Once complete, the mixture was concentrated, and the resulting white solid was triturated with Et$_2$O (3×1 mL) to provide 21 (10.3 mg, 70%) as a white powder. $^1$H NMR (400 MHz, DMSO-d$_6$) δ 7.82 (br s, NH, 3H), 2.74 (m, 2H), 1.90 (s, 6H), 1.80 (m, 2H); LC/MS (APCI) m/z 180.10 [C$_5$H$_{12}$F$_3$N+H]$^+$.

Example 22

COMPOUND 22

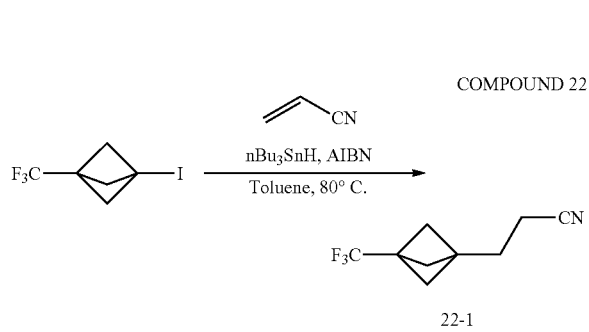

A solution of 1-iodo-3-(trifluoromethyl)bicyclo[1.1.1]pentane (0.137 g, 0.523 mmol) in toluene (2.61 mL) was treated with acrylonitrile (0.069 mL, 1.046 mmol), AIBN (4.29 mg, 0.026 mmol), and nBu$_3$SnH (0.209 mL, 0.784 mmol). The solution was placed in a pre-heated plate at 80° C. and stirred for 4 h. The mixture was concentrated and purified by flash chromatography (SiO$_2$, Hexanes/EtOAc) to provide 22-1 (80.9 mg 82%) as a semi-pure yellow oil. $^1$H NMR (400 MHz, CDCl$_3$) δ 2.34 (t, J=7.1 Hz, 2H), 1.95 (s, 6H), 1.91 (t, J=7.2 Hz, 2H).

A solution of 3-(3-(trifluoromethyl)bicyclo[1.1.1]pentan-1-yl)propanenitrile (0.04 g, 0.211 mmol) in anhydrous MeOH (1.626 mL) was cooled to 0° C. The solution was treated with Boc-anhydride (0.098 mL, 0.423 mmol) and then NiCl$_2$.6H$_2$O (5.03 mg, 0.021 mmol). NaBH$_4$ (0.056 g, 1.480 mmol) was added. Once the addition was complete, the mixture was allowed to warm to rt and stirred. Once complete, the reaction was concentrated and further purified by reverse phase ISCO (C18, H$_2$O/MeCN each w/ 0.1% formic acid) to provide 22-2 (12.3 mg, 20%) as an off-white solid. $^1$H NMR (400 MHz, CDCl$_3$) δ 4.51 (br s, NH, 1H), 3.11 (m, 2H), 1.81 (s, 6H), 1.54-1.48 (m, 4H), 1.44 (s, 9H); LC/MS (APCI) m/z 194.10 [C$_{14}$H$_{22}$F$_3$NO$_2$—C$_5$H$_9$O$_2$+H]$^+$.

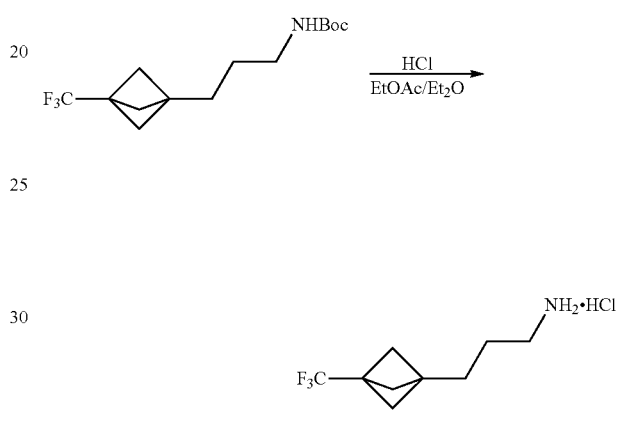

A solution of tert-butyl (3-(3-(trifluoromethyl)bicyclo[1.1.1]pentan-1-yl)propyl)carbamate (0.019 g, 0.065 mmol) in ethyl acetate (0.648 mL) was treated with a 2M solution of HCl (0.648 mL, 1.295 mmol) in diethyl ether. The solution was stirred overnight. Once complete, the suspension was concentrated to dryness, and the resulting white solid was further triturated with Et$_2$O to provide 22 (12.8 mg, 86%) as a white solid. $^1$H NMR (400 MHz, DMSO-d$_6$) δ 7.76 (br s, NH, 3H), 2.76 (m, 2H), 1.84 (s, 6H), 1.80 (m, 2H), 1.53 (m, 4H); LC/MS (APCI) m/z 194.10 [C$_9$H$_{14}$F$_3$N+H]$^+$.

Example 23

COMPOUND 23

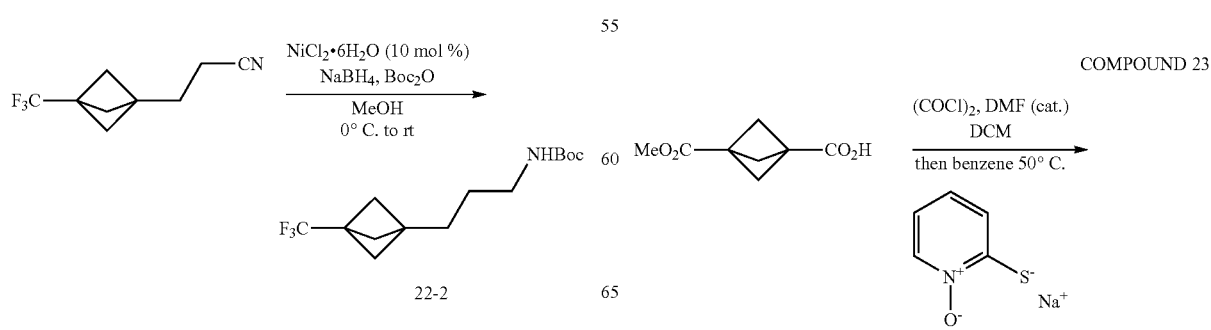

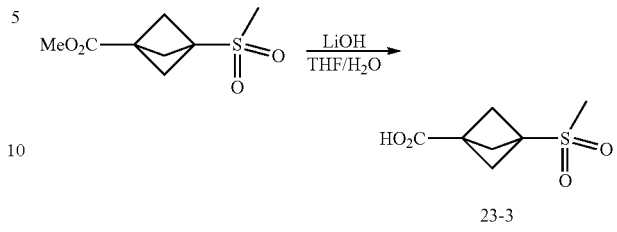

23-1

+

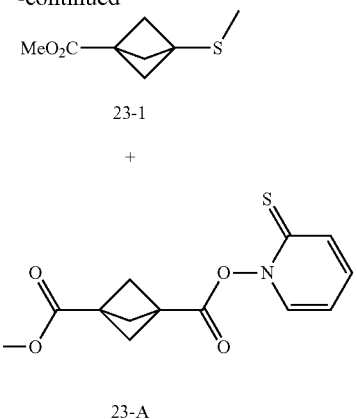

23-A

A solution of 3-(methoxycarbonyl)bicyclo[1.1.1]pentane-1-carboxylic acid (0.500 g, 2.94 mmol) in DCM (14.69 mL, 2.94 mmol) was treated with DMF (2 drops) followed by oxalyl chloride (0.566 mL, 6.46 mmol). The solution was stirred at rt for 2.5 h. The solvent was removed under reduced pressure, and the crude acid chloride was dried under vacuum. The crude acid chloride was re-dissolved in benzene (5.88 mL, 2.94 mmol) and dimethyl disulfide (1.306 mL, 14.69 mmol) was added while the solution was protected from light. In a separate flask, 2-pyridinethiol-1-oxide sodium salt (0.482 g, 3.23 mmol) in benzene (5.88 mL, 2.94 mmol) was heated to 50° C. The solution containing the acid chloride was added dropwise to the 2-pyridinethiol-1-oxide sodium salt (0.482 g, 3.23 mmol) solution while being irradiated with a halogen work lamp. Once the addition was complete, the mixture was irradiated for 1.5 h or until the reaction was complete as determined by LCMS. The reaction was quenched with sat. aq. NaHCO$_3$ (~15 mL), and further diluted with H$_2$O (10 mL). The solution was extracted with EtOAc (4×20 mL). The combined organics were dried (Na$_2$SO$_4$) and concentrated to afford a dark orange oil which was further purified by flash chromatography (SiO$_2$, Hexanes/EtOAc) to provide 23-1 (0.263 g, 52%) as a colorless oil along with the symmetrical thiohydroxamate ester 23-A. $^1$H NMR (400 MHz, CDCl$_3$) δ 3.68 (s, 3H), 2.18 (s, H), 2.08 (s, 3H).

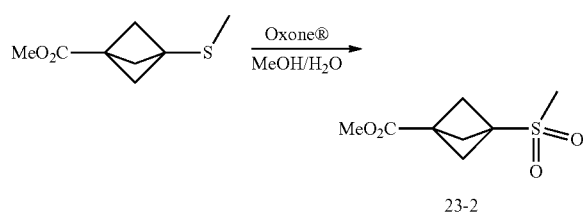

23-2

To a solution of methyl 3-(methylthio)bicyclo[1.1.1]pentane-1-carboxylate (0.263 g, 1.527 mmol) in MeOH (3.82 mL) is added Oxone® (2.82 g, 4.58 mmol) in water (3.82 mL) at 0° C. The solution is allowed to warm to rt and stirred. Once complete as determined by $^1$H NMR and TLC (2.5 h), the mixture was diluted with H$_2$O (30 mL) and extracted with EtOAc (4×20 mL). The combined organics were dried (Na$_2$SO$_4$) and concentrated to afford a white solid which was re-dissolved in EtOAc and filtered through a 0.45 μm filter. Concentration of the solution provided 23-2 (0.280 g, 90%) as a white solid after high vacuum, which required no further purification. $^1$H NMR (400 MHz, CDCl$_3$) δ 3.73 (s, 3H), 2.86 (s, 3H), 2.48 (s, 6H).

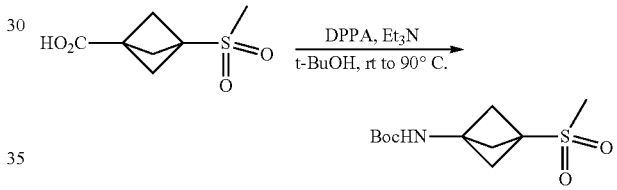

23-3

A solution of methyl 3-(methylsulfonyl)bicyclo[1.1.1]pentane-1-carboxylate (0.279 g, 1.366 mmol) in THF (6.83 mL) was treated with an aqueous 2M solution of LiOH (3.01 mL, 3.01 mmol), and the solution was stirred at rt overnight. The mixture was then diluted with Et$_2$O (5 mL) and extracted with H$_2$O (4×10 mL). The combined aqueous layers were acidified (1N HCl) and extracted with EtOAc (4×10 mL). The combined organics were dried (Na$_2$SO$_4$) and concentrated to afford 23-3 (0.202 g, 78%) as a white powder, which was used without further purification. $^1$H NMR (400 MHz, DMSO-d$_6$) δ 12.90 (br s, COOH, 1H), 2.96 (s, 3H), 2.33 (s, 6H).

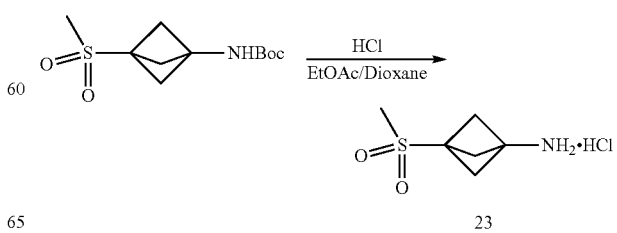

To a suspension of 3-(methylsulfonyl)bicyclo[1.1.1]pentane-1-carboxylic acid (0.202 g, 1.062 mmol) in toluene (5.31 mL) were added crushed 3 Å mol sieves, Et$_3$N (0.296 mL, 2.124 mmol), tert-butanol (0.122 mL, 1.274 mmol) and phosphorazidic acid diphenyl ester (0.275 mL, 1.274 mmol). The solution was stirred at rt for 4 h, and then heated to 90° C. The solution was stirred at overnight. The mixture was cooled to rt and filtered through a 0.45 am filter. The filter was washed with EtOAc, and the filtrate was diluted with H$_2$O (5 mL) and extracted with EtOAc (4×10 mL). The combined organics were dried (Na$_2$SO$_4$) and concentrated to afford the crude product which was further purified by flash chromatography (SiO$_2$, Hexanes/EtOAc) to provide 23-4 (0.173 g, 63%) which solidified upon standing. $^1$H NMR (400 MHz, CDCl$_3$) δ 5.01 (br s, NH, 1H), 2.87 (s, 3H), 2.47 (s, 6H), 1.45 (s, 9H); LC/MS (APCI) m/z 162.0 [C$_{11}$H$_{19}$NO$_4$S—C$_5$H$_9$O$_2$+H]$^+$.

23

A solution of tert-butyl (3-(methylsulfonyl)bicyclo[1.1.1]pentan-1-yl)carbamate (0.173 g, 0.662 mmol) in ethyl acetate (1.655 mL) was treated with a 4M solution of HCl (0.827 mL, 3.31 mmol) in dioxane. The solution stirred at rt overnight. Once complete, the mixture was concentrated to provide the desired product which was further triturated with Et$_2$O to afford 23 (97.3 mg, 74%) as a white solid. $^1$H NMR (400 MHz, DMSO-d$_6$) δ 9.18 (br s, NH, 3H), 3.04 (s, 3H), 2.38 (s, 6H); LC/MS (APCI) m/z 162.0 [C$_{11}$H$_{19}$NO$_4$S—C$_5$H$_9$O$_2$+H]$^+$.

Example 24

COMPOUND 24

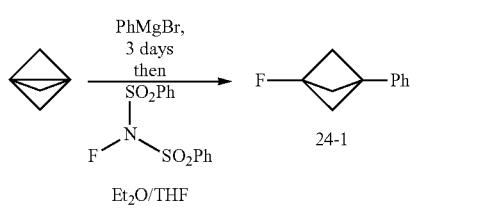

To a solution of propellane (0.36M in Et$_2$O, 10 mL, 3.57 mmol) at 0° C. was added phenylmagnesium bromide (3M in Et$_2$O, 1.190 mL, 3.57 mmol). The cooling bath was removed, and the reaction vessel was sealed and stirred at rt for 3.5 d. The reaction was then cooled to 0° C. and treated with a solution of N-fluorobenzenesulfonimide (NFSI) (1.35 g, 4.3 mmol) in THF (5 mL). Additional THF (5 mL) was added to the mixture to aid in solubility, and the reaction was stirred at rt. After 1 h, H$_2$O was added, and the mixture was extracted with pentane (×5). The combined organic extracts were dried over Na$_2$SO$_4$, filtered and concentrated in vacuo. The product was purified by flash chromatography (SiO$_2$, heptane) to afford 24-1 (113.4 mg, 20%) as a yellow oil. $^1$H NMR (400 MHz, CDCl$_3$) δ 7.35-7.10 (m, 5H), 2.35 (d, J=2.5 Hz, 6H).

A solution of 1-fluoro-3-phenylbicyclo[1.1.1]pentane (113.4 mg, 0.699 mmol) in DCM (1.165 mL): acetonitrile (5.83 mL) was treated with sodium periodate (2.24 g, 10.5 mmol) in water (9 mL) followed by Ruthenium(III) chloride trihydrate (54.8 mg, 0.210 mmol). The reaction was sealed and reacted overnight at rt. The solution was diluted with H$_2$O and extracted with CH$_2$Cl$_2$ (3×). The combined organics were dried over Na$_2$SO$_4$, filtered, and concentrated in vacuo to afford the crude product as a yellow oil. The product was purified by flash chromatography (SiO$_2$, hexanes/EtOAc) to afford 24-2 (34.2 mg, 38%) as a white solid. H-NMR (400 MHz, DMSO-d$_6$) δ 12.75 (s, 1H), 2.29 (d J 2.6 Hz, 6H).

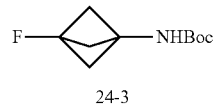

A solution of 3-fluorobicyclo[1.1.1]pentane-1-carboxylic acid (34 mg, 0.261 mmol) in anhydrous tBuOH (1.3 mL) was treated with Et$_3$N (72.8 μL, 0.523 mmol) and DPPA (67.6 μL, 0.314 mmol). The solution was stirred at 30° C. under N$_2$. After 4 h, the solution was warmed to 90° C. and stirred overnight. The solution was concentrated via rotovap, and adsorbed onto silica using DCM. The crude product was purified by flash chromatography (SiO$_2$, Hexanes/EtOAc) to afford 24-3 (40 mg, 76%) as a white solid. ADPPA side product co-eluted with the product, and was separated out in the next step. $^1$H-NMR (400 MHz, CDCl$_3$) δ 2.38 (s, 6H), 1.45 (s, 9H); LC/MS (APCI) m/z 102.1 [C$_{10}$H$_{16}$FNO$_2$—C$_8$H$_9$O$_2$+H]$^+$.

A solution of tert-butyl (3-fluorobicyclo[1.1.1]pentan-1-yl)carbamate (0.04 g, 0.199 mmol) in EtOAc (1.0 mL) was treated with HCl (4.0M in dioxane, 0.994 mmol, 0.25 mL). The mixture was stirred rt overnight. The solution was concentrated under reduced pressure to afford the crude compound as an off-white solid. The solid was triturated with Et$_2$O to afford 24 (13.6 mg, 50%) as a white solid. $^1$H-NMR (400 MHz, DMSO-d$_6$) δ 8.83 (br s, NH, 3H), 2.34 (d, 6H); LC/MS (APCI) m/z 102.1 [C$_5$H$_8$FN+H]$^+$.

Example 25

A solution of 3-(methoxycarbonyl)bicyclo[1.1.1]pentane-1-carboxylic acid (700 mg, 4.11 mmol) in Et$_2$O (16.5 mL) at 0° C. was treated with DMF (32.0 μL, 0.411 mmol) and oxalyl chloride (792 μL, 9.05 mmol). The mixture was warmed to rt. After 70 mins, the solvent was removed in vacuo, and the crude product was dissolved in CCl$_4$ (5 mL). To a separate flask with stir bar was added sodium 2-thioxopyridin-1 (2H)-olate (736 mg, 4.94 mmol), followed by carbon tetrachloride (21 mL). The heterogeneous solution was heated to reflux, and the solution of crude acid chloride in CCl$_4$ was added dropwise over 15 mins under irradiation using a halogen work lamp. After 90 mins, the reaction was cooled to rt. The reaction was added to 1M HCl (aq., 50 mL). The organic layer was removed, and the aqueous layer was washed with DCM (3×30 mL). The combined organic layers were washed with sat. aq. NaHCO$_3$, dried (Na$_2$SO$_4$), filtered and concentrated in vacuo to provide the crude 25-1 as a yellow oil which was used directly for the next reaction without further purification. $^1$H-NMR (400 MHz, CDCl$_3$) δ 3.69 (s, 3H), 2.42 (s, 6H).

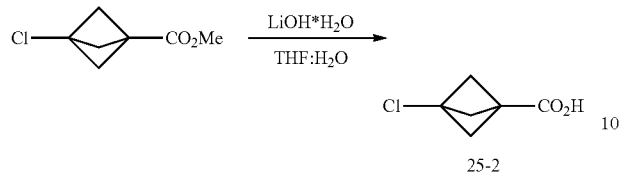

25-2

A solution of crude methyl 3-chlorobicyclo[1.1.1]pentane-1-carboxylate (500 mg, 3.11 mmol) in THF (8.3 mL):H$_2$O (2.1 mL) was treated with lithium hydroxide monohydrate (653 mg, 15.57 mmol) at rt. After 3 h, THF was removed in vacuo, and H$_2$O and Et$_2$O were added. The organic phase was separated, and the aqueous layer was extracted with Et$_2$O. The aqueous layer was acidified with 3M HCl (aq.), and then extracted with DCM (3×30 mL). The combined organic layers (following acidification) were dried (Na$_2$SO$_4$), filtered and concentrated under reduced pressure to afford 25-2 (108.8 mg, 24%) as an off-white solid. $^1$H-NMR (400 MHz, CDCl$_3$) δ 2.45 (s, 6H).

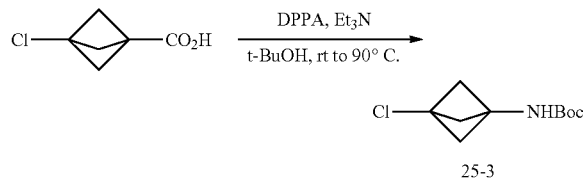

25-3

25-2 (0.108 g, 0.737 mmol) was dissolved in tert-BuOH (3.7 mL). Et$_3$N (0.149 g, 1.47 mmol, 0.21 mL) and activated 3 Å molecular sieves were added followed by diphenylphosphoryl azide (191 μL, 0.884 mmol). The solution was stirred at 30° C. for 4 h, and then heated to reflux overnight. The solution was cooled to rt and then concentrated under reduced pressure. The residual oil was diluted with EtOAc (20 mL) and H$_2$O (20 mL), and extracted with EtOAc (3×20 mL). The combined organics were dried (Na$_2$SO$_4$) and concentrated to afford the crude product that was further purified by flash chromatography (SiO$_2$, Hexanes/EtOAc) to provide 25-3 (67.6 mg, 42%) as a semi-pure white solid. $^1$H NMR (400 MHz, CDCl$_3$) δ 2.36 (s, 6H), 1.44 (s, 9H); LC/MS (APCI) m/z 118.0 [C$_{10}$H$_{19}$ClNO$_2$—C$_5$H$_9$O$_2$+H]$^+$.

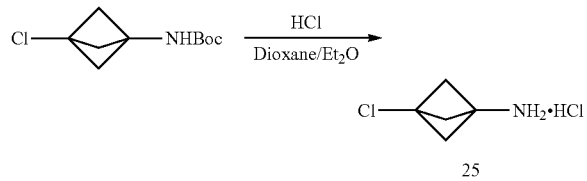

25

To a solution of 25-3 (67.6 mg, 0.311 mmol) in EtOAc (1.55 mL) was added HCl (4 M in dioxane, 0.388 mL, 1.55 mmol). The solution was stirred at rt overnight. After stirring overnight, the mixture became cloudy with partial precipitation of the product. The suspension was concentrated, and the residual solid was triturated with Et$_2$O (2×10 mL). The precipitate was collected by filtration, and the filter cake was washed with Et$_2$O (20 mL). The white solid was dried under vacuum to afford 25 (36.0 mg, 75%) as a white powder. $^1$H NMR (400 MHz, DMSO-d$_6$) δ 8.82 (br s, NH, 3H), 2.38 (s, 6H); LC/MS (APCI) m/z 118.0 [C$_5$H$_8$ClN+H]$^+$.

Example 26

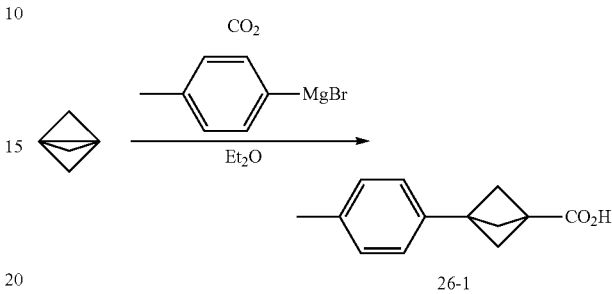

26-1

To a solution of propellane (0.305M in Et$_2$O, 62.0 mL, 18.9 mmol) was added p-tolylmagnesium bromide (0.5M in Et$_2$O, 37.8 mL, 18.9 mmol). The reaction flask was sealed and stirred at rt. After 4 d, the mixture was cooled to 0° C. and dried (CaSO$_4$). C$_{02}$ gas was bubbled through the mixture for 10 mins. The mixture was acidified with 1M HCl, diluted with H$_2$O (40 mL) and extracted with EtOAc (4×30 mL). The combined organics were dried (Na$_2$SO$_4$) and concentrated under reduced pressure to provide the crude product that was further purified by flash chromatography (SiO$_2$, Hexanes/EtOAc) to afford 26-1 (1.96 g, 51%) as an off-white solid. $^1$H NMR (400 MHz, DMSO-d$_6$) δ 12.4 (br s, COOH, 1H), 7.11 (s, 4H), 2.27 (s, 3H), 2.18 (s, 6H).

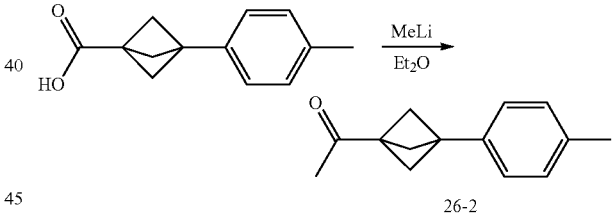

26-2

A solution of 3-(p-tolyl)bicyclo[1.1.1]pentane-1-carboxylic acid (1.0 g, 4.94 mmol) in Et$_2$O (33.0 mL) was treated with methyllithium (1.6M in Et$_2$O, 6.80 mL, 10.88 mmol) at 0° C. After 15 mins, the ice bath was removed, and the mixture was allowed to stir at rt. After 18 h, the reaction was quenched with 3M HCl (aq., 10 mL) and extracted with Et$_2$O (3×). The combined organic extracts were dried (Na$_2$SO$_4$), filtered and concentrated under pressure to provide 26-2 (900 mg, 91%) as a yellow oil which was used directly in the next step. $^1$H NMR (400 MHz, CDCl$_3$) δ 7.13 (s, 4H), 2.33 (s, 3H), 2.27 (s, 6H), 2.19 (s, 3H).

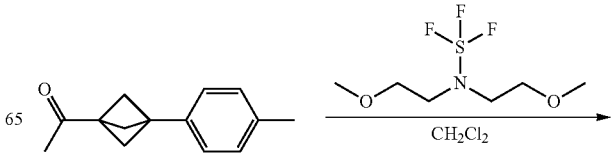

-continued

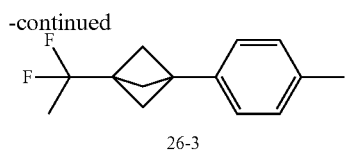

26-3

A solution of 1-(3-(p-tolyl)bicyclo[1.1.1]pentan-1-yl)ethanone (500 mg, 2.50 mmol) in DCM (1.25 mL) was treated with 1,1,1-trifluoro-N,N-bis(2-methoxyethyl)-λ4-sulfanamine (1.66 g, 1.38 mL, 7.49 mmol) dropwise at rt. After 2 d at rt, the mixture was diluted with DCM and slowly added to sat. aq. NaHCO$_3$ (10 mL). The organic layer was separated, and the aqueous layer was washed with DCM (2×). The combined organic layers were washed with 1M HCl, dried (Na$_2$SO$_4$), filtered and concentrated under reduced pressure to provide crude 26-3 (555 mg, 100%) as a brown oil which was used directly in next step. $^1$H NMR (400 MHz, CDCl$_3$) δ 7.12 (s, 4H), 2.33 (s, 3H), 2.09 (s, 6H), 1.60 (t, J=18.1 Hz, 3H).

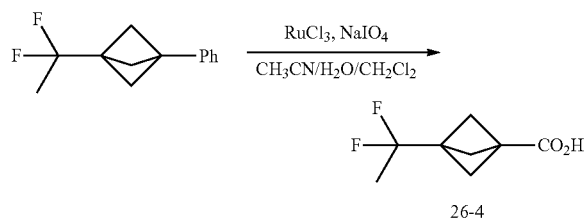

26-4

A solution of crude 1-(1,1-difluoroethyl)-3-phenylbicyclo[1.1.1]pentane (0.275 g, 1.321 mmol) in DCM (2.2 mL):CH$_3$CN (11 mL):H$_2$O (11 mL) was treated with sodium periodate (2.82 g, 13.2 mmol) followed by ruthenium(III) chloride trihydrate (35 mg, 0.13 mmol). The reaction was sealed and reacted overnight at rt. The solution was diluted with H$_2$O and extracted with CH$_2$Cl$_2$ (3×). The combined organics were dried (Na$_2$SO$_4$), filtered, and concentrated under reduced pressure to afford the crude product as a yellow oil. The product was purified by flash chromatography (SiO$_2$, hexanes/EtOAc) to afford 26-4 (70 mg, 30%) as a clear colorless oil. $^1$H-NMR (400 MHz, CDCl$_3$) δ 2.16 (s, 6H), 1.56 (t, J=18.1 Hz, 3H).

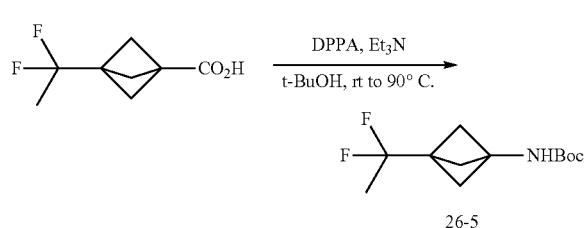

26-5

26-4 (70.0 mg, 0.397 mmol) was dissolved in tert-BuOH (2.0 mL). Et$_3$N (80 mg, 0.80 mmol, 0.11 mL) and activated 3 Å molecular sieves were added followed by diphenylphosphoryl azide (103 µL, 0.477 mmol). The solution was stirred at 30° C. for 4 h, and then heated to reflux overnight. The solution was cooled to rt and then concentrated under reduced pressure. The residual oil was diluted with EtOAc (10 mL) and H$_2$O (10 mL), and extracted with EtOAc (3×10 mL). The combined organics were dried (Na$_2$SO$_4$) and concentrated to afford the crude product that was further purified by flash chromatography (SiO$_2$, Hexanes/EtOAc) to provide 26-5 (33 mg, 34%) as a clear colorless oil. $^1$H NMR (400 MHz, CDCl$_3$) δ 2.08 (s, 6H), 1.56 (t, J=18.0 Hz, 3H), 1.45 (s, 9H); $^{19}$F NMR (376 MHz, CDCl$_3$, unreferenced) δ −96.89.

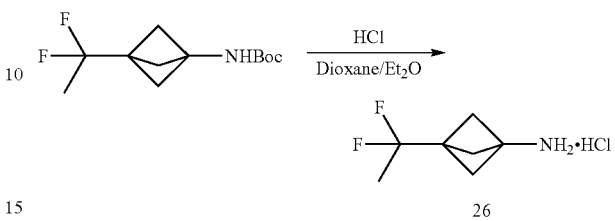

26

To a solution of 26-5 (33.0 mg, 0.133 mmol) in EtOAc (1.00 mL) was added HCl (2 M in Et$_2$O, 0.388 mL, 1.55 mmol). The solution was stirred at rt overnight. After stirring overnight, the mixture became cloudy with partial precipitation of the product. Additional HCl (2 M in Et$_2$O, 0.388 mL, 1.55 mmol) was added, and the reaction was stirred overnight. The suspension was concentrated, and the residual solid was triturated with Et$_2$O (2×8 mL). The precipitate was collected by filtration, and the filter cake was washed with Et$_2$O (10 mL). The white solid was dried under vacuum to afford 26 (20.0 mg, 75%) as a white solid. $^1$H NMR (400 MHz, DMSO-d$_6$) δ 8.89 (br s, NH, 3H), 2.07 (s, 6H), 1.61 (t, J=118.8 Hz, 3H); $^{19}$F NMR (376 MHz, DMSO-d$_6$, unreferenced) 6-94.62.

Example 27

Compounds of Formula (I) with a Fatty Acid Aliphatic Tail

General Procedure

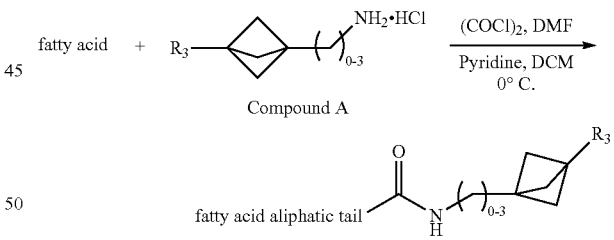

A solution of fatty acid in DCM (~1.1 mL) and DMF (~0.03-0.12 mL) was cooled to 0° C. and oxalyl chloride (~0.328-1.31 mmol) was added dropwise. The mixture was stirred for 1 h followed by the addition of a solution of Compound A in pyridine (~0.5 mmol). The mixture was warmed to rt and stirred for 30 mins. The mixture was diluted with DCM (5 mL) and washed with 10% aq. HCl and then water. The organic layer was dried (Na$_2$SO$_4$), concentrated and purified by flash chromatography (SiO$_2$, Hexanes/EtOAc) to provide a compound of Formula (I) with a fatty acid aliphatic tail.

The following compounds were prepared using the General Procedure described above and the listed reagents and conditions:

| | Fatty acid | Compound A | Product |
|---|---|---|---|
| 27 | Oleic acid, 99% Capilllary GC (0.056 mL, 0.177 mmol) | F$_3$C—[bicyclo]—NH$_2$·HCl | [oleoyl amide with 3-CF$_3$-bicyclo[1.1.1]pentyl]<br>166 mg (>99%)<br>LC/MS (APCI) m/z 416.3<br>[C$_{24}$H$_{40}$F$_3$NO + H]$^+$ |
| 28 | (5Z,8Z,11Z,14Z)-icosa-5,8,11,14-tetraenoic acid (0.054 mL, 0.164 mmol) | F$_3$C—[bicyclo]—NH$_2$·HCl | [arachidonoyl amide with 3-CF$_3$-bicyclo[1.1.1]pentyl]<br>70.4 mg (98%)<br>LC/MS (APCI) m/z 438.3<br>[C$_{26}$H$_{38}$F$_3$NO + H]$^+$ |
| 29 | (5Z,8Z,11Z,14Z)-icosa-5,8,11,14-tetraenoic acid (0.054 mL, 0.164 mmol) | tBu—[bicyclo]—NH$_2$·HCl | [arachidonoyl amide with 3-tBu-bicyclo[1.1.1]pentyl]<br>93 mg (>99%)<br>LC/MS (APCI) m/z 426.4<br>[C$_{29}$H$_{47}$NO + H]$^+$ |
| 30 | (5Z,8Z,11Z,14Z)-icosa-5,8,11,14-tetraenoic acid (200 mg, 0.58 mmol) | H—[bicyclo]—NH$_2$·HCl | [arachidonoyl amide with bicyclo[1.1.1]pentyl]<br>60 mg (28%)<br>LC/MS (ESI) m/z 392.1<br>[C$_{25}$H$_{39}$NO + Na]$^+$ |

Example 28

Compounds of Formula (I)

For some compounds, the foregoing syntheses are exemplary and can be used as a starting point to prepare additional compounds of Formula (I). Examples of additional compounds of Formula (I) are shown below. These compounds can be prepared in various ways, including those synthetic schemes shown and described herein. Those skilled in the art will be able to recognize modifications of the disclosed syntheses and to devise routes based on the disclosures herein; all such modifications and alternate.

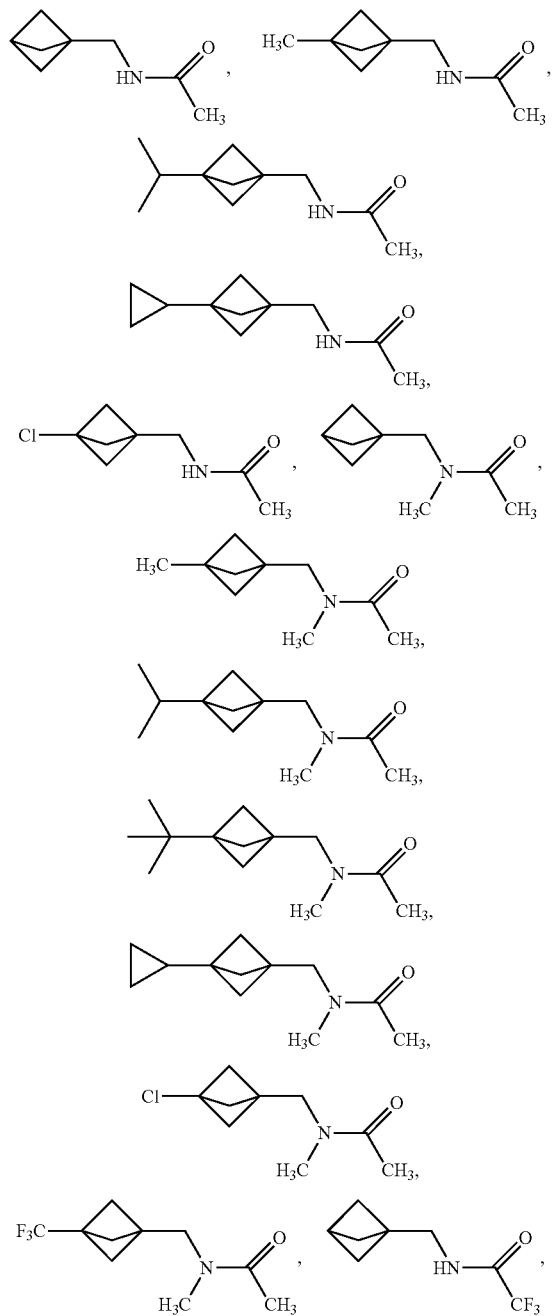

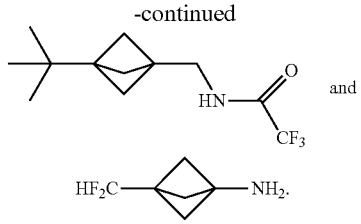

Example A

Formalin Paw Test

One test compound or the vehicle was administered to each mouse in each test group (8 mice per group). Non-fasted male ICR mice weighing 23±3 g were used. Test compounds were administered at a concentration of 3 mg/kg, 10 mg/kg, 15 mg/kg, 30 mg/kg, 60 mg/kg, 100 mg/kg, 200 mg/kg or 300 mg/kg; morphine was administered at a concentration of 5 mg/kg; and acetaminophen was administered at a concentration of 200 mg/kg. The control group received the vehicle (5% DMSO/40% PEG400/20% HPbCD/Saline). After 30 or 60 minutes, a 2% formalin solution (0.02 mL) was injected into one hind paw (subplantar) of each mouse. Responses were measured every 5 minutes after the formalin injection for 35 minutes.

Exemplary results are provided in Tables A and B. As shown in Tables A and B, compounds of Formulae (I) and (II) significantly decreased the pain response in both the early/acute phase (0-10 minutes) and the late/tonic phase (10-35 minutes). The results in Table A are for oral administration; the results in Table B are for intraperitoneal administration. In Tables A and B, 'A' designates <70 licks/sec, 'B' designates ≥70 licks/sec and <165 licks/sec, and 'C' designates ≥165 licks/sec.

TABLE A

| Compound No. | Dosage (mg/kg) | Early Phase | Late Phase |
|---|---|---|---|
| 1 | 200 | A | A |
| 2 | 200 | B | B |
| 3 | 200 | A | C |
| 4 | 200 | A | C |
| 6 | 200 | B | B |
| 8 | 200 | A | A |
| 9 | 200 | B | C |
| 11 | 200 | A | A |
| 12 | 200 | B | C |
| 14 | 200 | A | A |

TABLE B

| Compound No. | Dosage (mg/kg) | Early Phase | Late Phase |
|---|---|---|---|
| 3 | 30 | A | B |
| 16 | 30 | A | C |
| 18 | 30 | B | C |
| 21 | 30 | B | B |
| 22 | 30 | B | B |
| 23 | 30 | B | C |
| 24 | 30 | B | B |
| 25 | 30 | A | A |
| 1c | 30 | B | B |
| 2d | 30 | B | C |

Example B

Glutathione Conjugation Assay

An incubation mixture consisting of 5 μL of 10 mM test compound in DMSO (5 μL of DMSO for negative control; 5 μL of 10 mM acetaminophen in DMSO for positive control), 5 μL of 0.1 M glutathione 25 mM EDTA in water, 50 μL of 100 mM MgCl2 in water, 50 μL of 20 mg/mL pooled human liver microsomes (P-450 content: ~0.5 nmol/mg protein), and 340 μL of 100 mM potassium phosphate buffer (pH 7.4) is preincubated at 37° C. for 10 mins. The reaction is initiated by the addition of 50 μL of 100 mM NADPH solution. The final incubation volume is 0.5 mL. The incubation mixture contains 100 μM test compound or acetaminophen (positive control), 1 mM glutathione, and 1 μM P450. After 60 mins incubation at 37° C., 1 mL of chilled acetonitrile is added to stop the reaction. After the addition of acetonitrile, the sample is vortexed and centrifuged. The supernatant is collected, concentrated in TurboVap under $N_2$ (10 psi) at 30° C. for 35 mins, and transferred to a 96-well plate. The plate is capped and centrifuged. The supernatant is injected for LC-MS/MS analysis.

As described herein, acetaminophen can form the reactive metabolite, N-acetyl-p-benzoquinone imine (NAPQI), which is linked to liver toxicity. Acetaminophen is metabolically activated by cytochrome P450 enzymes to form NAPQI, and NAPQI depletes endogenous glutathione (GSH). The depletion of endogenous glutathione leaves cells vulnerable to oxidative damage. The formation of NAPQI is the result of the phenol or aniline ring of acetaminophen.

Unlike acetaminophen, compound of Formulae (I) and/or (II) do not include a phenol or aniline ring and it is impossible to connect a substituent through a double bond (such as a carbonyl or imine group) at either end of bicyclo[1.1.1]pentane (i.e., at the 1 or 3 positions). As a result, one skilled in the art would not expect compounds of Formulae (I) and/or (II) to form the reactive metabolite NAPQI. A 129 neutral loss scan can be used to search or detect the formation of glutathione conjugates of reactive metabolites.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:
1. A compound of Formula (I), or a pharmaceutically acceptable salt thereof, having the structure:

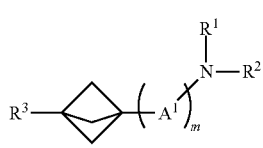

(I)

wherein:
$R^1$ is selected from the group consisting of H, D, an unsubstituted $C_{1-6}$ alkyl and an unsubstituted $C_{1-6}$ haloalkyl;
$R^2$ is $C(=O)R^{2A}$;
$R^{2A}$ is an unsubstituted $C_{6-30}$ alkyl or an unsubstituted $C_{6-30}$ alkenyl;
$R^3$ is selected from the group consisting of H, D, halo, a substituted or unsubstituted $C_{1-8}$ alkyl, an unsubstituted $C_{3-4}$ cycloalkyl, an unsubstituted $C_{1-8}$ haloalkyl and an unsubstituted sulfonyl; and
m is 0.

2. The compound of claim 1, wherein $R^1$ is H.
3. The compound of claim 1A, wherein $R^{2A}$ is an unsubstituted $C_{6-30}$ alkyl.
4. The compound of claim 3, wherein $R^{2A}$ is selected from the group consisting of —$(CH_2)_6CH_3$, —$(CH_2)_8CH_3$, —$(CH_2)_{10}CH_3$, —$(CH_2)_{12}CH_3$, —$(CH_2)_{14}CH_3$, —$(CH_2)_{16}CH_3$, —$(CH_2)_{18}CH_3$, —$(CH_2)_{20}CH_3$, —$(CH_2)_{22}CH_3$ and —$(CH_2)_{24}CH_3O$.
5. The compound of claim 2, wherein $R^{2A}$ is an unsubstituted $C_{6-30}$ alkenyl.
6. The compound of claim 2, wherein $R^{2A}$ is selected from the group consisting of —$(CH_2)_7CH=CH(CH_2)_3CH_3$, —$(CH_2)_7CH=CHCH_2CH=CH(CH_2)_4CH_3$, —$(CH_2)_7CH=CH(CH_2)_7CH_3$, —$(CH_2)_7CH=CHCH_2CH=CH(CH_2)_4CH_3$, —$(CH_2)_7CH=CH(CH_2)_7CH_3$, —$(CH_2)_7CH=CHCH_2CH=CHCH_2CH=CHCH_2CH_3$, —$(CH_2)_9CH=CH(CH_2)_7CH_3$, —$(CH_2)_3CH=CHCH_2CH=CHCH_2CH=CH(CH_2)_4CH_3$, —$(CH_2)CH=CH(CH_2)_7CH_3$, —$(CH_2)_3CH=CHCH_2CH=CHCH_2CH=CHCH_2CH=CHCH_2CH_3$, —$(CH_2)_4CH=CHCH(CH_3)_2$ and —$(CH_2)_2CH=CHCH_2CH=CHCH_2CH=CHCH_2CH=CHCH_2CH_3$.
7. The compound of claim 2, wherein $R^3$ is H.
8. The compound of claim 2, wherein $R^3$ is an unsubstituted $C_{1-8}$ alkyl.
9. The compound of claim 8, wherein $R^3$ is $CH_3$, $CH(CH_3)_2$ or $C(CH_3)_3$.
10. The compound of claim 2, wherein $R^3$ is halo.
11. The compound of claim 10, wherein $R^3$ is F or Cl.
12. The compound of claim 2, wherein $R^3$ is unsubstituted sulfonyl.
13. The compound of claim 12, wherein $R^3$ is $S(O)_2CH_3$.
14. The compound of claim 2, wherein $R^3$ is an unsubstituted $C_{1-8}$ haloalkyl.
15. The compound of claim 14, wherein $R^3$ is $CF_3$, $CHF_2$ or $CF_2CH_3$.
16. The compound of claim 6, wherein $R^3$ is H.
17. The compound of claim 6, wherein $R^3$ is an unsubstituted $C_{1-8}$ alkyl.
18. The compound of claim 17, wherein $R^3$ is $CH_3$, $CH(CH_3)_2$ or $C(CH_3)_3$.
19. The compound of claim 6, wherein $R^3$ is halo.
20. The compound of claim 19, wherein $R^3$ is F or Cl.
21. The compound of claim 6, wherein $R^3$ is unsubstituted sulfonyl.
22. The compound of claim 21, wherein $R^3$ is $S(O)_2CH_3$.
23. The compound of claim 6, wherein $R^3$ is an unsubstituted $C_{1-8}$ haloalkyl.
24. The compound of claim 23, wherein $R^3$ is $CF_3$, $CHF_2$ or $CF_2CH_3$.
25. The compound of claim 1, wherein the compound of Formula (I) is selected from the group consisting of:

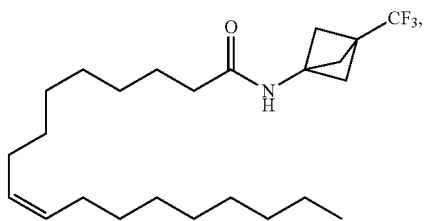
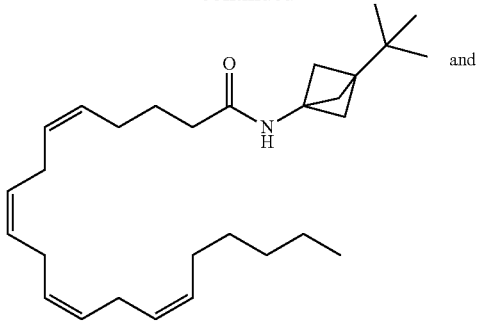
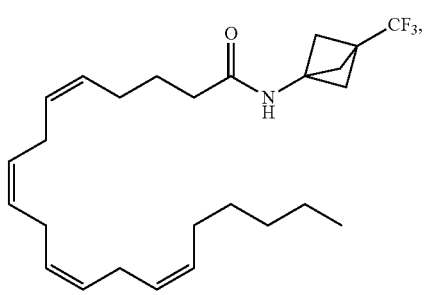
or a pharmaceutically acceptable salt of any of the foregoing.
* * * * *